(12) United States Patent
Arts

(10) Patent No.: US 8,586,295 B2
(45) Date of Patent: Nov. 19, 2013

(54) METHOD FOR SCREENING HIV DRUG SENSITIVITY

(75) Inventor: Eric J. Arts, Cleveland Heights, OH (US)

(73) Assignee: Case Western Reserve University, Euclid, OH (US)

( * ) Notice: Subject to any disclaimer, the term of this patent is extended or adjusted under 35 U.S.C. 154(b) by 913 days.

(21) Appl. No.: 12/279,039

(22) PCT Filed: Feb. 12, 2007

(86) PCT No.: PCT/US2007/061993
§ 371 (c)(1), (2), (4) Date: Nov. 13, 2008

(87) PCT Pub. No.: WO2007/098326
PCT Pub. Date: Aug. 30, 2007

(65) Prior Publication Data
US 2009/0130654 A1    May 21, 2009

Related U.S. Application Data

(60) Provisional application No. 60/772,366, filed on Feb. 10, 2006.

(51) Int. Cl.
*C12Q 1/70* (2006.01)
*C12Q 1/68* (2006.01)
*C12N 15/74* (2006.01)

(52) U.S. Cl.
USPC ............... 435/5; 435/6.1; 435/476; 435/477

(58) Field of Classification Search
None
See application file for complete search history.

(56) References Cited

U.S. PATENT DOCUMENTS

| 5,837,464 A | 11/1998 | Capon et al. |
| 6,242,187 B1 | 6/2001 | Capon et al. |
| 6,351,690 B1 | 2/2002 | Lenz |
| 6,375,925 B1 * | 4/2002 | Tsimikas et al. ............ 424/1.49 |
| 6,406,911 B1 | 6/2002 | Hong |
| 6,410,013 B1 | 6/2002 | Hong |
| 6,489,098 B1 | 12/2002 | Petropoulos et al. |

(Continued)

OTHER PUBLICATIONS

Gao, et al. A Comprehensive Panel of Near-Full-Length Clones and Reference Sequences for Non-Subtype B Isolates of Human Immunodeficiency Virus Type 1. J. Virol. 1998; 72(2): 5680-5698.*

(Continued)

*Primary Examiner* — Zachariah Lucas
*Assistant Examiner* — Stuart W Snyder
(74) *Attorney, Agent, or Firm* — Hahn Loeser & Parks, LLP; John J. Cunniff

(57) ABSTRACT

This present invention provides a method for monitoring ARV resistance, to determine viral fitness, and to forecast possible drug failure. The method provides improved personalized HIV/AIDS care to the patient-physician over existing assays at a reduced cost. This set of assays will utilize the same PCR amplicon of the patient HIV genome, which encompasses all of the drug targeted HIV-1 genes ($pol_{PR-RT-IN}$-$env_{gp120-gp41}$) and not just PR-RT as with the prior systems. The greatest advantage of this method over previous is the rapid cloning of this amplicon into an HIV-1 genome vector through yeast recombination/gap repair. The vectors can be directly passed from yeast to mammalian cell line which has been specifically engineered to produce replication competent HIV-1 particles and to test susceptibility to all ARVs, i.e. PRIs, NRTIs, NNRTIs, T20, as well as entry and integrase inhibitors in development/clinical trials.

8 Claims, 8 Drawing Sheets

(56) References Cited

U.S. PATENT DOCUMENTS

| | | | |
|---|---|---|---|
| 6,653,081 | B2 | 11/2003 | Whitcomb |
| 6,869,759 | B1 | 3/2005 | Parkin et al. |
| 6,942,969 | B2 | 9/2005 | Capon et al. |
| 6,967,076 | B2 | 11/2005 | Hong |

OTHER PUBLICATIONS

Rodenburg, et al. Near Full-Length Clones and Reference Sequences for Subtype C Isolates of HIV Type 1 from Three Different Continents. AIDS Research and Human Retroviruses. 2001. 17(2):161-168.*

Sharkey, et al. Persistence of episomal HIV-1 infection intermediates in patients on highly active anti-retroviral therapy. Nat. Med. 2000; 6(1): 76-81.*

Sharkey, et al. Persistence of episomal HIV-1 infection intermediates in patients on highly active anti-retroviral therapy. Nat. Meal. 2000; 6(1): 76-81.*

Yu and Morrow Essential regions of the tRNA primer required for HIV-1 infectivity. Nuc. Acids Res. 2000; 28(23): 4783-4789.*

Chang, et al. Sequence Features Downstream of the Primer-Binding Site of HIV Type 1 Subtype E Shared by Subtype G and a Subset of Subtype A. AIDS Res. Human Retrovir. 1999; 15(18): 1703-1706.*

Wright, et al. Expression and Characterization of the Trans-Activator of HTLV-III/LAV Virus Science. 1986; 234(4779); 988-992.*

Noskov, et al. A general cloning system to selectively isolate any eukaryotic or prokaryotic genomic region in yeast. BMC Genomics. 2003, 4:16.*

Hwang, et al. Novel Retroviral Vector Transferring a Suicide Gene and a Selectable Marker Gene with Enhanced Gene Expression by Using a Tetracycline-Responsive Expression System. J. Virol. 1996; 70(11): 8138-8141.*

Jansson, et al. Biomarkers for monitoring efficacy of bioremediation by microbial inoculants. Environmental Pollution 107 (2000) 217 223.*

Dawn M. Moore, Eric J. Arts, Yong Gao, Andre J. Marozsan; A Yeast Recombination-Based Cloning System to Produce Chimeric HIV-1 Viruses and Express HIV-1 Genes; Methods in Molecular Biology; vol. 304: Human Retrovirus Protocols: Virology and Molecular Biology; ISSN: 1064-3745; pp. 369-385; 2005; Humana Press Inc., Totowa, NJ.

Tomoo Iwakuma, Yan Cui, Lung-Ji Chang; Self-Inactivating Lentiviral Vectors with U3 and U5 Modifications; Article ID viro. 1999.9850; Virology 261; pp. 120-132; 1999; Academic Press.

Supplementary European Search Report concerning PCT/US2007/061993.

Rodenberg, et al.; Near Full-Length Clones and Reference Sequences for Subtype C Isolates of HIV Type 1 from Three Different Continents; Aids Research and Human Retroviruses; vol. 17, No. 2; 2001; pp. 161-168.

Neumann, et al.; T20-insensitive HIV-1 from naive patients exhibits high viral fitness in a novel dual-color competition assay on primary cells; Virology 333 (2005); 251-262;.

Andre J. Marozsan, Eric J. Arts; Development of a yeast-based recombination cloning/system for the analysis of gene products from diverse human immunodeficiency virus type 1 isolates; Journal of Virological Methods 111; (2003); pp. 111-120.

Marozsan et al.; Differences in the Fitness of Two Diverse Wild-Type Human Immunodeficiency Virus Type 1 Isolates Are Related to the Efficiency of Cell Binding and Entry; Journal of Virology; Jun. 2005; pp. 7121-7134; vol. 79, No. 11.

Edward A. Acheampong, Zahida Parveen, Lois W. Muthoga, Mehrnush Kalayeh, Muhammad Mukhtar, Roger J. Pomerantz, Human Immunodeficiency Virus Type 1 Nef Potently Induces Apoptosis in Primary Human Brain Microvascular Endothelial Cells via the Activation of Caspases, Journal of Virology, Apr. 2005, pp. 4257-4269. vol. 79, No. 7, American Society for Microbiology, downloaded from http://jvi.asm.org/on Feb. 29, 2012 by guest.

\* cited by examiner

METHOD FOR SCREENING HIV DRUG SENSITIVITY

This application claims priority from U.S. Provisional Patent Application No. 60/772,366, filed on Feb. 10, 2006.

This invention was made with government support under cooperative agreements awarded by NIAID, NIH Contract No. AI49170. The government may have certain rights to the invention.

BACKGROUND OF THE INVENTION

Acquired immunodeficiency syndrome (AIDS) is a serious public health concern. AIDS is caused by Human Immunodeficiency Virus type-1 (HIV-1) which can be subdivided into three highly divergent groups that include: M (main), O (outlier), and N (non-M or O). HIV-1 group M strains are responsible for over 95% of infections worldwide and are further separated into at least nine discreet subtypes or clades (A, B, C, D, F, G, H, J, and K), based on the sequence of complete genomes. Additionally, 13 recombinant forms (CRF) have been characterized that further increase the growing HIV-1 diversity. Overall HIV-1 displays 15-40% nucleotide diversity between subtypes and up to 30% nucleotide diversity within a subtype. Additionally, it has been estimated that there can be between 5 and 10% sequence diversity within an infected individual. In the past few years, HIV-1 research on pathogenesis, replication and host-virus interaction has shifted focus from subtype B laboratory strains to primary HIV-1 isolates of all subtypes. Thus, the heterogeneity of HIV-1 has introduced new challenges for cloning and subsequent functional studies.

Standard molecular biological techniques for manipulation of HIV-1 genetic elements are difficult to apply due to poor sequence conservation between different isolates. Unique restriction endonuclease sites are not conveniently distributed across the HIV-1 genome for selective introduction or mutation of various regions or genes. Additionally, the insertion of new restriction sites for cloning is problematic due to the likely disruption of one or more of the multiple open reading frames found in the virus. As a result, current research on HIV-1 replication relies upon a few closely related molecular clones that have matching restriction endonuclease sites. Alternatively, other methods for studying HIV-1 genes involve trans gene expression with respective deletion in a molecular clone to create pseudotyped viruses. However, these pseudotyped viruses are limited to a single round of replication since the full length functional genome is not packaged in the virus particle.

Treatment of individuals infected with HIV-1 with antiretroviral drugs (ARVs) has changed the face of the AIDS epidemic. Previously, all infection with HIV-1 led to AIDS and mortality in an average of two to seven years. The first anti-HIV-1 ARV, 3'-azido-3'-deoxythymidine (AZT, zidovudine, Retrovir®) was approved in 1987 for therapy but was largely unsuccessful in prolonged treatment due to resistance that develops over time. Until the advent of triple drug combination therapy (Highly Active AntiRetroviral Therapy or HAART), drug resistance was common in all treated patients and remained the primary reason for the failure of ARVs to control HIV viremia. Due to the issues of adherence, the need for lifelong therapy, drug tolerance, and incomplete viral suppression, resistance to ARV still emerges in patients undergoing HAART. Unfortunately, ARV resistance triggers a resumption of disease progression unless new ARVs can be administered in a HAART regimen. Pharmaceutical companies have been successful in continually developing new ARV and in different drug classes.

There are now FDA-approved drugs sub-grouped into three classes of anti-HIV ARVs, which target different steps in the HIV lifecycle: reverse transcriptase inhibitors (RTIs) (nonnucleoside (NNRTI), and nucleoside (NRTI)), protease inhibitors (PRIs), and entry inhibitors (EI) (enfutride, fuseon or T20). Several new HIV-1 entry inhibitors that occlude a viral receptor on the host cells have been effective in preclinical development and are now in advanced clinical trials. Additionally, Integrase, another catalytic enzyme of HIV-1 has also been recognized as a rational therapeutic target for the treatment of infection. Integration of the HIV-1 proviral DNA genome into the host genome is essential for viral mRNA transcription but also establishes a stable viral episome in the host genome. Integrase inhibitors and various derivatives could be on the cusp for phase III clinical trials and FDA approval for use in HAART regimens. The continual need for new HIV-1 inhibitors targeting new enzymes or viral processes is due to the emergence of primary resistance to the current PRI and RTIs licensed for therapy. Many of the drug resistant HIV-1 strains selected under a previous regimen also confer cross-resistance to other ARVs in the current FDA-approved arsenal. Cross-resistance limits the use of other drugs in salvage therapy (i.e. following resistance to the first line regimen). Thus, monitoring drug resistance has become a key clinical tool in the management of HIV infected patients by their physicians.

The most basic test for drug resistance is a genotypic drug resistance test which involves sequencing the drug targeted genes PR (encoding protease) and RT (encoding reverse transcriptase) and reporting a predicted resistance pattern. Predicted resistance is based on previous identification of specific resistance mutations and confirmation that these mutations conferred drug resistance in a HIV-1 strain. Since genotypic testing provides only predicted ARV resistance information, many physicians prefer an actual phenotypic drug resistance assay, which involves growing HIV containing patient PR-RT genes in the presence of increasing ARV concentrations. Unlike the multitude of hospital laboratories and companies that perform genotypic drug resistance assays, only two companies offer these HIV phenotypic drug resistance assays, i.e. Monogram Biosciences Inc. (formerly Virologic) and Virco (a division of Johnson & Johnson). These methods employ restriction enzyme cloning, or low efficiency recombination in mammalian cells, respectively. Both methods are very costly and have severe limitations in the ease and adaptability during cloning of patient samples for phenotypic assays. Furthermore, re-development and testing of these phenotypic resistance assays is required to accommodate the new anti-HIV drugs that target other genes or processes (e.g. integration and viral entry) which are now in phase I/II and phase III clinical trials.

A simple sequencing and genotypic analyses is often sufficient to predict resistance due to the relative conservation of HIV-1 PR-RT sequences and well-characterized drug resistance mutations. However, due to the continual emergence of drug resistance, new anti-HIV inhibitors are always needed for effective salvage therapies in patient failing a HAART regimen. Pharmaceutical companies are now pursuing two new classes of ARVs that target the integrase (encoded by IN) and the entry process (involving the env glycoproteins and encoded by the env gene). Several inhibitors are in phase I/II and even phase III clinical trials with a high likelihood of FDA approval within the next two years. Resistance to IN inhibitors appears to be conferred by a distinct set of IN mutations but this data is still very preliminary. In contrast, there is appears to be no distinct pattern of mutations conferring resistance to each entry inhibitor. The env gene is poorly conserved among HIV-1 isolates. Furthermore, there is very large interface between the env gp120/gp41 glycoproteins and the cellular receptors, CD4 and CCR5 (or CXCR4). These two factors contribute to divergent selection of drug resistant mutations which would alter gp120/gp41 structure, transitional rearrangements, and interaction with receptors. Several leading investigators in this field now believe that it may be impossible to predict drug resistance through DNA sequencing/genotype analyses.

Thus, new methods are necessary for cloning into the full HIV-1 genome that also accommodate for the high genetic diversity seen between strains.

Homologous recombination in yeast has been used to clone genes or sequences without the use of restriction endonucleases. However, this cloning technique is unnecessary for most eukaryotic and prokaryotic sequences due to the limited diversity and conservation of sequences cleaved by restriction endonucleases. Yeast gap repair facilitates recombination between a PCR product and a linearized vector via short sequences of comparable homology in both DNA fragments. Selection of the recombined plasmids and their maintenance in yeast is mediated by positive and negative selectable elements within the vector. Finally, these plasmids can be rapidly isolated from yeast and shuttled into *E. coli* for further subcloning.

The use of a yeast-based recombination method that can be used to clone HIV-1 gag, pol or env sequences of any subtype into a vector for expression in mammalian cells, or for rapid subcloning into a HIV-1 molecular clone has been previously described. The method is not limited by the location of restriction endonuclease sites and holds significant advantages over standard cloning techniques such as: (1) PCR-based TA cloning methods where exogenous sequence must be introduced for subsequent gene expression or subcloning, or (2) PCR-based methods that introduce foreign restriction endonuclease sites by mutating HIV-1 sequence in the primer binding sites. According to that method, an HIV-1 sequence is PCR-amplified and recombined into the vector using a yeast-based recombination system within the proper reading frame, allowing entire genes, gene domains or sub-domains to be studied in context of specific functions. The vector may be transfected into higher eukaryotes for protein expression and functional studies. The HIV-1 genes from this vector can also be shuttled into the infectious HIV-1 molecular clone by classic restriction enzyme/bacterial cloning, which will then provide a vector to produce replication-competent virus in mammalian cells. Unfortunately, the repeated HIV-1 sequences at either end of the genome prevents the use of yeast-based cloning. Yeast simply recombines out the entire HIV-1 coding sequence and generates a non-functional HIV-1 cloning vector.

A need exists for a virus screening system that does not depend on a vector that can recombine to excise virus genes out of the vector and does not depend on the use of restriction endonucleases to create the isolates to be screened.

A need also exists for a method of screening that is not limited to specific genes of the HIV genome. A need further exists for a method of virus screening that can be used to determine susceptibility to various HIV inhibitors, most importantly the entry inhibitors such as CCR5 antagonists. An additional need exists for a method to test susceptibility of viral strains to drugs that target multiple viral constituents.

It is known that as a retrovirus, HIV-1 carries a genome consisting of ribonucleic acid (RNA) rather than deoxyribonucleic acid (DNA). In addition to the same core gene structure shared among all retroviruses (i.e. the gag, pol, and env genes), the HIV-1 genome also harbors several genes found in multiply and singly spliced RNA transcripts (i.e. vif, vpr, tat, rev, vpu, and nef) that encode for several accessory proteins. Replication of the virus after infection of a cell involves reverse transcription of the viral RNA, that is, the creation of a DNA copy of the RNA template. This is accomplished by the enzyme reverse transcriptase. Reverse transcription begins in the primer binding site (pbs) immediately adjacent to one of the two end regions of the linear HIV genome known as the long terminal repeats (or LTRs), specifically the 5' LTR. The 5' LTR contains two subregions or segments, the “R” segment, followed by the “U5” segment. The 3' LTR also contains an R segment, which is identical to the R segment of the 5' LTR, but the 3' R segment is preceded by a “U3” segment.

FIG. 1 provides a schematic representation of reverse transcription of a retroviral RNA genome. Reverse transcriptase begins synthesizing a DNA strand from a host $tRNA^{Lys,3}$ annealed to the pbs region approximately 100-200 nucleotides from the 5' end of the viral RNA strand and will proceed to make a DNA copy of the U5 and R RNA segments of the 5' LTR (termed (−) strand strong stop DNA). When reverse transcriptase makes a DNA copy of all the RNA nucleotides at the 5' end of the RNA strand, ribonuclease H (RNase H) will degrade the R segment of the viral RNA. The reverse transcriptase will then change templates to the 3' LTR of the same or a different viral RNA strand. The R segment of the newly synthesized DNA is complementary to and binds to the “R” region of the 3' LTR of the virus. The DNA segment then acts as a primer for further synthesis of a DNA copy of the viral RNA by reverse transcriptase through the U3 region and then the remainder of the viral genome, resulting in a full length DNA copy of the viral RNA genome. The RNA strand is then degraded by RNase H. Synthesis of a complementary second DNA strand begins at the site denote “PPT.” Strand transfer is also thought to occur with the synthesis of the double stranded DNA.

SUMMARY OF THE INVENTION

In general, two retroviral nucleic acid sequences are provided. One is devoid of at least a majority of the sequence for one of the two long terminal repeat regions but retains other HIV-1 genetic elements. The specific genetic element deleted is the R and U5 sequences of the 5' long terminal repeat region. Another nucleic acid complements the first by containing the 5' long terminal repeat and a short upstream HIV-1 RNA fragment. This nucleic acid contains the R and U5 sequences of the 5' long terminal repeat region followed by the primer binding sequence (PBS) and the packaging sequence. A vector may comprise such a nucleic acid sequence. A vector may also comprise at least one origin of replication, a nucleic acid sequence that is substantially identical to the primer binding site of HIV-1, a selectable genetic element and a nucleic acid sequence that is substantially identical to the 3' long terminal repeat sequence of HIV-1. The selectable genetic element may be URA3, for example.

A complementation genome, that is, a nucleic acid comprising a retroviral sequence devoid of the sequences encoding an envelope gene and a 3' long terminal repeat region of the retrovirus may also be provided. It may optionally also be devoid of at least a portion of the retrovirus pol gene and further optionally, devoid of at least a portion of the retrovirus gag gene.

A method of determining the sensitivity of a retroviral strain to one or more antiviral compounds is provided. The method may comprise providing a first vector comprising at least one origin of replication, a sequence substantially identical to the primer binding site of the retroviral strain, a selectable marker and a sequence of at least a portion of a known retroviral strain devoid of a first long terminal repeat region, providing a retroviral sequence isolated from a patient wherein the sequence isolated from a patient is modified to comprise sequence substantially identical to at least a portion of the selectable marker and transforming a yeast cell line with the first vector and the retroviral sequence. The method further includes selecting against the presence of the selectable marker to provide a transformed yeast cell line having a second vector, wherein the selectable marker of the first vector has been replaced by the retroviral sequence. The second vector is used to transform a second cell line with a third vector, wherein the third vector comprises retroviral sequence substantially identical to the first long terminal repeat region, to provide a transformed second cell line. Viable retrovirus particles are isolated from the transformed second cell line and contacted with a third cell line in the presence of one or more antiviral compounds. The method then includes determining the susceptibility of the retrovirus to the one or more antiviral compounds.

Figure 1:
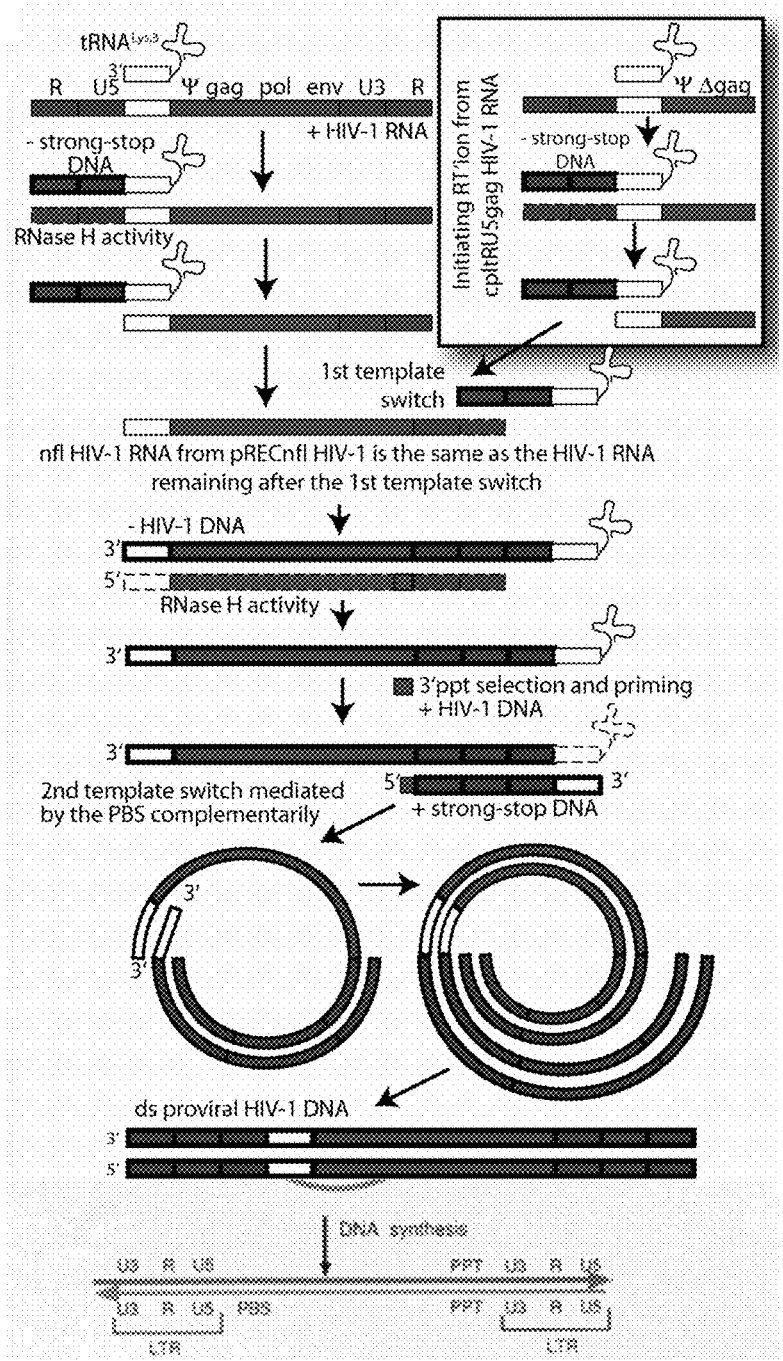
FIG. 1 is a schematic representation of reverse transcription of a retroviral genome.
Figure 2A:
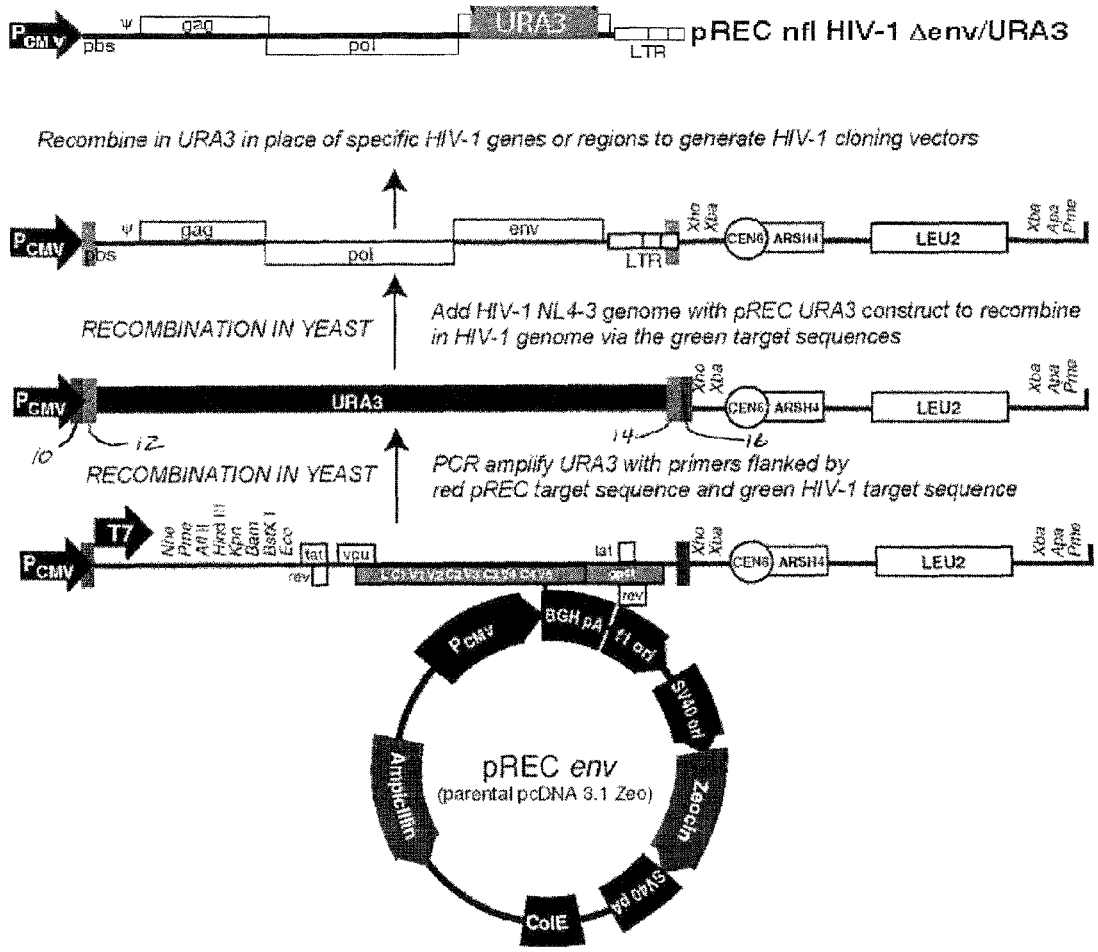
FIG. 2A is a representation of a vector containing a near full length HIV sequence, its synthesis and its use to create a selectable vector containing HIV-1 genes.

The PCR product is then used with the vector (pREC env) to transform yeast cells. Optionally, the vector may be linearized with a restriction enzyme that does not cut the PCR product to increase the frequency of recombination between the PCR product and the corresponding sequences in the vector. The resulting plasmid in the example shown in FIG. 2A is referred to as pREC Ura3. Recombinants (pREC Ura3) are selected by growing on media that selects for both of the selectable markers each contributed by the vector and the PCR product, in this example, by growing the yeast cells on leucine- and uracil-deficient media.

The recombined vector (pREC Ura3, in the example) may then be used to further act as a vector for further recombination with an HIV strain. Recombination occurs in yeast between the homologous regions of the recombined vector and the HIV genome; in the example presented, between the pbs and the 3' LTR. Recombinants may be selected by selecting against the PCR-derived selectable marker. Where the Ura3 gene is the selectable marker, this may be accomplished by growing the yeast cells on fluoroorotic acid (5-fluoro-1,2,3,6-tetrahydro-2,6-dioxo-4-pyrimidine carboxylic acid, or FOA) which is converted into a toxic metabolite by cells expressing the Ura3 gene. This results in a vector containing an entire HIV genome, such as the NL4-3genome, but devoid of the 5' LTR (a primary recombinant). In the example shown in FIG. 2A, this plasmid is referred to as pREC nfl HIV-1. The sequence of PREC nfl HIV-1 is provided as SEQ. ID. NO. 1. In SEQ. ID. NO. 1, the sequence derived from HIV-1 extends from residue 1 to residue 9076. The location of the Bam HI restriction endonuclease site at residue 7833 should be noted, as this location figures into the orientation of plasmids additionally containing genes encoding fluorescent proteins, as described hereinbelow.

The vector containing a near full length HIV-1 genome may then be used for further recombination with other HIV isolates or portions of the genome of other HIV isolates via homologous recombination in yeast as described above. In this way, individual variations in genes may be examined and interactions of variant gene products may be examined with more well characterized gene products. In the example shown in FIG. 2A, URA3 is recombined in yeast similar to the earlier steps to replace a section of the env gene in pREC nfl HIV-1 to create pREC nfl HIV-1 Δenv/URA3, which contains the nfl HIV-1 sequence except with a URA3 gene inserted into and replacing a portion of the envelope gene. Such recombinants may again be selected by growing the yeast transformed with the URA3 and the pREC nfl HIV-1 Δenv/URA3 on leucine-deficient, uracil-deficient media. In the example shown, the 5' and 3' ends of the env gene remain so as to permit further recombination as described below.

Figure 2B:
FIG. 2B is a representation of the use of a selectable vector containing HIV-1 genes and its use to clone a patient-specific HIV 1 PCR product to create a near full length HIV-1 isolate containing a specific segment of DNA that corresponds to a genetic sequence of HIV-1 isolated from a patient.
Figure 2B:
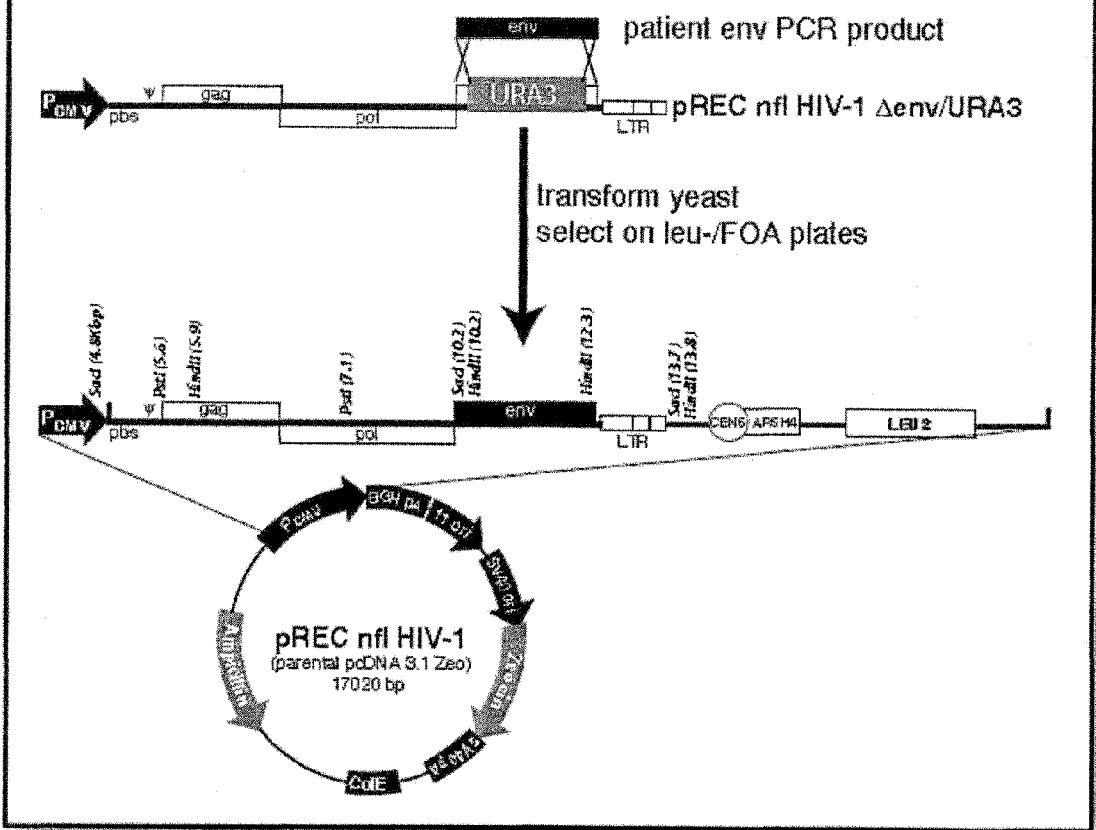

Constructs such as pREC nfl HIV-1 Δenv/URA3 may be utilized to examine the properties such as drug resistance conferred by different env genes in a standardized environment, that is, in relation to well defined components of an HIV strain, such as NL4-3. However, as explained more fully below, any portion of the HIV-1 genome may be replaced with a selectable marker such as URA3. In FIG. 2B, pREC nfl HIV-1 Δenv/URA3 is shown as a vector for recombination with a patient-derived env gene, generated for example, by PCR. The PCR product recombines with the remaining portions of the env gene flanking the URA3 gene in pREC nfl HIV-1 Δenv/URA3. The resulting recombinants contain a near full length HIV-1 sequence from NL4-3, with a patient-derived env gene replacing the env gene of NL4-3. Such recombinants may be selected by selecting against the URA3 gene, that is, by growing the yeast on media containing FOA.

Other constructs can be made in a similar manner as that described above, starting with pREC nfl HIV-1, and replacing other portions of the HIV genome with a selectable marker such as URA3. A list of near full length HIV-1 isolates containing a URA3 substitution that have been made is provided in Table 1. Table 1 lists the region of HIV-1 replaced by URA3, the location of the substitution relative to the sequence of isolate NL4-3, and the size of the portion of the HIV genome replaced with URA3. One such construct replaces a portion of the pol gene with URA3, pRECnfl HIV-1Δpol/URA3. The sequence of pRECnfl HIV-1Δpol/URA3 is provided as SEQ. ID. No. 2.

A list of oligonucleotide primers used to make the substitutions listed in Table 1, are provided in Table 2 below. The oligonucleotides, some of which are degenerate primers, amplify a section of the HIV-1 genome, which is then recombined into the vector by homologous recombination. The degenerate primers permit the target sequences to be amplified despite variations in the target sequences.

TABLE 1 pREC NFL HIV-1 vectors with various coding region replacements with URA3

| pREC-$_{NFL-HIV-1}$ Deletions | Location of Deletion in NL4-3 | Size of Deletion |
| --- | --- | --- |
| Δhiv-1\URA3 | 790-9533 | 8745 |
| Δgag-pol-env\URA3 | 790-8785 | 7998 |
| Δgag-pol-env2\URA3 | 790-8264 | 7476 |
| Δgag-pol\URA3 | 790-5096 | 4515 |
| Δgag\URA3 | 790-2292 | 1503 |
| Δgag p17\URA3 | 790-1185 | 396 |
| Δgag p24\URA3 | 1186-1878 | 693 |
| Δgag p7\URA3 | 1921-2133 | 213 |
| Δgag p6\URA3 | 2134-2292 | 159 |
| Δpol\URA3 | 2085-5096 | 3012 |
| Δpol prot\URA3 | 2253-2549 | 297 |
| Δpol rt\URA3 | 2550-3869 | 1320 |
| Δpol prot-rt\URA3 | 2253-3869 | 1617 |
| Δpol rnase H\URA3 | 3870-4229 | 360 |
| Δpol-env\URA3 | 2085-8785 | 6701 |
| Δpol-env-s\URA3 | 2085-8264 | 6180 |
| Δpol int\URA3 | 4230-5096 | 867 |
| Δvif-vpr-tat-rev vpu-env-nef\URA3 | 5041-9407 | 4367 |
| Δvif\URA3 | 5041-5619 | 579 |
| Δvpr\URA3 | 5559-5849 | 291 |
| Δtat\URA3 | 5830-8459 | 2630 |
| Δtat-ex1\URA3 | 5830-6044 | 215 |
| Δtat-ex2\URA3 | 8369-8459 | 91 |
| Δrev\URA3 | 5969-8643 | 2675 |
| Δrev-ex1\URA3 | 5969-6044 | 76 |
| Δrev-ex2\URA3 | 8370-8643 | 274 |
| Δvpi\URA3 | 6061-6306 | 246 |
| Δenv\URA3 | 6221-8785 | 2565 |
| Δenv-s\URA3 | 6221-8264 | 2043 |
| Δenv gp120\URA3 | 6221-7747 | 1527 |
| Δenv gp120 v1/v2\URA3 | 6611-6802 | 192 |
| Δenv gp120 v3\URA3 | 7100-7207 | 108 |
| Δenv gp120 v4/v5\URA3 | 7368-7627 | 260 |
| Δenv gp41\URA3 | 7748-8785 | 1038 |
| Δenv gp41-s\URA3 | 7748-8264 | 517 |
| Δrre\URA3 | 7716-8069 | 354 |
| Δnef\URA3 | 8787-9407 | 621 |
| Δ3'-ltr U3\URA3 | 9076-9533 | 458 |

TABLE 2

Oligonucleotide primers for the insertion of HIV-1 coding regions into pREC NFL HIV-1 vectors in Table 1

| Primer Name | pREC-$_{NFL-HIV-1}$ Deletions | Location | Sequence |
|---|---|---|---|
| ext B int.11 | Δpol int\URA3 | 5197→5246 | SEQ. ID. NO. 8 |
| ext B int.12 | Δpol int\URA3 | 5185→5234 | SEQ. ID. NO. 9 |
| intern B int.13 | Δpol int\URA3 | 5157→5206 | SEQ. ID. NO. 10 |
| intern B int.14 | Δpol int\URA3 | 5127→5176 | SEQ. ID. NO. 11 |
| intern F int.7 | Δpol int\URA3 | 4171→4220 | SEQ. ID. NO. 12 |
| intern F int.8 | Δpol int\URA3 | 4147→4196 | SEQ. ID. NO. 13 |
| ext F int.9 | Δpol int\URA3 | 4120→4169 | SEQ. ID. NO. 14 |
| ext F int.10 | Δpol int\URA3 | 4068→4117 | SEQ. ID. NO. 15 |
| int B Rnase.7 | Δpol rnase H\URA3 | 4231→4280 | SEQ. ID. NO. 16 |
| int BRnase.8 | Δpol rnase H\URA3 | 4248→4297 | SEQ. ID. NO. 16 |
| ext B Rnase.9 | Δpol rnase H\URA3 | 4272→4321 | SEQ. ID. NO. 17 |
| ext B Rnase.10 | Δpol rnase H\URA3 | 4290→4339 | SEQ. ID. NO. 18 |
| int F POL.5 | Δpol\URA3 | 2014→2063 | SEQ. ID. NO. 19 |
| int F POL.6 | Δpol\URA3 | 1992→2041 | SEQ. ID. NO. 20 |
| ext F POL.7 | Δpol\URA3 | 1984→2033 | SEQ. ID. NO. 21 |
| ext F POL.8 | Δpol\URA3 | 1962→2011 | SEQ. ID. NO. 22 |
| int F p7.7 | Δgag p7\URA3 | 1843→1892 | SEQ. ID. NO. 23 |
| int F p7.8 | Δgag p7\URA3 | 1834→1883 | SEQ. ID. NO. 24 |
| ext F p7.9 | Δgag p7\URA3 | 1792→1841 | SEQ. ID. NO. 25 |
| ext F p7.10 | Δgag p7\URA3 | 1807→1856 | SEQ. ID. NO. 26 |
| Ext B VPU.3 | Δvpu\URA3 | 6385→6434 | SEQ. ID. NO. 27 |
| EXt B VPU.4 | Δvpu\URA3 | 6372→6421 | SEQ. ID. NO. 28 |
| INT B VPU.5 | Δvpu\URA3 | 6349→6398 | SEQ. ID. NO. 29 |
| INT B VPU.6 | Δvpu\URA3 | 6341→6390 | SEQ. ID. NO. 30 |
| Int F gp120.3 | Δenv gp120\URA3 | 6173→6222 | SEQ. ID. NO. 31 |
| Int F gp120.4 | Δenv gp120\URA3 | 6143→6192 | SEQ. ID. NO. 32 |
| Ext F gp120.5 | Δenv gp120\URA3 | 6090→6139 | SEQ. ID. NO. 33 |
| Ext F gp120.6 | Δenv gp120\URA3 | 6066→6118 | SEQ. ID. NO. 34 |
| TAT REC CON FWD 1 | Δtat\URA3 | 5758→5808 | SEQ. ID. NO. 35 |
| TAT REC CON FWD 2 | Δtat\URA3 | 5732→5782 | SEQ. ID. NO. 36 |
| TAT REC CON FWD 3 | Δtat\URA3 | 5713→5762 | SEQ. ID. NO. 37 |
| TAT REC CON BWD 4 | Δtat\URA3 | 8425→8474 | SEQ. ID. NO. 38 |
| TAT REC CON BWD 5 | Δtat\URA3 | 8429→8478 | SEQ. ID. NO. 39 |
| TAT REC CON BWD 6 | Δtat\URA3 | 8439→8488 | SEQ. ID. NO. 40 |
| TAT REC CON BWD 7 | Δtat\URA3 | 8493→8542 | SEQ. ID. NO. 41 |
| EXT TAT REC CON FWD 8 | Δtat\URA3 | 5488→5537 | SEQ. ID. NO. 42 |
| EXT TAT REC CON FWD 9 | Δtat\URA3 | 5428→5477 | SEQ. ID. NO. 43 |
| EXT TAT REC CON FWD 10 | Δtat\URA3 | 5409→5458 | SEQ. ID. NO. 44 |
| EXT TAT REC CON BWD 11 | Δtat\URA3 | 8699→8748 | SEQ. ID. NO. 45 |
| EXT TAT REC CON BWD 12 | Δtat\URA3 | 8640→8689 | SEQ. ID. NO. 46 |
| EXT TAT REC CON BWD 13 | Δtat\URA3 | 8562→8611 | SEQ. ID. NO. 47 |
| POL RT REC CON FWD 7 | Δpol rt\URA3 | 2458→2507 | SEQ. ID. NO. 48 |
| POL RT REC CON FWD 8 | Δpol rt\URA3 | 2445→2494 | SEQ. ID. NO. 49 |
| POL PRO REC CON BWD 7 | Δpol prot\URA3 | 2604→2653 | SEQ. ID. NO. 50 |
| POL PRO REC CON BWD 8 | Δpol prot\URA3 | 2588→2637 | SEQ. ID. NO. 51 |
| VPR REC CON BWD 4 | Δvpr\URA3 | 5911→5960 | SEQ. ID. NO. 52 |
| VPR REC CON BWD 5 | Δvpr\URA3 | 5877→5926 | SEQ. ID. NO. 53 |
| VPR REC CON BWD 6 | Δvpr\URA3 | 5851→5900 | SEQ. ID. NO. 54 |
| GAG P17 REC CON FWD 7 | Δgag p17\URA3 | 666→715 | SEQ. ID. NO. 55 |
| GAG P17 REC CON FWD 8 | Δgag p17\URA3 | 658→707 | SEQ. ID. NO. 56 |
| ext short B int.11.12 | Δpol int\URA3 | 5216→5235 | SEQ. ID. NO. 57 |

TABLE 2-continued

Oligonucleotide primers for the insertion of HIV-1 coding regions into pREC NFL HIV-1 vectors in Table 1

| Primer Name | pREC-$_{NFL-HIV-1}$ Deletions | Location | Sequence |
|---|---|---|---|
| inter short B int.13 | Δpol int\URA3 | 5185→5204 | SEQ. ID. NO. 58 |
| inter short B int.14 | Δpol int\URA3 | 5154→5173 | SEQ. ID. NO. 59 |
| int short F int.7 | Δpol int\URA3 | 4171→4190 | SEQ. ID. NO. 60 |
| int short F int.8 | Δpol int\URA3 | 4148→4167 | SEQ. ID. NO. 61 |
| ext short F int.9 | Δpol int\URA3 | 4121→4140 | SEQ. ID. NO. 62 |
| ext short F int.10 | Δpol int\URA3 | 4071→4090 | SEQ. ID. NO. 63 |
| int short B Rnase.7.8 | Δpol rnase H\URA3 | 4282→4263 | SEQ. ID. NO. 64 |
| ext short B Rnase.9.10 | Δpol rnase H\URA3 | 4323→4305 | SEQ. ID. NO. 65 |
| int short F p7.7.8 | Δgag p7\URA3 | 1847→1865 | SEQ. ID. NO. 66 |
| ext short F p7.9.10 | Δgag p7\URA3 | 1804→1823 | SEQ. ID. NO. 67 |
| Int Fwd gp120.3 | Δenv gp120\URA3 | 6179→6198 | SEQ. ID. NO. 68 |
| Int Fwd gp120.4 | Δenv gp120\URA3 | 6146→6165 | SEQ. ID. NO. 69 |
| Ext Fwd gp120.5 | Δenv gp120\URA3 | 6092→6111 | SEQ. ID. NO. 70 |
| Ext Fwd gp120.6 | Δenv gp120\URA3 | 6068→6090 | SEQ. ID. NO. 71 |
| TAT Short FWD.1 | Δtat\URA3 | 5760→5782 | SEQ. ID. NO. 72 |
| TAT Short FWD.2 | Δtat\URA3 | 5733→5754 | SEQ. ID. NO. 73 |
| TAT Short FWD.3 | Δtat\URA3 | 5716→5737 | SEQ. ID. NO. 74 |
| TAT Short BWD.4 | Δtat\URA3 | 8474→8453 | SEQ. ID. NO. 75 |
| TAT Short BWD.5 | Δtat\URA3 | 8476→8455 | SEQ. ID. NO. 76 |
| TAT Short BWD.6 | Δtat\URA3 | 8485→8464 | SEQ. ID. NO. 77 |
| TAT Short BWD.7 | Δtat\URA3 | 8534→8513 | SEQ. ID. NO. 78 |
| TAT Short FWD.8 | Δtat\URA3 | 5491→5512 | SEQ. ID. NO. 79 |
| TAT Short FWD.9 | Δtat\URA3 | 5429→5450 | SEQ. ID. NO. 80 |
| EXT Short FWD.10 | Δtat\URA3 | 5411→5432 | SEQ. ID. NO. 81 |
| TAT Short BWD.11 | Δtat\URA3 | 8748→8727 | SEQ. ID. NO. 82 |
| TAT Short BWD.12 | Δtat\URA3 | 8688→8667 | SEQ. ID. NO. 83 |
| TAT Short BWD.13 | Δtat\URA3 | 8603→8582 | SEQ. ID. NO. 84 |
| POL RT Short FWD.7 | Δpol rt\URA3 | 2463→2484 | SEQ. ID. NO. 85 |
| POL RT Short FWD.8 | Δpol rt\URA3 | 2450→2471 | SEQ. ID. NO. 86 |
| POL PRO Short BWD.7 | Δpol prot\URA3 | 2640→2619 | SEQ. ID. NO. 87 |
| POL PRO Short BWD.8 | Δpol prot\URA3 | 2631→2610 | SEQ. ID. NO. 88 |
| VPR Short BWD.4 | Δvpr\URA3 | 5956→5935 | SEQ. ID. NO. 89 |
| VPR Short BWD.5 | Δvpr\URA3 | 5923→5902 | SEQ. ID. NO. 90 |
| VPR Short BWD.6 | Δvpr\URA3 | 5895→5874 | SEQ. ID. NO. 91 |
| GAG P17 Short FWD.7 | Δgag p17\URA3 | 671→692 | SEQ. ID. NO. 92 |
| GAG P17 Short FWD.8 | Δgag p17\URA3 | 660→681 | SEQ. ID. NO. 93 |

Degenerate Bases Key:
N = A + C + G + T
V = A + C + G V
D = A + T + G
B = T + C + G
H = A + T + C
W = A + T
S = C + G
K = T + G
M = A + C
Y = C + T
R = A + G The primary recombinant virus devoid of a 5' LTR may be used to efficiently obtain infectious virus with the aid of a complementation genome. As shown schematically in the inset box in FIG. 3, the complementation genome contains the R and U5 segments of the 5' LTR, the pbs and the RNA packaging (ψ) region of the HIV genome and may be carried by a second vector such as a plasmid. Isolates containing differing lengths of the HIV-1 genome but supplying the aforementioned segments of the 5'LTR are shown as cpltRU5gag/tag, cpltRU5gag2/tag, cpltRU5gag3/tag, and cplt_nflΔrbf RNA. The complementation genome may be under control of a CMV promoter as in the plasmid denoted as pCMV_cpltRU5gag/tag, or not under the control of such a promoter as in the plasmid pHIV-1 5'LTR. The sequence of pCMV_cpltRU5gag/tag is provided as SEQ. ID. No. 3. The sequence of pHIV-1 5'LTR is provided as SEQ. ID. No. 4.

As described above, the pREC$_{nfl\ HIV-1}$ will not transcribe HIV-1 RNA to support the production of infectious virus. To obtain infectious virus, the nfl HIV-1 RNA must be complemented by a shorter HIV-1 RNA template which contains (in 5' to 3' order) the U5-R regions of the LTR, the PBS, the uncoding HIV-1 sequence and part of the gag open reading frame (plasmid referred to as pCMV_cpltRU5gag). The latter two sequence elements contain the RNA packaging sequence (ψ). A stably transformed 293T cell line containing a vector expressing the cpltRU5gag RNA has been produced. When the cpltRU5gag RNA is packaged with a nfl HIV-1 RNA, the virus produced supports full reverse transcription and as a result, wild type virus production. This virus can then be used for numerous phenotypic assays described herein. Alternately, other constructs may be used to enhance packaging of a RU5gag RNA with nfl HIV-1 RNA.

Optionally, the complementation genome may further include portions or the entirety of the gag and pol genes of HIV-1. Mammalian cells such as 293T cells may be transformed with a vector containing the complementation genome and a vector containing the primary recombinant. A subset of the viral particles produced by the transformed cells will contain both the primary recombinant genome and the complementation genome. Other subsets of viral particles will contain only the primary recombinant genome or only the complementation genome and will not produce active infections. Viral particles containing a primary recombinant genome and a complementation genome are believed to be infectious because of template switching occurring during reverse transcription of the viral genome. Reverse transcription of viral genomic RNA begins at the pbs site, proceeds with reverse transcription through the U5 and R segments and then through template switching described above, reverse transcription will continue with the viral RNA that is complete with the exception of the 5' LTR. Cells infected in this way will produce viral particles containing full-length recombinant genomes. Such recombinant viruses may then be tested for their relative fitness in general, that is, their efficiency in infecting cells, as well as their susceptibility to various drug therapies.

Preliminary quantitations of the short and nfl HIV-1 RNA in the $293_{cpltRU5gag}$ cells transfected with the $pREC_{nfl\,HIV-1}$ vector and in the purified virus particles produced from these cells were performed. A delayed expression of the cpltRU5gag RNA, believed to be due to requirement of Tat transactivation, i.e. produced from transcribed $pREC_{nfl\,HIV-1}$, was found. As a result, the virus produced early after $pREC_{nfl\,HIV-1}$ transfection was less infectious (homozygous for nfl RNA) than the more heterozygous virus produced later on. Stable 293T cells expressing cpltRU5gag RNA ($293_{cpltRU5gag}$ cells) producing Tat under the control of tetracycline and the TetON system (Clontech) have been produced. Upon $pREC_{nfl\,HIV-1}$ transient transfection, the virus produced from tetracycline treated $293_{cpltRU5gag}$(+Tat) cells is approximately 100-fold more infectious than that produced from $293_{cpltRU5gag}$.

Figure 3:
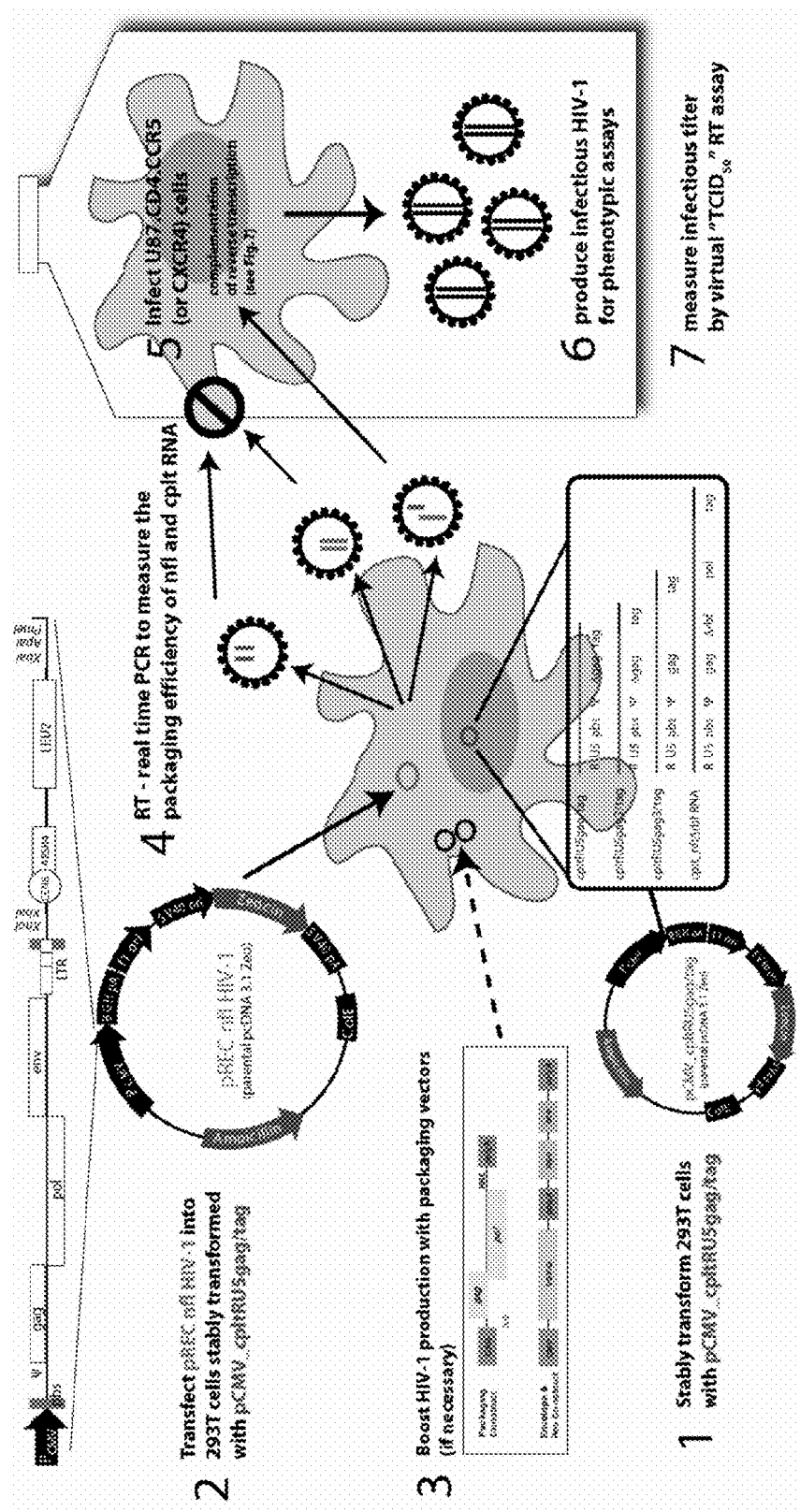
FIG. 3 is a representation of the use of the vectors of the present invention to produce infectious retroviral particles.

Alternate strategies may be used for the production of this deleted HIV-1 RNA for the complementation of nfl HIV-1 RNA to produce infectious viruses. First, the length of the shorter RNA template may be extended to the end of gag without interfering with the patient pol-env amplicon in the nfl RNA (FIG. 3). The marker in this case would be a destroyed frameshift site at the gag-pol gene interface. HIV-1 has −1 ribosomal frameshift that ensures 50-fold higher levels of gag precursor proteins are translated than the gag-pol precursor. Mutations could be generated in this complementation RNA vector to delete the gag stop codon, delete the stem-loop responsible for the −1 ribosomal frameshift, and finally, delete a short sequence in pol such that a premature stop codon would be introduced. The RNA from this vector would be referred to as cplt_nflΔrbf RNA). Non-infectious virus particle production would result from an infection with a virus particle containing the nfl HIV-1 RNA and the cplt_nflΔrbf RNA but only if template switching of the elongating (−) strand DNA occurred from the nfl HIV-1 RNA to the cplt_nflΔrbf RNA in the patient pol-env region.

When the complementing RNA is co-packaged with HIV-1 nfl RNA into virus particles, this heterozygous virus may be infectious for a susceptible cell. As shown in FIG. 3, HIV (−) strong stop DNA is initiated from the complementing RNA and then jumps to the R region on the 3' end of nfl RNA. A second strand switch involving the pbs as a complementary sequence would then permit synthesis of a complete HIV-1 DNA genome for integration. This process would be analogous to the intrastrand model of retroviral reverse transcription. Assuming Hardy-Weinberg equilibrium ($x^2+y^2+2xy$) and that packaging of both RNAs are equal, then one half of the virus should be infectious ($2xy$) whereas the other half would contain either two copies of the complementing RNA or the nfl RNA ($x^2$ or $y^2$).

The recombinants may be utilized in a method for creating an integrated HIV-1 phenotypic/genotypic system for patient management and care. Currently, there are a number of companies that provide HIV-1 drug resistance genotypes and two biotechnology firms that offer phenotypic drug resistance tests. Phenotypic assays are very expensive (~$1000/assay) and have the potential to double or triple if new classes of ARV are FDA approved. The high costs are related to a labor intensive cloning methods to introduce the PR-RT, env, and IN amplicons into separate HIV-1 vectors. In contrast, this HIV-1 cloning method provided is based on yeast recombination/gap repair which is highly efficient, less labor intensive, and more reliable. This vector can recombine a number of targets within the HIV-1 genome, including a large PR-RT-IN (pol)-env amplicon, which represents all of the drug targeted genes of HIV-1 (both FDA approved ARVs and new classes of inhibitors currently being tested). The HIV-1 vector which accepts the patient pol-env or other amplicon may also contain a firefly luciferase gene or other fluorescent protein, which is then used in tri-infections with two laboratory control strains (i.e. HIV-1 NL4-3 and an NL4-3/BaL env chimera) containing two other biomarker genes (i.e. renilla luciferase and green fluorescent protein, respectively). This tri-infection in the absence or presence of increasing concentrations of ARVs will provide concurrent, internally controlled measures of drug resistance, fitness, and biological phenotype (e.g. CXCR4 vs. CCR5 co-receptor usage).

The phenotypic assays may be combined with a new genotypic drug resistance approach. The assays allow the rapid quantification of low levels of drug resistant mutations found in the HIV-1 population within an infected patient. HIV-1 exists as a swarm of clones (or quasispecies) in an HIV-1 infected patient. Single mutations for resistance to a drug pre-exist in a quasispecies even prior to treatment. These single mutations typically dominate the intrapatient HIV-1 population in cases of drug failure and resistance. Virus clones containing these drug resistant mutations fade in the quasispecies following cessation of treatment with that ARV. Nonetheless, they remain an obstacle to the success of any HAART regimen containing that ARV since the drug resistant mutations are found at higher percentages in the quasispecies than in drug naïve patients. A multiplexed oligonucleotide ligation assay (OLA) can quantify the level of specific drug resistant mutations in a quasispecies (as low as 0.1%). This OLA will employ the same amplicon used for the phenotypic assays and the sequencing analyses. A measure of drug resistant mutations in the patient HIV-1 quasispecies is now gaining attention as a clinical tool for monitoring treatment success as well as in choosing the appropriate HAART regimen.

Figure 4:
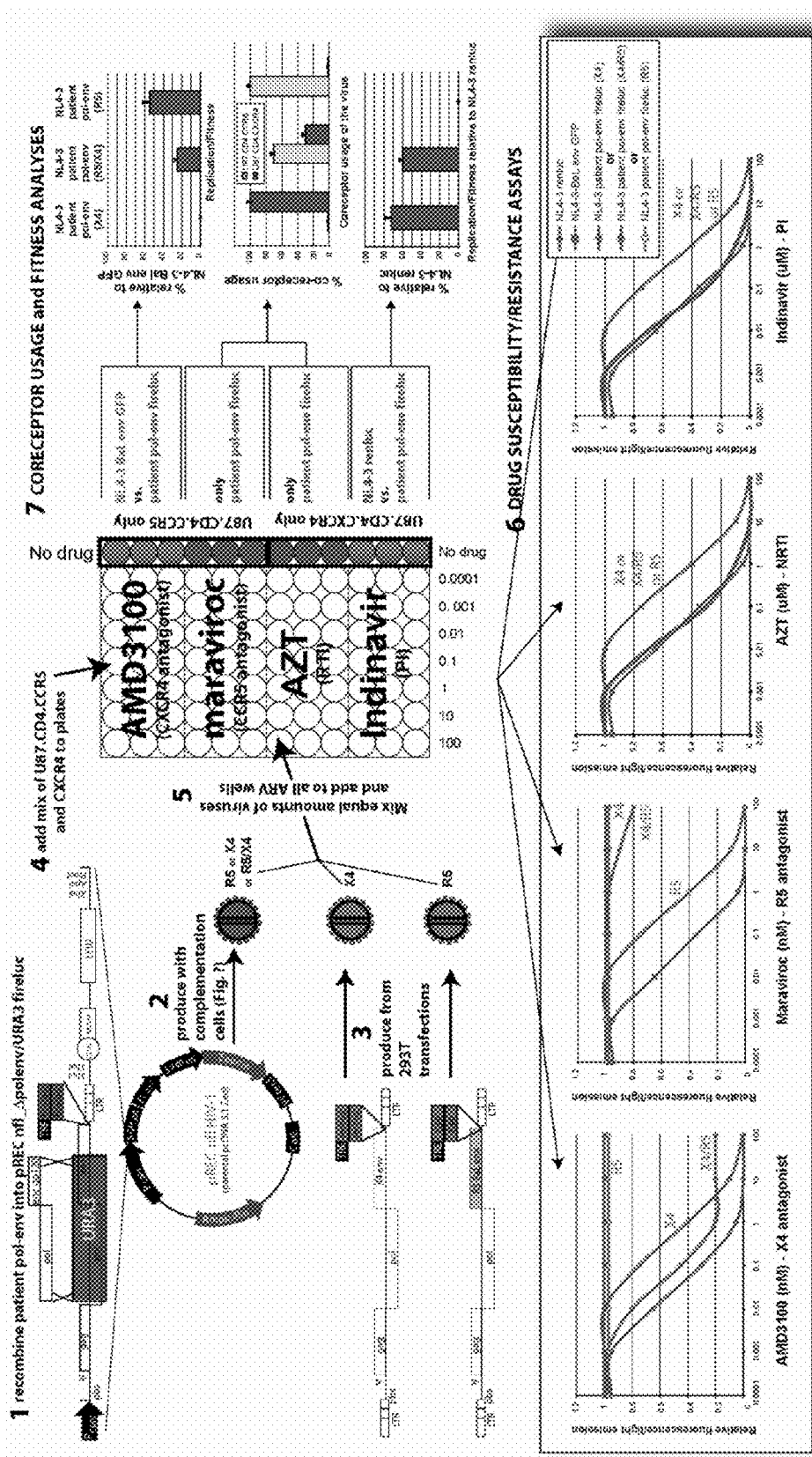
FIG. 4 is a schematic view of a drug susceptibility/resistance assay according to the present inv vector sequence is from pREC env. The sequences are arranged in the PCR primers such that vector sequence flanks the HIV-1 sequence in the resulting PCR product. These primers permit a two step introduction of the near full length (nfl) HIV-1 genome just upstream of the CMV promoter.

In contrast to other prior assays, the assay may employ a fluorescent color system for the drug susceptibility and fitness assays. This may require separately cloning identifiable markers such as the renilla (ren) and firefly (fire) luciferase (luc) genes, red fluorescent protein (dsRED), click beetle green luciferase (CBG), click beetle red luciferase (CBR) and/or the enhanced green fluorescent protein (eGFP) gene into a near full length HIV-1 isolate, either containing or not containing a selectable marker substituted into a region of the HIV-1 genome by yeast recombination as described above. For example, as shown in FIG. 4, insertion of a firefly luciferase (fireluc) gene into $pREC_{nfl\ HIV-1}$ pol-env/URA3 between the HIV-1 env and nef genes results in $pREC_{nfl\ HIV-1\ fireluc}$ pol-env/URA3. Insertion of renilla luciferase (renluc) into a vector carrying the NL4-3 genome between the env and nef genes results in $pREC_{nfl\ HIV-1\ renluc}$ pol-env/URA3. Finally, insertion of EGFP into a hybrid genome of NL4-3/Bal produces $pREC_{nfl\ HIV-1\ EGFP}$ pol-env/URA3. The latter two constructs act as controls in the following system.

Replacing the NL4-3 env gene (CXCR4-utilizing) in the vector pNL4-3 with the env gene of HIV-1 BaL (CCR5-utilizing) (referred to as pNL4-3_BaL env) produces NL4-3_BaL env virus, which utilizes the CCR5 receptor for entry and only infects the U87.CD4.CCR5 cells whereas the NL4-3 only infects U87.CD4.CXCR4 cells. Inducible and constitutively active promoters may drive luciferase/EGFP expression in these constructs. For example, a fluorescent protein gene may be placed under the control of the TetOn responsive element (TRE). As also shown in FIG. 4, the fluorescent protein gene may be inserted in either a forward or reverse orientation. Currently, each of the fluorescent protein genes for renluc, fireluc, dsRED, CBG, CBR and eGFP have been inserted into the vectors listed in Table 1, between the env and nef genes. Additionally, renluc, CBG and CBR have been inserted into pREC nfl HIV-1 plasmids. The sequence of pREC nfl HIV-1-renluc is provided as SEQ. ID. NO. 5. The sequence of pREC nfl HIV-1-renluc is provided as SEQ. ID. NO. 5. The sequence of pREC nfl HIV-1-CBG is provided as SEQ. ID. NO. 6. The sequence of pREC nfl HIV-1-CBR is provided as SEQ. ID. NO. 7. These latter plasmids may be subjected to homologous recombination in yeast to replace parts of the HIV-1 genome as provided above. It should be noted also, that in these sequences, the Bam HI restriction endonuclease site at residue 1 corresponds to the BamHI site at residue 7833 of pREC-nfl HIV-1, with the inserted sequence encoding a fluorescent protein being located downstream of the BamHI site, beginning at residue 334. For SEQ. ID. NO. 5, renluc is located between residues 334 and 1269. For SEQ. ID. NO. 6, CBG is located between residues 334 and 1962. For SEQ. ID. NO. 7, CBR is located between residues 334 and 1962.

The actual phenotypic drug sensitivity/fitness assays on the patient-derived pol-env HIV-1 fireluc may be performed by adding this virus or the two control viruses (HIV-$1_{NL4-3}$ ren luc and HIV-$1_{NL4-3-Bal\ env}$ EGFP) into 96 well plates containing U87 cells created to express CD4 plus CXCR4 mixed with U87 cells created to express CD4 and CCR5. Since EGFP, firefly luciferase, and renilla luciferase emit different wavelengths of fluorescence/light, one can compare the production of the patient-derived pol-env HIV-1 isolate to that of two control strains and calculate a relative fitness value, all in the same well. These dual infections may also be performed in 96 well plates in the presence of all ARVs (in triplicate with eight wells containing 10-fold increasing drug concentrations). Unlike prior assays, the present invention can monitor drug sensitivity in terms of IC50 and IC90 values (concentrations for 50 and 90% inhibition) of the patient-derived virus and control strain in the same well due to the distinct spectrum from three luminescent proteins. This will prevent any inter-assay variations and even provide fitness analyses in the presence of drugs.

Figure 5:
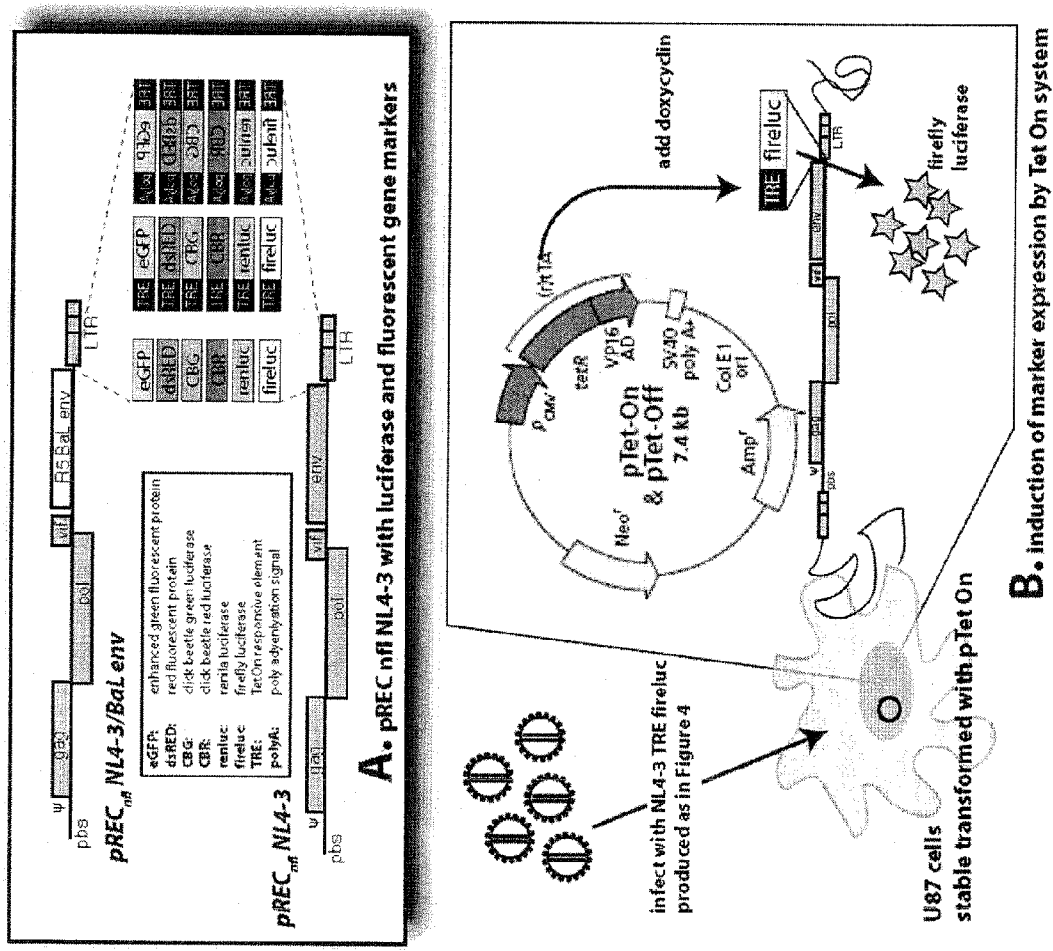

As mentioned above, an alternative variation may employ an inducible expression system such as the Tet-On transcription control system from ClonTech, as represented in FIG. 5. Briefly, the TRE (tet responsive element) is linked to a minimal CMV promoter upstream of a fluorescent protein gene such as ren or fire luc genes and then cloned between env and nef. rTetR would be expressed in the U87.CD4.CCR5 (or CXCR4) target cells where it would bind to the TRE and drives transcription only in the presence of doxycyclin. The Tet-On system has advantages over the Tet-Off system for this vector because TRE would not be occupied by the rTetR in absence of doxycyclin and as a result, transcription initiated from the LTR could read through this element and hopefully, not block normal transcription/translation of viral RNA/proteins. When virus measurements are needed, luciferase expression can be turned on with 1 ug/ml of doxycyclin at days 3-4 post infection. It is important to note that the addition of these fragments into the HIV-1 genome could disrupt numerous processes and reduce infectious potential. It is possible that these luc inserts may further decrease replication efficiency or result in a defective/dead virus. In the latter case, the luc genes may be introduced in place of nef. Previous studies have shown HIV-1 can replicate when the nef gene (prior to overlapping segment with the U3 region) is deleted or replaced with an exogenous gene. It is also envisioned that the TRE-luc or TRE-GFP genetic elements may be placed in the opposite orientation, i.e. in opposite direction of HIV-1 transcription.

An example of the assay system is represented in FIG. 4. A patient derived pol env gp120 fragment is recombined into a nfl HIV-1 isolate containing a fireluc gene as described above. A renluc containing NL4-3 isolate and a CBR-containing NL4-3/BaL env isolate act as the controls. Each isolate is transfected into 293T cells separately containing the complementation genome. Viable viral particles are produced from each strain and may be quantified by a virtual $TCID_{50}$ assay. The virtual $TCID_{50}$ assay was developed following the observation that the endogenous reverse transcriptase activity in a virus particle was strong correlate of infectious titer (measured by standard $TCID_{50}$ assays). The virtual $TCID_{50}$ assays take about 5 hrs to complete or about $\frac{1}{100}$ the time of a standard TCID50 assay. The viral particles are then added to U87.CD4.CXCR4 or U87.CD4.CCR5 cells. Luciferase activity and EGFP fluorescent levels will be measured over time (3 days to 12 days).

The standard protocol for drug sensitivity assays includes adding one or more ARV at various dilutions into plate wells prior to the addition of cells (2 h incubation) and then the three viruses (two control and one patient-derived). Since the assay measures virus production (or luciferase activity) as a correlate of luc mRNA expression/protein translation originating from integrated HIV-1 DNA, the original virus inoculums can remain in the well. If the Tet-On system is used to drive luciferase/EGFP expression, doxycyclin is added at day 3. With or without the Tet-on system, cells may be lysed at 4-5 days using commercially available Luciferase Assays and read on a plate reader.

Because the control NL4-3 ren luc and NL4-3_BaL env CBR viruses have different env sequences, they infect different U87.CD4 cells in the mixture (CXCR4 or CCR5, respectively). The NL4-3_BaL env CBR will be inhibited by increasing concentrations of the CCR5 antagonist drugs and thus, EGFP signal will be reduced. However, the NL4-3 ren luc will not be inhibited by increasing concentrations of the CCR5 antagonist drugs.

If the patient-derived HIV-1 $_{NL4-3\_patient\ pol-env}$ fire luc is CCR5 tropic, it will be inhibited in a dose-dependent manner by the CCR5 antagonistic resulting in a loss in firefly luciferase signal. If the patient derived virus is CXCR4 tropic, the signal would not diminish with all CCR5-antagonist concentrations. The opposite of the latter and former scenarios would result in testing sensitivity to a CXCR4 antagonist. Finally, dual tropism could result in a drug sensitivity curve suggesting the lack of complete virus inhibition even at the highest CCR5 antagonist or CXCR4 antagonist concentrations. Alternatively, a dominance of the CXCR4 phenotype (as suggested by preliminary data) would result in a lack of inhibition by CCR5 inhibitors. In all likelihood, a resistant CCR5-antagonist phenotype would be recorded with CXCR4-tropic HIV-1 $_{NL4-3\_patient\ pol-env}$ or with most dual tropic viruses. In contrast, there will likely be some low level infections of U87.CD4.CCR5 cells by dual tropic HIV-1 $_{NL4-3\_patient\ pol-env}$ in the presence of CXCR4 antagonists.

The basic principle of this integrated/comprehensive drug sensitivity assay will be to examine the $IC_{50}$ values for multiple ARVs including entry inhibitors and to establish simultaneous reference values with the two control viruses.

All PIs, NRTIs, NNRTIs and INIs inhibit HIV-1 regardless of co-receptor usage. Since the NL4-3 ren luc and NL4-3_BaL env EGFP viruses both have the same gag-pol genes (i.e. NL4-3), the drug sensitivity of these two viruses to all ARVs (except X4 and R5 antagonists) are the same in both cell lines (.CXCR4 or .CCR5, respectively). When testing sensitivity to T20/Fuseon, the NL4-3 ren luc is intrinsically-resistant whereas NL4-3_BaL env EGFP is sensitive to the drug.

Drug sensitivity and IC50/IC90 values are measured by drug dose-dependent inhibition from a maximal virus production. Fitness examines the relative production of each control virus and patient-derived virus in the absence and the presence of drugs. Ex vivo HIV-1 fitness has an impact on disease progression. In addition, patient-derived viruses treated with ARVs or that become resistant to these drugs have a reduced replicative fitness (in the absence of ARVs). In the presence of ARVs, it is obvious that ARV-resistant virus have selected advantage over the drug sensitive virus. Recent studies have suggested that even ARV-resistant viruses cannot achieve maximal replication rates (or comparable to "wild type" viruses in the absence of drugs) because the drug resistant mutations are associated with a fitness cost. In cases where patients harbor multi-drug resistant viruses to all ARVs, there may be an advantage of maintaining the drug resistant mutations in the virus with drug selective pressure (i.e. keep the patient on treatment) because the virus may be debilitated.

Prior assays have established a replicative capacity (RC) value to report back to patients/physicians. However, this RC value is limited to the impact of the PR-RT gene on HIV-1 fitness. In addition, the sensitivity and dynamic range of this assay is limited because the patient derived PR-RT virus is not directly competed with the control virus (NL4-3) in a multiple cycle infection. Furthermore, the prior RC assay is a monoassay where there is no internal control, whereas the present invention's fitness assay involves 2 viruses that compete head-to-head to determine which is more fit. Instead, all control NL4-3 and patient-derived virus replications rates are obtained from separate single-cycle infections. Fitness will be measured relative HIV-1$_{NL4-3}$ ren luc production if the patient derived virus is dual tropic or CXCR4-tropic. The maximal levels of EGFP, ren luc, and fire luc activity is based on mono-infections with these viruses.

Figure 6:
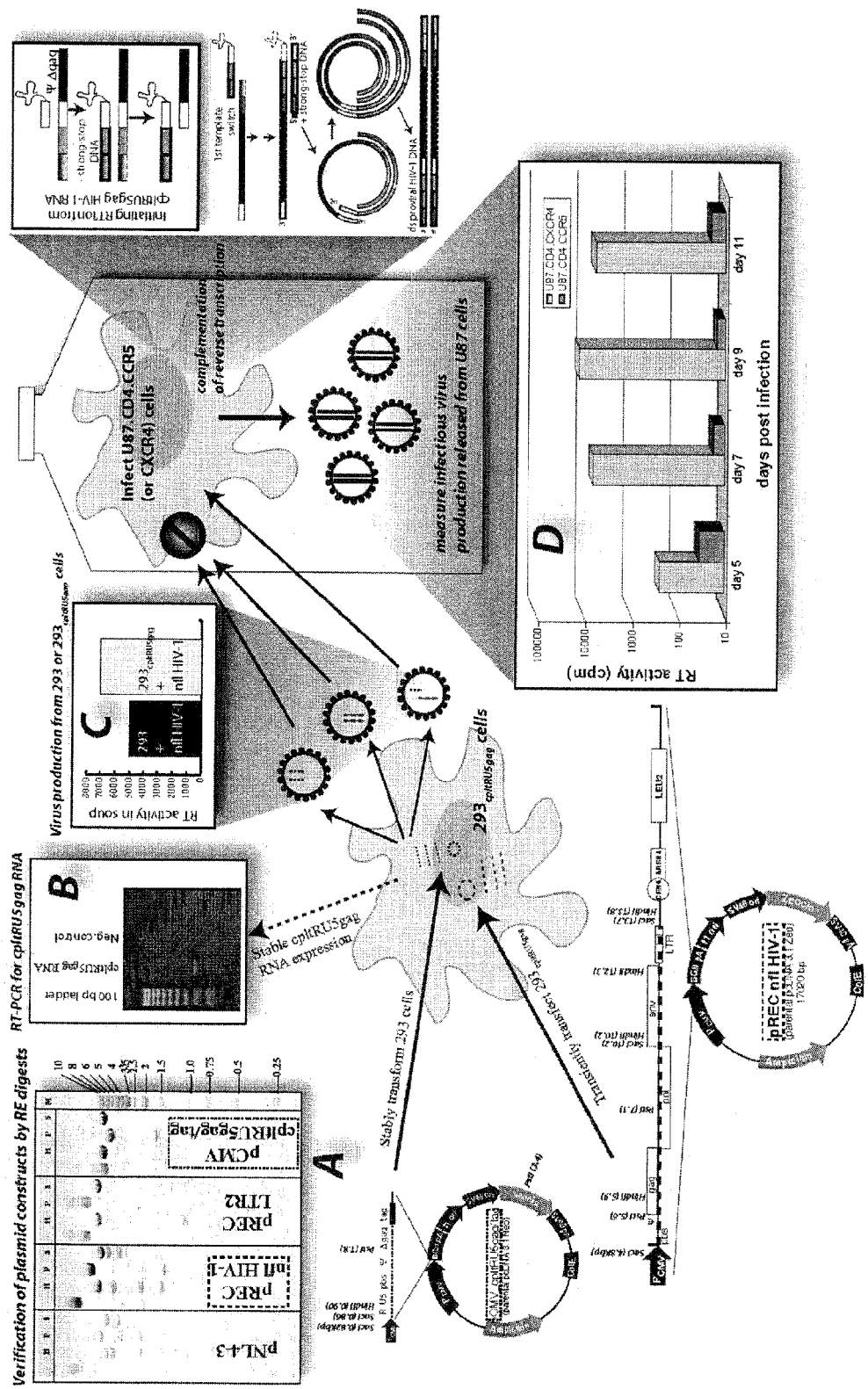

FIG. 6 illustrates the assay system in practice. Panel A shows a HindIII, PstI, and SacI restriction enzyme map of pNL4-3, pREC nfl HIV-1, pREC-LTR2, and pCMV_cpl-tRU5/tag. Bands correspond with all the predicted cut sites in the plasmid maps. The nfl HIV-1 RNA, transcribed from pREC nfl HIV-1 could then be complemented in 293 cells stably transformed with pCMV_cpltRU5gag/tag (293 cpltRU5gag). The transcribed cpltRU5gag/Tag RNA was easily RT-PCR amplified from the 293 cpltRU5gag cells (Panel B). Upon transfection with pREC nfl HIV-1, virus is produced from 293 or 293 cpltRU5gag cells (Panel C). However, only virus produced from pREC nfl HIV-1 transfected 293 cpltRU5gag cells could infect U87.CD4.CXCR4 cells and not U87.CD4.CCR5 cells (Panel D). This demonstrates that a 5'LTR-deleted HIV-1 RNA genome can be complemented during reverse transcription with a small HIV-1 RNA that gets co-packaged and that can act as template for (−) strand strong stop DNA synthesis. The production of replication competent virus following this complementation was remarkably robust.

Organisms other than yeast may also be utilized to provide homologous recombination. For example, the bacterial strains TB10-pyrF287 and TB10ΔpyrF can also be used for recombination of PCR fragments into the pREC nfl HIV-1 plasmids. TB10ΔpyrF strain genotype is nad::Tn10/pλ-Δcro-bro tetr pyrF. TB10ΔpyrF287 strain genotype is nad::Tn10/pλ-Δcro-bro tetr pyrF287. Both strains were derived from TB10 from Tom Bernhardt and Pete DeBoer. These strains express λ bet, gam, and exo for hyper-recombination. Additionally, pyrF is the homolog to URA3. We have deleted and mutated pyrF in TB10-pyrF287 and TB10λpyrF to allow URA3 plasmids to be used for selection. This will allow the same plasmids to be currently used in the yeast system to be used in the bacterial system.

Figure 7:
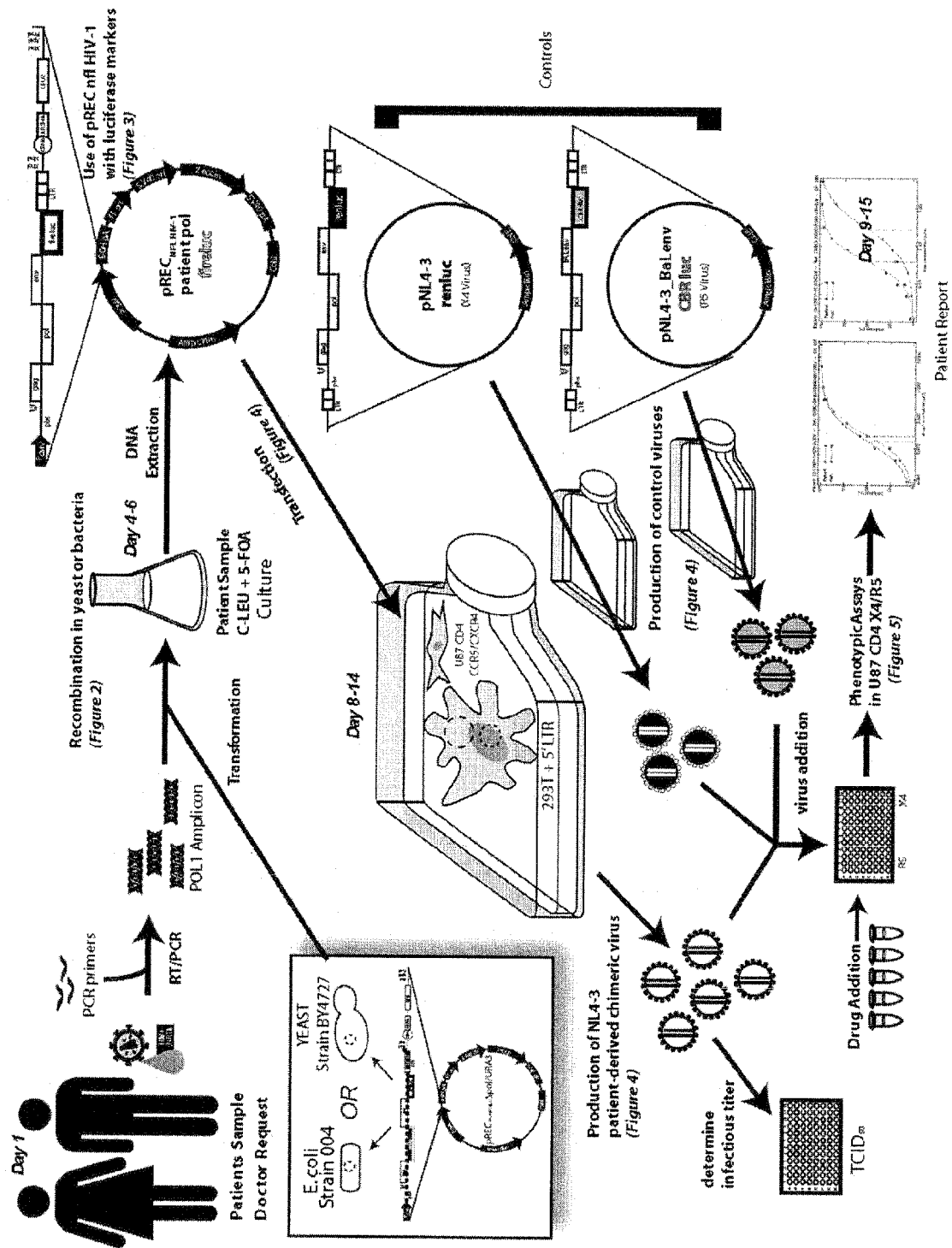

Based upon the foregoing disclosure, it should now be apparent that the vectors provided herein will provide a method of screening HIV-1 drug sensitivity. A representation of the method is provided as FIG. 7. It is, therefore, to be understood that any variations evident fall within the scope of the claimed invention and thus, the selection of specific component elements can be determined without departing from the spirit of the invention herein disclosed and described.

What is claimed is:

1. A method of amplifying at least a portion of a retroviral genome, the method comprising:
providing a first vector comprising at least one origin of replication, a sequence substantially identical to the primer binding site of a retrovirus and a sequence that is substantially identical to the U5 sequence of the 3' long terminal repeat sequence of the retrovirus, and a selectable marker, wherein the first vector is devoid of the R and U5 sequences of the 5' long terminal repeat region of a retrovirus;
providing a retroviral sequence isolated from a patient wherein said sequence isolated from a patient is modified to comprise sequence substantially identical to at least a portion of the selectable marker;
transforming a cell line with the first vector and the retroviral sequence, either sequentially or concurrently;
selecting against the presence of the selectable marker to provide a transformed cell line having a second vector, wherein the selectable marker of the first vector has been replaced by the retroviral sequence;
transforming a second cell line with the second vector and a third vector, wherein the third vector comprises a retroviral sequence substantially identical to the R and U5 sequences of the 5' long terminal repeat region of a retrovirus, to provide a transformed second cell line;
isolating viable retrovirus particles from the transformed second cell line.

2. The method of claim 1, wherein the first vector additionally comprises a sequence encoding a first biomarker protein.

3. The method of claim 2, wherein the first biomarker protein is selected from the group consisting of renilla luciferase, firefly luciferase, red fluorescent protein, click beetle green luciferase, click beetle red luciferase and enhanced green fluorescent protein.

4. The method of claim 3, additionally comprising contacting a third cell line with the viable retroviral particles isolated from the transformed second cell line in the presence of one or more antiviral particles and optionally additionally comprising contacting the third cell line with a first control vector comprising a sequence of a first control HIV-1 strain and a sequence encoding a second biomarker protein selected from the group consisting of renilla luciferase, firefly luciferase, red fluorescent protein, click beetle green luciferase, click beetle red luciferase and enhanced green fluorescent protein, and wherein the first and second biomarker proteins are different.

5. The method of claim 4, comprising the optional step of contacting the third cell line with a first control vector and additionally comprising contacting the third cell line with a second control vector comprising a sequence of a second control HIV-1 strain and a sequence encoding a third biomarker protein selected from the group consisting of renilla luciferase, firefly luciferase, red fluorescent protein, click beetle green luciferase, click beetle red luciferase and enhanced green fluorescent protein, and wherein the first, second and third biomarker proteins are different.

6. The method of claim 3, wherein the wherein the first vector comprises a sequence selected from the group consisting of SEQ. ID. NO. 5, SEQ. ID. NO. 6, and SEQ. ID. NO. 7.

7. The method of claim 1, wherein the at least one origin of replication is selected from a bacterial origin of replication and a yeast origin of replication.

8. A kit for performing the method of claim 1, comprising a first vector that includes at least one origin of replication, a sequence substantially identical to the primer binding site of a retroviral strain, a sequence that is substantially identical to the U5 sequence of the 3' long terminal repeat sequence of the retrovirus, and a selectable marker, wherein the first vector is devoid of the R and U5 sequences of the 5' long terminal repeat region of the retrovirus.

\* \* \* \* \*

UNITED STATES PATENT AND TRADEMARK OFFICE
CERTIFICATE OF CORRECTION

PATENT NO. : 8,586,295 B2  
APPLICATION NO. : 12/279039  
DATED : November 19, 2013  
INVENTOR(S) : Eric J. Arts Page 1 of 1

It is certified that error appears in the above-identified patent and that said Letters Patent is hereby corrected as shown below:

In the Specification

Column 8; Line 56: delete "Δvpi\URA3" and insert --Δvpu\URA3--.

Column 9; Line 14: delete "int BRnase.8" and insert --int B Rnase.8--.

Column 16; Line 47: delete "TCID50" and insert --$TCID_{50}$--.

Column 18; Line 21: delete "293 cpltRU5gag" and insert --$293_{cpltRU5gag}$--.

Column 18; Line 23: delete "293 cpltRU5gag cells" and insert --$293_{cpltRU5gag}$ cells--.

Column 18; Line 25: delete "293 cpltRU5gag cells (Panel C)" and insert --$293_{cpltRU5gag}$ cells (Panel C)--.

Column 18; Line 27: delete "293 cpltRU5gag cells" and insert --$293_{cpltRU5gag}$ cells--.

In the Claims

Column 147; Line 25: please add claim 9 as shown:

9. A nucleic acid comprising the sequence of SEQ. ID. NO. 1.

Signed and Sealed this  
Eighteenth Day of November, 2014

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,586,295 B2 | Page 1 of 1 |
| APPLICATION NO. | : 12/279039 | |
| DATED | : November 19, 2013 | |
| INVENTOR(S) | : Arts | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1009 days.

Signed and Sealed this
Twenty-first Day of April, 2015

Michelle K. Lee
*Director of the United States Patent and Trademark Office*

SEQUENCE LISTING

<160> NUMBER OF SEQ ID NOS: 94

<210> SEQ ID NO 1
<211> LENGTH: 17020
<212> TYPE: DNA
<213> ORGANISM: Artificial Sequence
<220> FEATURE:
<223> OTHER INFORMATION: Plasmid sequence containing HIV-1, E-coli, and yeast sequences

<400> SEQUENCE: 1

| | | | | | |
|---|---|---|---|---|---|
| agtggcgccc | gaacagggac | ttgaaagcga | aagtaaagcc | agaggagatc | tctcgacgca | 60 |
| ggactcggct | tgctgaagcg | cgcacggcaa | gaggcgaggg | gcggcgactg | gtgagtacgc | 120 |
| caaaaatttt | gactagcgga | ggctagaagg | agagagatgg | gtgcgagagc | gtcggtatta | 180 |
| agcgggggag | aattagataa | atgggaaaaa | attcggttaa | ggccaggggg | aaagaaacaa | 240 |
| tataaactaa | aacatatagt | atgggcaagc | agggagctag | aacgattcgc | agttaatcct | 300 |
| ggccttttag | agacatcaga | aggctgtaga | caaatactgg | gacagctaca | accatccctt | 360 |
| cagacaggat | cagaagaact | tagatcatta | tataatacaa | tagcagtcct | ctattgtgtg | 420 |
| catcaaagga | tagatgtaaa | agacaccaag | gaagccttag | ataagataga | ggaagagcaa | 480 |
| aacaaaagta | agaaaaaggc | acagcaagca | gcagctgaca | caggaaacaa | cagccaggtc | 540 |
| agccaaaatt | accctatagt | gcagaacctc | caggggcaaa | tggtacatca | ggccatatca | 600 |
| cctagaactt | taaatgcatg | ggtaaaagta | gtagaagaga | aggctttcag | cccagaagta | 660 |
| atacccatgt | tttcagcatt | atcagaagga | gccaccccac | aagatttaaa | taccatgcta | 720 |
| aacacagtgg | ggggacatca | agcagccatg | caaatgttaa | aagagaccat | caatgaggaa | 780 |
| gctgcagaat | gggatagatt | gcatccagtg | catgcagggc | ctattgcacc | aggccagatg | 840 |
| agagaaccaa | ggggaagtga | catagcagga | actactagta | cccttcagga | acaaatagga | 900 |
| tggatgacac | ataatccacc | tatcccagta | ggagaaatct | ataaaagatg | gataatcctg | 960 |
| ggattaaata | aaatagtaag | aatgtatagc | cctaccagca | ttctggacat | aagacaagga | 1020 |
| ccaaaggaac | cctttagaga | ctatgtagac | cgattctata | aaactctaag | agccgagcaa | 1080 |
| gcttcacaag | aggtaaaaaa | ttggatgaca | gaaaccttgt | tggtccaaaa | tgcgaaccca | 1140 |
| gattgtaaga | ctatttaaa | agcattggga | ccaggagcga | cactagaaga | aatgatgaca | 1200 |
| gcatgtcagg | gagtgggggg | acccggccat | aaagcaagag | ttttggctga | agcaatgagc | 1260 |
| caagtaacaa | atccagctac | cataatgata | cagaaaggca | attttaggaa | ccaaagaaag | 1320 |
| actgttaagt | gtttcaattg | tggcaaagaa | gggcacatag | ccaaaaattg | cagggcccct | 1380 |
| aggaaaaagg | gctgttggaa | atgtggaaag | gaaggacacc | aaatgaaaga | ttgtactgag | 1440 |
| agacaggcta | attttttagg | gaagatctgg | ccttcccaca | agggaaggcc | agggaatttt | 1500 |
| cttcagagca | gaccagagcc | aacagcccca | ccagaagaga | gcttcaggtt | tggggaagag | 1560 |
| acaacaactc | cctctcagaa | gcaggagccg | atagacaagg | aactgtatcc | tttagcttcc | 1620 |
| ctcagatcac | tctttggcag | cgaccctctc | gtcacaataaa | gataggggg | caattaaagg | 1680 |
| aagctctatt | agatacagga | gcagatgata | cagtattaga | agaaatgaat | ttgccaggaa | 1740 |
| gatggaaacc | aaaaatgata | gggggaattg | gaggttttat | caaagtagga | cagtatgatc | 1800 |
| agatactcat | agaaatctgc | ggacataaag | ctataggtac | agtattagta | ggacctacac | 1860 |
| ctgtcaacat | aattggaaga | aatctgttga | ctcagattgg | ctgcacttta | aattttccca | 1920 |
| ttagtcctat | tgagactgta | ccagtaaaat | taaagccagg | aatggatggc | ccaaaagtta | 1980 |
| aacaatggcc | attgacagaa | gaaaaaataa | aagcattagt | agaaatttgt | acagaaatgg | 2040 |
| aaaaggaagg | aaaaatttca | aaaattgggc | ctgaaaatcc | atacaatact | ccagtatttg | 2100 |
| ccataaagaa | aaaagacagt | actaaatgga | gaaaattagt | agatttcaga | gaacttaata | 2160 |
| agagaactca | agatttctgg | gaagttcaat | taggaatacc | acatcctgca | gggttaaaac | 2220 |

```
agaaaaaatc agtaacagta ctggatgtgg gcgatgcata tttttcagtt cccttagata    2280
aagacttcag gaagtatact gcatttacca tacctagtat aaacaatgag acaccaggga    2340
ttagatatca gtacaatgtg cttccacagg gatggaaagg atcaccagca atattccagt    2400
gtagcatgac aaaaatctta gagcctttta gaaaacaaaa tccagacata gtcatctatc    2460
aatacatgga tgatttgtat gtaggatctg acttagaaat agggcagcat agaacaaaaa    2520
tagaggaact gagacaacat ctgttgaggt ggggatttac caccagac aaaaaacatc      2580 agaaagaacc tccattcctt tggatgggtt atgaactcca tcctgataaa tggacagtac    2640
agcctatagt gctgccagaa aaggacagct ggactgtcaa tgacatacag aaattagtgg    2700
gaaaattgaa ttgggcaagt cagatttatg cagggattaa agtaaggcaa ttatgtaaac    2760
ttcttagggg aaccaaagca ctaacagaag tagtaccact aacagaagaa gcagagctag    2820
aactggcaga aaacagggag attctaaaag aaccggtaca tggagtgtat tatgacccat    2880
caaaagactt aatagcagaa atacagaagc aggggcaagg ccaatggaca tatcaaattt    2940
atcaagagcc atttaaaaat ctgaaaacag gaaaatatgc aagaatgaag ggtgcccaca    3000
ctaatgatgt gaaacaatta acagaggcag tacaaaaaat agccacagaa agcatagtaa    3060
tatggggaaa gactcctaaa tttaaattac ccatacaaaa ggaaacatgg gaagcatggt    3120
ggacagagta ttggcaagcc acctggattc ctgagtggga gtttgtcaat acccctccct    3180
tagtgaagtt atggtaccag ttagagaaag aacccataat aggagcagaa actttctatg    3240
tagatggggc agccaatagg gaaactaaat taggaaaagc aggatatgta actgacagag    3300
gaagacaaaa agttgtcccc ctaacggaca caacaaatca gaagactgag ttacaagcaa    3360
ttcatctagc tttgcaggat tcgggattag aagtaaacat agtgacagac tcacaatatg    3420
cattgggaat cattcaagca caaccagata agagtgaatc agagttagtc agtcaaataa    3480
tagagcagtt aataaaaaag gaaaaagtct acctggcatg ggtaccagca cacaaaggaa    3540
ttggaggaaa tgaacaagta gatgggttgg tcagtgctgg aatcaggaaa gtactatttt    3600
tagatggaat agataaggcc caagaagaac atgagaaata tcacagtaat tggagagcaa    3660
tggctagtga ttttaaccta ccacctgtag tagcaaaaga aatagtagcc agctgtgata    3720
aatgtcagct aaaagggaa gccatgcatg gacaagtaga ctgtagccca ggaatatggc    3780
agctagattg tacacattta gaaggaaaag ttatcttggt agcagttcat gtagccagtg    3840
gatatataga agcagaagta attccagcag agacagggca agaaacagca tacttcctct    3900
taaaattagc aggaagatgg ccagtaaaaa cagtacatac agacaatggc agcaatttca    3960
ccagtactac agttaaggcc gcctgttggt gggcggggat caagcaggaa tttggcattc    4020
cctacaatcc ccaaagtcaa ggagtaatag aatctatgaa taaagaatta aagaaaatta    4080
taggacaggt aagagatcag gctgaacatc ttaagacagc agtacaaatg gcagtattca    4140
tccacaattt taaaagaaaa ggggggattg ggggtacag tgcaggggaa agaatagtag    4200
acataatagc aacagacata caaactaaag aattacaaaa acaaattaca aaattcaaa     4260 atttcgggt ttattacagg gacagcagag atccagtttg gaaaggacca gcaaagctcc     4320
tctggaaagg tgaaggggca gtagtaatac aagataatag tgacataaaa gtagtgccaa    4380
gaagaaaagc aaagatcatc agggattatg gaaaacagat ggcaggtgat gattgtgtgg    4440
caagtagaca ggatgaggat taacacatgg aaaagattag taaaacacca tatgtatatt    4500
tcaaggaaag ctaaggactg gttttataga catcactatg aaagtactaa tccaaaaata    4560
agttcagaag tacacatccc actaggggat gctaaattag taataacaac atattgggt    4620
```

```
ctgcatacag gagaaagaga ctggcatttg ggtcagggag tctccataga atggaggaaa    4680
aagagatata gcacacaagt agaccctgac ctagcagacc aactaattca tctgcactat    4740
tttgattgtt tttcagaatc tgctataaga aataccatat taggacgtat agttagtcct    4800
aggtgtgaat atcaagcagg acataacaag gtaggatctc tacagtactt ggcactagca    4860
gcattaataa aaccaaaaca gataaagcca cctttgccta gtgttaggaa actgacagag    4920
gacagatgga acaagcccca gaagaccaag ggccacagag ggagccatac aatgaatgga    4980
cactagagct tttagaggaa cttaagagtg aagctgttag acatttttcct aggatatggc    5040 tccataactt aggacaacat atctatgaaa cttacgggga tacttgggca ggagtggaag    5100
ccataataag aattctgcaa caactgctgt ttatccattt cagaattggg tgtcgacata    5160
gcagaatagg cgttactcga cagggagag caagaaatgg agccagtaga tcctagacta    5220
gagccctgga agcatccagg aagtcagcct aaaactgctt gtaccaattg ctattgtaaa    5280
aagtgttgct ttcattgcca agtttgtttc atgacaaaag ccttaggcat ctcctatggc    5340
aggaagaagc ggagacagcg acgaagagct catcagaaca gtcagactca tcaagcttct    5400
ctatcaaagc agtaagtagt acatgtaatg caacctataa tagtagcaat agtagcatta    5460
gtagtagcaa taataatagc aatagttgtg tggtccatag taatcataga atataggaaa    5520
atattaagac aaagaaaaat agacaggtta attgatagac aatagaaag agcagaagac    5580 agtggcaatg agagtgaagg agaagtatca gcacttgtgg gatgggggt ggaaatgggg    5640 caccatgctc cttgggatat tgatgatctg tagtgctaca gaaaaattgt gggtcacagt    5700
ctattatggg gtacctgtgt ggaaggaagc aaccaccact ctattttgtg catcagatgc    5760
taaagcatat gatacagagg tacataatgt ttgggccaca catgcctgtg tacccacaga    5820
ccccaaccca caagaagtag tattggtaaa tgtgacagaa aattttaaca tgtggaaaaa    5880
tgacatggta gaacagatgc atgaggatat aatcagttta tgggatcaaa gcctaaagcc    5940
atgtgtaaaa ttaaccccac tctgtgttag tttaaagtgc actgatttga agaatgatac    6000
taataccaat agtagtagcg ggagaatgat aatggagaaa ggagagataa aaaactgctc    6060
tttcaatatc agcacaagca taagagataa ggtgcagaaa gaatatgcat ctttttataa    6120
acttgatata gtaccaatag ataataccag ctataggttg ataagttgta acacctcagt    6180
cattacacag gcctgtccaa aggtatcctt tgagccaatt cccatacatt attgtgcccc    6240
ggctggtttt gcgattctaa aatgtaataa taagacgttc aatggaacag gaccatgtac    6300
aaatgtcagc acagtacaat gtacacatgg aatcaggcca gtagtatcaa ctcaactgct    6360
gttaaatggc agtctagcag aagaagatgt agtaattaga tctgccaatt tcacagacaa    6420
tgctaaaacc ataatagtac agctgaacac atctgtagaa attaattgta caagacccaa    6480
caacaataca agaaaaagta tccgtatcca gaggggacca gggagagcat tgttacaat    6540 aggaaaaata ggaaatatga acaagcaca ttgtaacatt agtagagcaa aatggaatgc    6600
cactttaaaa cagatagcta gcaaattaag agaacaattt ggaaataata aaacaataat    6660
ctttaagcaa tcctcaggag gggacccaga aattgtaacg cacagtttta attgtggagg    6720 ggaattttc tactgtaatt caacacaact gtttaatagt acttggttta atagtacttg    6780
gagtactgaa gggtcaaata cactgaagg aagtgacaca atcacactcc catgcagaat    6840
aaaacaattt ataaacatgt ggcaggaagt aggaaaagca atgtatgccc ctcccatcag    6900
tggacaaatt agatgttcat caaatattac tgggctgcta ttaacaagag atggtggtaa    6960
taacaacaat gggtccgaga tcttcagacc tggaggagcg gatatgaggg acaattggag    7020
```

```
aagtgaatta tataaatata aagtagtaaa aattgaacca ttaggagtag cacccaccaa    7080
ggcaaagaga agagtggtgc agagagaaaa aagagcagtg ggaataggag ctttgttcct    7140
tgggttcttg ggagcagcag gaagcactat gggctgcacg tcaatgacgc tgacggtaca    7200
ggccagacaa ttattgtctg atatagtgca gcagcagaac aatttgctga ggctattga     7260 ggcgcaacag catctgttgc aactcacagt ctggggcatc aaacagctcc aggcaagaat    7320
cctggctgtg gaaagatacc taaggatca acagctcctg gggatttggg gttgctctgg     7380
aaaactcatt tgcaccactg ctgtgccttg gaatgctagt tggagtaata atctctgga     7440 acagatttgg aataacatga cctggatgga gtgggacaga gaaattaaca attacacaag    7500
cttaatacac tccttaattg aagaatcgca aaaccagcaa gaaaagaatg aacaagaatt    7560
attggaatta gataaatggg caagtttgtg gaattggttt aacataacaa attggctgtg    7620
gtatataaaa ttattcataa tgatagtagg aggcttggta ggtttaagaa tagttttgc     7680 tgtactttct atagtgaata gagttaggca gggatattca ccattatcgt ttcagaccca    7740
cctcccaatc ccgaggggac ccgacaggcc cgaaggaata agaagaagaa gtggagagag    7800
agacagagac agatccattc gattagtgaa cggatcctta gcacttatct gggacgatct    7860
gcggagcctg tgcctcttca gctaccaccg cttgagagac ttactcttga ttgtaacgag    7920
gattgtggaa cttctgggac gcaggggggtg ggaagccctc aaatattggt ggaatctcct    7980
acagtattgg agtcaggaac taaagaatag tgctgttaac ttgctcaatg ccacagccat    8040
agcagtagct gaggggacag ataggggttat agaagtatta caagcagctt atagagctat   8100
tcgccacata cctagaagaa taagacaggg cttggaaagg attttgctat aagatgggtg    8160
gcaagtggtc aaaaagtagt gtgattggat ggcctgctgt aagggaaaga atgagacgag    8220
ctgagccagc agcagatggg gtgggagcag tatctcgaga cctagaaaaa catggagcaa    8280
tcacaagtag caatacagca gctaacaatg ctgcttgtgc ctggctagaa gcacaagagg    8340
aggaagaggt gggttttcca gtcacacctc aggtaccttt aagaccaatg acttacaagg    8400
cagctgtaga tcttagccac tttttaaaag aaaaggggg actggaaggg ctaattcact    8460
cccaaagaag acaagatatc cttgatctgt ggatctacca cacacaaggc tacttccctg    8520
attggcagaa ctacacacca gggccagggg tcagatatcc actgaccttt ggatggtgct    8580
acaagctagt accagttgag ccagataagg tagaagaggc caataaagga gagaacacca    8640
gcttgttaca ccctgtgagc ctgcatggaa tggatgaccc tgagagagaa gtgttagagt    8700 ggaggttga cagccgccta gcatttcatc acgtggcccg agagctgcat ccggagtact     8760
tcaagaactg ctgacatcga gcttgctaca agggactttc cgctggggac tttccaggga   8820
ggcgtggcct gggcgggact ggggagtggc gagccctcag atgctgcata taagcagctg    8880
ctttttgcct gtactgggtc tctctggtta gaccagatct gagcctggga gctctctggc    8940
taactaggga acccactgct taagcctcaa taaagcttgc cttgagtgct tcaagtagtg    9000
tgtgcccgtc tgttgtgtga ctctggtaac tagagatccc tcagacccett ttagtcagtg    9060 tggaaaatct ctagcactcg agtctagacc ctcgaggaga acttctagta tatccacata    9120
cctaatatta ttgccttatt aaaaatggaa tcccaacaat tacatcaaaa tccacattct    9180
cttcaaaatc aattgtcctg tacttccttg ttcatgtgtg ttcaaaaacg ttatatttat    9240
aggataatta tactctattt ctcaacaagt aattggttgt ttggccgagc ggtctaaggc    9300
gcctgattca agaaatatct tgaccgcagt taactgtggg aatactcagg tatcgtaaga    9360
tgcaagagtt cgaatctctt agcaaccatt atttttttcc tcaacataac gagaacacac    9420
```

```
aggggcgcta tcgcacagaa tcaaattcga tgactggaaa ttttttgtta atttcagagg   9480
tcgcctgacg catatacctt tttcaactga aaaattggga gaaaaggaa aggtgagagg    9540 ccggaaccgg cttttcatat agaatagaga agcgttcatg actaaatgct tgcatcacaa   9600
tacttgaagt tgacaatatt atttaaggac ctattgtttt ttccaatagg tggttagcaa   9660
tcgtcttact ttctaacttt tcttaccttt tacatttcag caatatatat atatatttca   9720
aggatatacc attctaatgt ctgcccctat gtctgcccct aagaagatcg tcgttttgcc   9780
aggtgaccac gttggtcaag aaatcacagc cgaagccatt aaggttctta aagctatttc   9840
tgatgttcgt tccaatgtca agttcgattt cgaaaatcat ttaattggtg gtgctgctat   9900
cgatgctaca ggtgtcccac ttccagatga ggcgctggaa gcctccaaga aggttgatgc   9960
cgttttgtta ggtgctgtgg gtggtcctaa atggggtacc ggtagtgtta gacctgaaca  10020
aggtttacta aaaatccgta aagaacttca attgtacgcc aacttaagac catgtaactt  10080
tgcatccgac tctcttttag acttatctcc aatcaagcca caatttgcta aaggtactga  10140
cttcgttgtt gtcagagaat tagtgggagg tatttacttt ggtaagagaa aggaagacga  10200
tggtgatggt gtcgcttggg atagtgaaca atacaccgtt ccagaagtgc aaagaatcac  10260
aagaatggcc gctttcatgg ccctacaaca tgagccacca ttgcctattt ggtccttgga  10320
taaagctaat gttttggcct cttcaagatt atggagaaaa actgtggagg aaaccatcaa  10380
gaacgaattc cctacattga aggttcaaca tcaattgatt gattctgccg ccatgatcct  10440
agttaagaac ccaacccacc taaatggtat tataatcacc agcaacatgt ttggtgatat  10500
catctccgat gaagcctccg ttatcccagg ttccttgggt ttgttgccat ctgcgtcctt  10560
ggcctctttg ccagacaaga acaccgcatt tggtttgtac gaaccatgcc acggttctgc  10620
tccagatttg ccaagaaata aggttgaccc tatcgccact atcttgtctg ctgcaatgat  10680
gttgaaattg tcattgaact tgcctgaaga aggtaaggcc attgaagatg cagttaaaaa  10740
ggttttggat gcaggtatca gaactggtga tttaggtggt tccaacagta ccaccgaagt  10800
cggtgatgct gtcgccgaag aagttaagaa aatccttgct taaaaagatt ctctttttt   10860 atgatatttg tacataaact ttataaatga aattcataat agaaacgaca cgaaattaca  10920
aaatggaata tgttcatagg gtagacgaaa ctatatacgc aatctacata catttatcaa  10980
gaaggagaaa aaggaggata gtaaaggaat acaggtaagc aaattgatac taatggctca  11040
acgtgataag gaaaaagaat tgcactttaa cattaatatt gacaaggagg agggcaccac  11100
acaaaaagtt aggtgtaaca gaaaatcatg aaactacgat tcctaatttg atattggagg  11160
attttctcta aaaaaaaaaa aatacaacaa ataaaaaaca ctcaatgacc tgaccatttg  11220
atggagttta agtcaatacc ttcttgaacc atttccata atggtgaaag ttccctcaag  11280
aattttactc tgtcagaaac ggccttacga cgtagtcgat atggtgcact ctcagtacaa  11340
tctgctctga tgccgcatag ttaagccagc cccgacaccc gccaacaccc gctgacgcgc  11400
cctgacgggc ttgtctgctc ccggcatccg cttacagaca agctgtgacc gtctccggga  11460
gctgcatgtg tcagaggttt tcaccgtcat caccgaaacg cgcgagacga agggcctcg   11520 tgatacgcct attttatag gttaatgtca tgataataat ggtttcttag gacggatcgc   11580
ttgcctgtaa cttacacgcg cctcgtatct tttaatgatg gaataatttg ggaatttact  11640
ctgtgtttat ttatttttat gttttgtatt tggatttag aaagtaaata agaaggtag    11700 aagagttacg gaatgaagaa aaaaaaataa acaaaggttt aaaaaatttc aacaaaagc    11760 gtactttaca tatatatttta ttagacaaga aaagcagatt aaatagatat acattcgatt  11820
```

```
aacgataagt aaaatgtaaa atcacaggat tttcgtgtgt ggtcttctac acagacaaga   11880
tgaaacaatt cggcattaat acctgagagc aggaagagca agataaaagg tagtatttgt   11940
tggcgatccc cctagagtct tttacatctt cggaaaacaa aaactatttt ttctttaatt   12000
tcttttttta ctttctattt ttaatttata tatttatatt aaaaaattta aattataatt   12060
atttttatag cacgtgatga aaaggaccca ggtggcactt ttcggggaaa tgtgcgcgga   12120
acccctattt gtttattttt ctaaatacat tcaaatatgt atccgctcta gagggcccgt   12180
ttaaacccgc tgatcagcct cgactgtgcc ttctagttgc cagccatctg ttgtttgccc   12240
ctcccccgtg ccttccttga ccctggaagg tgccactccc actgtccttt cctaataaaa   12300
tgaggaaatt gcatcgcatt gtctgagtag gtgtcattct attctggggg gtggggtggg   12360
gcaggacagc aagggggagg attgggaaga caatagcagg catgctgggg atgcggtggg   12420
ctctatggct tctgaggcgg aaagaaccag ctggggctct aggggtatc cccacgcgcc   12480 ctgtagcggc gcattaagcg cggcgggtgt ggtggttacg cgcagcgtga ccgctacact   12540
tgccagcgcc ctagcgcccg ctcctttcgc tttcttccct tcctttctcg ccacgttcgc   12600
cggctttccc cgtcaagctc taaatcgggg catcccttta gggttccgat ttagtgcttt   12660
acggcacctc gaccccaaaa aacttgatta gggtgatggt tcacgtagtg ggccatcgcc   12720
ctgatagacg gttttttcgcc ctttgacgtt ggagtccacg ttctttaata gtggactctt   12780
gttccaaact ggaacaacac tcaaccctat ctcggtctat tcttttgatt tataagggat   12840
tttgggattt tcggcctatt ggttaaaaaa tgagctgatt taacaaaaat ttaacgcgaa   12900
ttaattctgt ggaatgtgtg tcagttaggg tgtggaaagt ccccaggctc cccaggcagg   12960
cagaagtatg caaagcatgc atctcaatta gtcagcaacc aggtgtggaa agtccccagg   13020
ctccccagca ggcagaagta tgcaaagcat gcatctcaat tagtcagcaa ccatagtccc   13080
gcccctaact ccgcccatcc cgcccctaac tccgcccagt tccgcccatt ctccgcccca   13140
tggctgacta attttttttta tttatgcaga ggccgaggcc gcctctgcct ctgagctatt   13200
ccagaagtag tgaggaggct ttttttggagg cctaggcttt tgcaaaaagc tcccgggagc   13260
ttgtatatcc attttcggat ctgatcagca cgtgttgaca attaatcatc ggcatagtat   13320
atcggcatag tataatacga caaggtgagg aactaaacca tggccaagtt gaccagtgcc   13380
gttccggtgc tcaccgcgcg cgacgtcgcc ggagcggtcg agttctggac cgaccggctc   13440
gggttctccc gggacttcgt ggaggacgac ttcgccggtg tggtccggga cgacgtgacc   13500
ctgttcatca gcgcggtcca ggaccaggtg gtgccggaca cacccctggc ctgggtgtgg   13560
gtgcgcggcc tggacgagct gtacgccgag tggtcggagg tcgtgtccac gaacttccgg   13620
gacgcctccg gccggccat gaccgagatc ggcgagcagc cgtgggggcg ggagttcgcc   13680
ctgcgcgacc cggccggcaa ctgcgtgcac ttcgtggccg aggagcagga ctgacacgtg   13740
ctacgagatt tcgattccac cgccgccttc tatgaaaggt tgggcttcgg aatcgttttc   13800
cgggacgccg gctggatgat cctccagcgc ggggatctca tgctggagtt cttcgcccac   13860
cccaacttgt ttattgcagc ttataatggt tacaaataaa gcaatagcat cacaaatttc   13920
acaaataaag cattttttc actgcattct agttgtggtt tgtccaaact catcaatgta   13980
tcttatcatg tctgtatacc gtcgacctct agctagagct tggcgtaatc atggtcatag   14040
ctgtttcctg tgtgaaattg ttatccgctc acaattccac acaacatacg agccggaagc   14100
ataaagtgta aagcctgggg tgcctaatga gtgagctaac tcacattaat tgcgttgcgc   14160
tcactgcccg ctttccagtc gggaaacctg tcgtgccagc tgcattaatg aatcggccaa   14220
```

```
cgcgcgggga gaggcggttt gcgtattggg cgctcttccg cttcctcgct cactgactcg   14280
ctgcgctcgg tcgttcggct gcggcgagcg gtatcagctc actcaaaggc ggtaatacgg   14340
ttatccacag aatcagggga taacgcagga agaacatgt gagcaaaagg ccagcaaaag   14400
gccaggaacc gtaaaaaggc gcgcgttgctg gcgttttttcc ataggctccg ccccccctgac 14460
gagcatcaca aaatcgacg ctcaagtcag aggtggcgaa acccgacagg actataaaga   14520
taccaggcgt ttccccctgg aagctccctc gtgcgctctc ctgttccgac cctgccgctt   14580
accggatacc tgtccgcctt tctcccttcg ggaagcgtgg cgctttctca atgctcacgc   14640
tgtaggtatc tcagttcggt gtaggtcgtt cgctccaagc tgggctgtgt gcacgaaccc   14700
cccgttcagc ccgaccgctg cgccttatcc ggtaactatc gtcttgagtc caacccggta   14760
agacacgact tatcgccact ggcagcagcc actggtaaca ggattagcag agcgaggtat   14820
gtaggcggtg ctacagagtt cttgaagtgg tggcctaact acggctacac tagaaggaca   14880
gtatttggta tctgcgctct gctgaagcca gttaccttcg gaaaaagagt tggtagctct   14940
tgatccggca acaaaccac cgctggtagc ggtggttttt ttgtttgcaa gcagcagatt   15000
acgcgcagaa aaaaggatc tcaagaagat cctttgatct tttctacggg gtctgacgct   15060
cagtggaacg aaaactcacg ttaagggatt ttggtcatga gattatcaaa aaggatcttc   15120
acctagatcc ttttaaatta aaaatgaagt tttaaatcaa tctaaagtat atatgagtaa   15180
acttggtctg acagttacca atgcttaatc agtgaggcac ctatctcagc gatctgtcta   15240
tttcgttcat ccatagttgc ctgactcccc gtcgtgtaga taactacgat acgggagggc   15300
ttaccatctg gccccagtgc tgcaatgata ccgcgagacc cacgctcacc ggctccagat   15360
ttatcagcaa taaccagcc agccggaagg gccgagcgca gaagtggtcc tgcaacttta   15420
tccgcctcca tccagtctat taattgttgc cgggaagcta gagtaagtag ttcgccagtt   15480
aatagtttgc gcaacgttgt tgccattgct acaggcatcg tggtgtcacg ctcgtcgttt   15540
ggtatggctt cattcagctc cggttcccaa cgatcaaggc gagttacatg atcccccatg   15600
ttgtgcaaaa aagcggttag ctccttcggt cctccgatcg ttgtcagaag taagttggcc   15660
gcagtgttat cactcatggt tatggcagca ctgcataatt ctcttactgt catgccatcc   15720
gtaagatgct tttctgtgac tggtgagtac tcaaccaagt cattctgaga atagtgtatg   15780
cggcgaccga gttgctcttg cccggcgtca atacgggata ataccgcgcc acatagcaga   15840
actttaaaag tgctcatcat tggaaaacgt tcttcggggc gaaaactctc aaggatctta   15900
ccgctgttga tccagttc gatgtaaccc actcgtgcac ccaactgatc ttcagcatct   15960
tttactttca ccagcgtttc tgggtgagca aaaacaggaa ggcaaaatgc cgcaaaaaag   16020
ggaataaggg cgacacggaa atgttgaata ctcatactct tcctttttca atattattga   16080
agcatttatc agggttattg tctcatgagc ggatacatat ttgaatgtat ttagaaaaat   16140
aaacaaatag gggttccgcg cacatttccc cgaaaagtgc cacctgacgt cgacggatcg   16200
ggagatctcc cgatcccta tggtcgactc tcagtacaat ctgctctgat gccgcatagt   16260
taagccagta tctgctccct gcttgtgtgt tggaggtcgc tgagtagtgc gcgagcaaaa   16320
tttaagctac aacaaggcaa ggcttgaccg acaattgcat gaagaatctg cttagggtta   16380
ggcgttttgc gctgcttcgc gatgtacggg ccagatatac gcgttgacat tgattattga   16440
ctagttatta atagtaatca attacgggt cattagttca tagcccatat atggagttcc   16500
gcgttacata acttacggta atggcccgc ctggctgacc gcccaacgac ccccgcccat   16560
tgacgtcaat aatgacgtat gttcccatag taacgccaat agggactttc cattgacgtc   16620
```

-continued

| | |
|---|---|
| aatgggtgga ctatttacgg taaactgccc acttggcagt acatcaagtg tatcatatgc | 16680 |
| caagtacgcc ccctattgac gtcaatgacg gtaaatggcc cgcctggcat tatgcccagt | 16740 |
| acatgacctt atgggacttt cctacttggc agtacatcta cgtattagtc atcgctatta | 16800 |
| ccatggtgat gcggttttgg cagtacatca atgggcgtgg atagcggttt gactcacggg | 16860 |
| gatttccaag tctccacccc attgacgtca atgggagttt gttttggcac caaaatcaac | 16920 |
| gggactttcc aaaatgtcgt aacaactccg ccccattgac gcaaatgggc ggtaggcgtg | 16980 |
| tacggtggga ggtctatata agcagagctc tctggctaac | 17020 |

<210> SEQ ID NO 2
<211> LENGTH: 15166
<212> TYPE: DNA
<213> ORGANISM: Artificial Sequence
<220> FEATURE:
<223> OTHER INFORMATION: Plasmid sequence containing HIV-1, E-coli, and yeast sequences.

<400> SEQUENCE: 2

| | |
|---|---|
| cacatggaaa agattagtaa aacaccatat gtatatttca aggaaagcta aggactggtt | 60 |
| ttatagacat cactatgaaa gtactaatcc aaaaataagt tcagaagtac acatcccact | 120 |
| aggggatgct aaattagtaa taacaacata ttggggtctg catacaggag aaagagactg | 180 |
| gcatttgggt cagggagtct ccatagaatg gaggaaaaag agatatagca cacaagtaga | 240 |
| ccctgaccta gcagaccaac taattcatct gcactatttt gattgttttt cagaatctgc | 300 |
| tataagaaat accatattag gacgtatagt tagtcctagg tgtgaatatc aagcaggaca | 360 |
| taacaaggta ggatctctac agtacttggc actagcagca ttaataaaac caaaacagat | 420 |
| aaagccacct ttgcctagtg ttaggaaact gacagaggac agatggaaca gccccagaa | 480 |
| gaccaagggc cacagaggga gccatacaat gaatggacac tagagctttt agaggaactt | 540 |
| aagagtgaag ctgttagaca ttttcctagg atatggctcc ataacttagg acaacatatc | 600 |
| tatgaaactt acggggatac ttgggcagga gtggaagcca taataagaat tctgcaacaa | 660 |
| ctgctgttta ccatttcag aattgggtgt cgacatagca gaataggcgt tactcgacag | 720 |
| aggagagcaa gaaatggagc cagtagatcc tagactagag ccctggaagc atccaggaag | 780 |
| tcagcctaaa actgcttgta ccaattgcta ttgtaaaaag tgttgctttc attgccaagt | 840 |
| ttgtttcatg acaaaagcct taggcatctc ctatggcagg aagaagcgga gacagcgacg | 900 |
| aagagctcat cagaacagtc agactcatca agcttctcta tcaaagcagt aagtagtaca | 960 |
| tgtaatgcaa cctataatag tagcaatagt agcattagta gtagcaataa taatagcaat | 1020 |
| agttgtgtgg tccatagtaa tcatagaata taggaaaata ttaagacaaa gaaaatagac | 1080 |
| aggttaatt gatagactaa tagaaagagc agaagacagt ggcaatgaga gtgaaggaga | 1140 |
| agtatcagca cttgtggaga tggggtgga atgggcac catgctcctt gggatattga | 1200 |
| tgatctgtag tgctacagaa aaattgtggg tcacagtcta ttatgggta cctgtgtgga | 1260 |
| aggaagcaac caccactcta ttttgtgcat cagatgctaa agcatatgat acagaggtac | 1320 |
| ataatgtttg ggccacacat gcctgtgtac ccacagaccc caacccacaa gaagtagtat | 1380 |
| tggtaaatgt gacagaaaat tttaacatgt ggaaaaatga catggtagaa cagatgcatg | 1440 |
| aggatataat cagtttatgg gatcaaagcc taaagccatg tgtaaaatta accccactct | 1500 |
| gtgttagttt aaagtgcact gatttgaaga atgatactaa taccaatagt agtagcggga | 1560 |
| gaatgataat ggagaaagga gagataaaaa actgctcttt caatatcagc acaagcataa | 1620 |
| gagataaggt gcagaaagaa tatgcattct tttataaact tgatatagta ccaatagata | 1680 |

```
ataccagcta taggttgata agttgtaaca cctcagtcat tacacaggcc tgtccaaagg    1740
tatcctttga gccaattccc atacattatt gtgccccggc tggttttgcg attctaaaat    1800
gtaataataa gacgttcaat ggaacaggac catgtacaaa tgtcagcaca gtacaatgta    1860
cacatggaat caggccagta gtatcaactc aactgctgtt aaatggcagt ctagcagaag    1920
aagatgtagt aattagatct gccaatttca cagacaatgc taaaaccata atagtacagc    1980
tgaacacatc tgtagaaatt aattgtacaa gacccaacaa caatacaaga aaaagtatcc    2040
gtatccagag gggaccaggg agagcatttg ttacaatagg aaaaatagga atatgagac    2100 aagcacattg taacattagt agagcaaaat ggaatgccac tttaaaacag atagctagca    2160
aattaagaga acaatttgga aataataaaa caataatctt taagcaatcc tcaggagggg    2220
acccagaaat tgtaacgcac agttttaatt gtggagggga atttttctac tgtaattcaa    2280
cacaactgtt taatagtact tggtttaata gtacttggag tactgaaggg tcaaataaca    2340
ctgaaggaag tgacacaatc acactcccat gcagaataaa acaatttata aacatgtggc    2400
aggaagtagg aaaagcaatg tatgcccctc ccatcagtgg acaaattaga tgttcatcaa    2460
atattactgg gctgctatta acaagagatg gtggtaataa caacaatggg tccgagatct    2520
tcagacctgg aggaggcgat atgagggaca attggagaag tgaattatat aaatataaag    2580
tagtaaaaat tgaaccatta ggagtagcac ccaccaaggc aaagagaaga gtggtgcaga    2640
gagaaaaaag agcagtggga ataggagctt tgttccttgg gttcttggga gcagcaggaa    2700
gcactatggg ctgcacgtca atgacgctga cggtacaggc cagacaatta ttgtctgata    2760
tagtgcagca gcagaacaat ttgctgaggg ctattgaggc gcaacagcat ctgttgcaac    2820
tcacagtctg gggcatcaaa cagctccagg caagaatcct ggctgtggaa agatacctaa    2880
aggatcaaca gctcctgggg atttggggtt gctctggaaa actcatttgc accactgctg    2940
tgccttggaa tgctagttgg agtaataaat ctctggaaca gatttggaat aacatgacct    3000
ggatggagtg ggacagagaa attaacaatt acacaagctt aatacactcc ttaattgaag    3060
aatcgcaaaa ccagcaagaa aagaatgaac aagaattatt ggaattagat aaatgggcaa    3120
gtttgtggaa ttggtttaac ataacaaatt ggctgtggta tataaaatta ttcataatga    3180
tagtaggagg cttggtaggt ttaagaatag ttttgctgt actttctata gtgaatagag    3240
ttaggcaggg atattcacca ttatcgtttc agacccacct cccaatcccg aggggacccg    3300
acaggcccga aggaatagaa gaagaaggtg agagagaga cagagacaga tccattcgat    3360
tagtgaacgg atccttagca cttatctggg acgatctgcg gagcctgtgc ctcttcagct    3420
accaccgctt gagagactta ctcttgattg taacgaggat tgtggaactt ctgggacgca    3480
gggggtggga agccctcaaa tattggtgga atctcctaca gtattggagt caggaactaa    3540
agaatagtgc tgttaacttg ctcaatgcca cagccatagc agtagctgag gggacagata    3600
gggttataga agtattacaa gcagcttata gagctattcg ccacatacct agaagaataa    3660
gacagggctt ggaaaggatt ttgctataag atgggtggca agtggtcaaa agtagtgtg    3720 attggatggc ctgctgtaag ggaaagaatg agacgagctg agccagcagc agatgggggtg    3780 ggagcagtat ctcgagacct agaaaaacat ggagcaatca caagtagcaa tacagcagct    3840
aacaatgctg cttgtgcctg gctagaagca caagaggagg aagaggtggg ttttccagtc    3900
acacctcagg taccttaag accaatgact tacaaggcag ctgtagatct tagccacttt    3960
ttaaaagaaa agggggggact ggaagggcta attcactccc aaagaagaca agatatcctt    4020
gatctgtgga tctaccacac acaaggctac ttccctgatt ggcagaacta cacaccaggg    4080
```

```
ccaggggtca gatatccact gacctttgga tggtgctaca agctagtacc agttgagcca    4140
gataaggtag aagaggccaa taaaggagag aacaccagct tgttacaccc tgtgagcctg    4200
catgaatgg atgaccctga gagagaagtg ttagagtgga ggtttgacag ccgcctagca     4260
tttcatcacg tggcccgaga gctgcatccg gagtacttca agaactgctg acatcgagct    4320
tgctacaagg gactttccgc tggggacttt ccagggaggc gtggcctggg cgggactggg    4380
gagtggcgag ccctcagatg ctgcatataa gcagctgctt tttgcctgta ctgggtctct    4440
ctggttagac cagatctgag cctgggagct ctctggctaa ctagggaacc cactgcttaa    4500
gcctcaataa agcttgcctt gagtgcttca agtagtgtgt gcccgtctgt tgtgtgactc    4560
tggtaactag agatccctca gaccttttta gtcagtgtgg aaaatctcta gcactcgagt    4620
ctagaccctc gaggagaact tctagtatat ccacatacct aatattattg ccttattaaa    4680
aatggaatcc caacaattac atcaaaatcc acattctctt caaaatcaat tgtcctgtac    4740
ttccttgttc atgtgtgttc aaaaacgtta tatttatagg ataattatac tctatttctc    4800
aacaagtaat tggttgtttg ccgagcggt ctaaggcgcc tgattcaaga aatatcttga     4860
ccgcagttaa ctgtgggaat actcaggtat cgtaagatgc aagagttcga atctcttagc    4920
aaccattatt tttttcctca acataacgag aacacacagg ggcgctatcg cacagaatca    4980
aattcgatga ctgaaaattt tttgttaatt tcagaggtcg cctgacgcat atacctttt     5040
caactgaaaa attgggagaa aaaggaaagg tgagaggccg aaccggctt ttcatataga     5100
atagagaagc gttcatgact aaatgcttgc atcacaatac ttgaagttga caatattatt    5160
taaggaccta ttgttttttc caataggtgg ttagcaatcg tcttactttc taacttttct    5220
taccttttac atttcagcaa tatatatata tatttcaagg ataccatt ctaatgtctg      5280
cccctatgtc tgcccctaag aagatcgtcg ttttgccagg tgaccacgtt ggtcaagaaa    5340
tcacagccga agccattaag gttcttaaag ctatttctga tgttcgttcc aatgtcaagt    5400
tcgatttcga aaatcattta attggtggtg ctgctatcga tgctacaggt gtcccacttc    5460
cagatgaggc gctggaagcc tccaagaagg ttgatgccgt tttgttaggt gctgggtg     5520
gtcctaaatg gggtaccggt agtgttagac ctgaacaagg tttactaaaa atccgtaaag    5580
aacttcaatt gtacgccaac ttaagaccat gtaactttgc atccgactct cttttagact    5640
tatctccaat caagccacaa tttgctaaag gtactgactt cgttgttgtc agagaattag    5700
tgggaggtat ttactttggt aagagaaagg aagacgatgg tgatggtgtc gcttgggata    5760
gtgaacaata caccgttcca gaagtgcaaa gaatcacaag aatggccgct tcatggccc     5820
tacaacatga gccaccattg cctatttggt ccttggataa agctaatgtt ttggcctctt    5880
caagattatg gagaaaaact gtggaggaaa ccatcaagaa cgaattccct acattgaagg    5940
ttcaacatca attgattgat tctgccgcca tgatcctagt taagaaccca acccacctaa    6000
atggtattat aatcaccagc aacatgtttg gtgatatcat ctccgatgaa gcctccgtta    6060
tcccaggttc cttgggtttg ttgccatctg cgtccttggc ctcttgcca gacaagaaca     6120
ccgcatttgg tttgtacgaa ccatgccacg gttctgctcc agatttgcca aagaataagg    6180
ttgaccctat cgccactatc ttgtctgctg caatgatgtt gaaattgtca ttgaacttgc    6240
ctgaagaagg taaggccatt gaagatgcag ttaaaaaggt tttggatgca ggtatcagaa    6300
ctggtgattt aggtggttcc aacagtacca ccgaagtcgg tgatgctgtc gccgaagaag    6360
ttaagaaaat ccttgcttaa aaagattctc ttttttatg atatttgtac ataaacttta    6420
taaatgaaat tcataataga aacgacacga aattacaaaa tggaatatgt tcatgggta     6480
```

```
gacgaaacta tatacgcaat ctacatacat ttatcaagaa ggagaaaaag gaggatagta    6540
aaggaataca ggtaagcaaa ttgatactaa tggctcaacg tgataaggaa aaagaattgc    6600
actttaacat taatattgac aaggaggagg gcaccacaca aaaagttagg tgtaacagaa    6660
aatcatgaaa ctacgattcc taatttgata ttggaggatt ttctctaaaa aaaaaaaaat    6720
acaacaaata aaaacactc aatgacctga ccatttgatg gagtttaagt caataccttc     6780
ttgaaccatt tcccataatg gtgaaagttc cctcaagaat tttactctgt cagaaacggc    6840
cttacgacgt agtcgatatg gtgcactctc agtacaatct gctctgatgc cgcatagtta    6900
agccagcccc gacacccgcc aacacccgct gacgcgccct gacgggcttg tctgctcccg    6960
gcatccgctt acagacaagc tgtgaccgtc tccgggagct gcatgtgtca gaggttttca    7020
ccgtcatcac cgaaacgcgc gagacgaaag gcctcgtga  tacgcctatt tttataggtt    7080
aatgtcatga taataatggt ttcttaggac ggatcgcttg cctgtaactt cacgcgcct     7140 cgtatctttt aatgatggaa taatttggga atttactctg tgtttattta tttttatgtt    7200
ttgtatttgg attttagaaa gtaaataaag aaggtagaag agttacggaa tgaagaaaaa    7260
aaaataaaca aaggtttaaa aaatttcaac aaaaagcgta ctttacatat atatttatta    7320
gacaagaaaa gcagattaaa tagatataca ttcgattaac gataagtaaa atgtaaaatc    7380
acaggatttt cgtgtgtggt cttctacaca gacaagatga aacaattcgg cattaatacc    7440
tgagagcagg aagagcaaga taaaaggtag tatttgttgg cgatccccct agagtctttt    7500
acatcttcgg aaaacaaaaa ctattttttc tttaatttct ttttttactt tctatttta    7560 atttatatat ttatattaaa aaatttaaat tataattatt tttatagcac gtgatgaaaa    7620
ggacccaggt ggcactttc ggggaaatgt gcgcggaacc cctatttgtt tattttcta     7680 aatacattca aatatgtatc cgctctagag ggcccgttta aacccgctga tcagcctcga    7740
ctgtgccttc tagttgccag ccatctgttg tttgccccctc ccccgtgcct tccttgaccc   7800
tggaaggtgc cactcccact gtccttttcct aataaaatga ggaaattgca tcgcattgtc   7860
tgagtaggtg tcattctatt ctggggggtg gggtgggca ggacagcaag ggggaggatt     7920
gggaagacaa tagcaggcat gctggggatg cggtgggctc tatggcttct gaggcggaaa    7980
gaaccagctg gggctctagg gggtatcccc acgcgccctg tagcggcgca ttaagcgcgg    8040
cgggtgtggt ggttacgcgc agcgtgaccg ctacacttgc cagcgcccta gcgcccgctc    8100
ctttcgcttt cttcccttcc tttctcgcca cgttcgccgg cttccccgt  caagctctaa    8160 atcgggcat ccctttaggg ttccgattta gtgctttacg gcacctcgac cccaaaaaac     8220
ttgattaggg tgatggttca cgtagtgggc catcgccctg atagacggtt tttcgccctt    8280
tgacgttgga gtccacgttc tttaatagtg gactcttgtt ccaaactgga acaacactca    8340
accctatctc ggtctattct tttgatttat aagggatttt ggggatttcg gcctattggt    8400
taaaaaatga gctgatttaa caaaaattta acgcgaatta ttctgtgga atgtgtgtca     8460 gttagggtgt ggaaagtccc caggctcccc aggcaggcag aagtatgcaa gcatgcatc     8520 tcaattagtc agcaaccagg tgtggaaagt ccccaggctc cccagcaggc agaagtatgc    8580
aaagcatgca tctcaattag tcagcaacca tagtcccgcc cctaactccg cccatcccgc    8640
ccctaactcc gcccagttcc gcccattctc cgccccatgg ctgactaatt ttttttattt    8700
atgcagaggc cgaggccgcc tctgcctctg agctattcca gaagtagtga ggaggctttt    8760
ttggaggcct aggcttttgc aaaaagctcc cgggagcttg tatatccatt ttcggatctg    8820
atcagcacgt gttgacaatt aatcatcggc atagtatatc ggcatagtat aatacgacaa    8880
```

```
ggtgaggaac taaaccatgg ccaagttgac cagtgccgtt ccggtgctca ccgcgcgcga    8940
cgtcgccgga gcggtcgagt tctggaccga ccggctcggg ttctcccggg acttcgtgga    9000
ggacgacttc gccggtgtgg tccgggacga cgtgaccctg ttcatcagcg cggtccagga    9060
ccaggtggtg ccggacaaca ccctggcctg ggtgtgggtg cgcggcctgg acgagctgta    9120
cgccgagtgg tcggaggtcg tgtccacgaa cttccgggac gcctccgggc cggccatgac    9180
cgagatcggc gagcagccgt gggggcggga gttcgccctg cgcgacccgg ccggcaactg    9240
cgtgcacttc gtggccgagg agcaggactg acacgtgcta cgagatttcg attccaccgc    9300
cgccttctat gaaaggttgg gcttcggaat cgttttccgg gacgccggct ggatgatcct    9360
ccagcgcggg gatctcatgc tggagttctt cgcccacccc aacttgttta ttgcagctta    9420
taatggttac aaataaagca atagcatcac aaatttcaca aataaagcat ttttttcact    9480
gcattctagt tgtggtttgt ccaaactcat caatgtatct tatcatgtct gtataccgtc    9540
gacctctagc tagagcttgg cgtaatcatg gtcatagctg tttcctgtgt gaaattgtta    9600
tccgctcaca attccacaca acatacgagc cggaagcata agtgtaaag cctggggtgc     9660
ctaatgagtg agctaactca cattaattgc gttgcgctca ctgcccgctt ccagtcggg     9720
aaacctgtcg tgccagctgc attaatgaat cggccaacgc gcgggagag gcggtttgcg     9780
tattgggcgc tcttccgctt cctcgctcac tgactcgctg cgctcggtcg ttcggctgcg    9840
gcgagcggta tcagctcact caaaggcggt aatacggtta ccacagaat caggggataa     9900
cgcaggaaag aacatgtgag caaaaggcca gcaaaaggcc aggaaccgta aaaaggccgc    9960
gttgctggcg ttttccata ggctccgccc ccctgacgag catcacaaaa atcgacgctc     10020
aagtcagagg tggcgaaacc cgacaggact ataaagatac caggcgtttc ccctggaag    10080
ctccctcgtg cgctctcctg ttccgaccct gccgcttacc ggatacctgt ccgcctttct   10140
cccttcggga agcgtggcgc tttctcaatg ctcacgctgt aggtatctca gttcggtgta   10200
ggtcgttcgc tccaagctgg gctgtgtgca cgaacccccc gttcagcccg accgctgcgc   10260
cttatccggt aactatcgtc ttgagtccaa cccggtaaga cacgacttat cgccactggc   10320
agcagccact ggtaacagga ttagcagagc gaggtatgta ggcggtgcta cagagttctt   10380
gaagtggtgg cctaactacg gctacactag aaggacagta tttggtatct gcgctctgct   10440
gaagccagtt accttcggaa aaagagttgg tagctcttga tccggcaaac aaaccaccgc   10500
tggtagcggt ggttttttg tttgcaagca gcagattacg cgcagaaaaa aaggatctca    10560
agaagatcct ttgatctttt ctacggggtc tgacgctcag tggaacgaaa actcacgtta   10620
agggattttg gtcatgagat tatcaaaaag gatcttcacc tagatccttt taaattaaaa   10680
atgaagtttt aaatcaatct aaagtatata tgagtaaact tggtctgaca gttaccaatg   10740
cttaatcagt gaggcaccta tctcagcgat ctgtctattt cgttcatcca tagttgcctg   10800
actccccgtc gtgtagataa ctacgatacg ggagggctta ccatctggcc ccagtgctgc   10860
aatgataccg cgagacccac gctcaccggc tccagattta tcagcaataa accagccagc   10920
cggaagggcc gagcgcagaa gtggtcctgc aactttatcc gcctccatcc agtctattaa   10980
ttgttgccgg gaagctagag taagtagttc gccagttaat agtttgcgca acgttgttgc   11040
cattgctaca ggcatcgtgg tgtcacgctc gtcgtttggt atggcttcat tcagctccgg   11100
ttcccaacga tcaaggcgag ttacatgatc ccccatgttg tgcaaaaaag cggttagctc   11160
cttcggtcct ccgatcgttg tcagaagtaa gttggccgca gtgttatcac tcatggttat   11220
ggcagcactg cataattctc ttactgtcat gccatccgta agatgctttt ctgtgactgg   11280
```

```
tgagtactca accaagtcat tctgagaata gtgtatgcgg cgaccgagtt gctcttgccc   11340
ggcgtcaata cgggataata ccgcgccaca tagcagaact ttaaaagtgc tcatcattgg   11400
aaaacgttct tcggggcgaa aactctcaag gatcttaccg ctgttgagat ccagttcgat   11460
gtaacccact cgtgcaccca actgatcttc agcatctttt actttcacca gcgtttctgg   11520
gtgagcaaaa acaggaaggc aaaatgccgc aaaaaaggga ataagggcga cacggaaatg   11580
ttgaatactc atactcttcc tttttcaata ttattgaagc atttatcagg gttattgtct   11640
catgagcgga tacatatttg aatgtattta gaaaaataaa caaatagggg ttccgcgcac   11700
atttccccga aaagtgccac ctgacgtcga cggatcggga gatctcccga tcccctatgg   11760
tcgactctca gtacaatctg ctctgatgcc gcatagttaa gccagtatct gctccctgct   11820
tgtgtgttgg aggtcgctga gtagtgcgcg agcaaaattt aagctacaac aaggcaaggc   11880
ttgaccgaca attgcatgaa gaatctgctt agggttaggc gttttgcgct gcttcgcgat   11940
gtacgggcca gatatacgcg ttgacattga ttattgacta gttattaata gtaatcaatt   12000
acggggtcat tagttcatag cccatatatg gagttccgcg ttacataact tacggtaaat   12060
ggcccgcctg gctgaccgcc caacgacccc cgcccattga cgtcaataat gacgtatgtt   12120
cccatagtaa cgccaatagg gactttccat tgacgtcaat gggtggacta tttacggtaa   12180
actgcccact tggcagtaca tcaagtgtat catatgccaa gtacgccccc tattgacgtc   12240
aatgacggta aatggcccgc ctggcattat gcccagtaca tgaccttatg ggactttcct   12300
acttggcagt acatctacgt attagtcatc gctattacca tggtgatgcg gttttggcag   12360
tacatcaatg ggcgtggata gcggtttgac tcacggggat ttccaagtct ccaccccatt   12420
gacgtcaatg ggagtttgtt ttggcaccaa aatcaacggg actttccaaa atgtcgtaac   12480
aactccgccc cattgacgca aatgggcggt aggcgtgtac ggtgggaggt ctatataagc   12540
agagctctct ggctaacagt ggcgcccgaa cagggacttg aaagcgaaag taaagccaga   12600
ggagatctct cgacgcagga ctcggcttgc tgaagcgcgc acggcaagag gcgaggggcg   12660
gcgactggtg agtacgccaa aaattttgac tagcggaggc tagaaggaga gatgggtg    12720 cgagagcgtc ggtattaagc gggggagaat tagataaatg ggaaaaaatt cggttaaggc   12780 caggggggaaa gaaacaatat aaactaaaac atatagtatg ggcaagcagg gagctagaac   12840
gattcgcagt taatcctggc cttttagaga catcagaagg ctgtagacaa atactgggac   12900
agctacaacc atcccttcag acaggatcag aagaacttag atcattatat aatacaaatag   12960 cagtcctcta ttgtgtgcat caaaggatag atgtaaaaga caccaaggaa gccttagata   13020
agatagagga gagcaaaaac aaaagtaaga aaaaggcaca gcaagcagca gctgacacag   13080
gaaacaacag ccaggtcagc caaaattacc ctatagtgca gaacctccag gggcaaatgg   13140
tacatcaggc catatcacct agaactttaa atgcatgggt aaaagtagta gaagagaagg   13200
ctttcagccc agaagtaata cccatgtttt cagcattatc agaaggagcc accccacaag   13260
atttaaatac catgctaaac acagtggggg gacatcaagc agccatgcaa atgttaaaag   13320
agaccatcaa tgaggaagct gcagaatggg atagattgca tccagtgcat gcagggccta   13380
ttgcaccagg ccagatgaga gaaccaaggg gaagtgacat agcaggaact actagtaccc   13440
ttcaggaaca aataggatgg atgacacata atccacctat cccagtagga gaaatctata   13500
aaagatggat aatcctggga ttaaataaaa tagtaagaat gtatagccct accagcattc   13560
tggacataag acaaggacca aaggaaccct ttagagacta tgtagaccga ttctataaaa   13620
ctctaagagc cgagcaagct tcacaagagg taaaaaattg gatgacagaa accttgttgg   13680
```

```
tccaaaatgc gaacccagat tgtaagacta ttttaaaagc attgggacca ggagcgacac    13740
tagaagaaat gatgacagca tgtcagggag tgggggacc cggccataaa gcaagagttt    13800
tggctgaagc aatgagccaa gtaacaaatc cagctaccat aatgatacag aaaggcaatt    13860
ttaggaacca agaaaagact gttaagtgtt tcaattgtgg caaagaaggg cacatagcca    13920
aaaattgcag gccccctagg aaaaagggct gttggaaatg tggaaaggaa ggacaccaaa    13980
tgaaagattg tactgagaga caggctaacc gcggagattg tactgagagt gcaccacgct    14040
tttcaattca attcatcatt ttttttttat tctttttttt gatttcggtt tctttgaaat    14100 tttttttgatt cggtaatctc cgaacagaag gaagaacgaa ggaaggagca cagacttaga    14160
ttggtatata tacgcatatg tagtgttgaa gaaacatgaa attgcccagt attcttaacc    14220
caactgcaca gaacaaaaac ctgcaggaaa cgaagataaa tcatgtcgaa agctacatat    14280
aaggaacgtg ctgctactca tcctagtcct gttgctgcca agctatttaa tatcatgcac    14340
gaaaagcaaa caaacttgtg tgcttcattg gatgttcgta ccaccaagga attactggag    14400
ttagttgaag cattaggtcc caaaatttgt ttactaaaaa cacatgtgga tatcttgact    14460
gatttttcca tggagggcac agttaagccg ctaaaggcat tatccgccaa gtacaatttt    14520
ttactcttcg aagacagaaa atttgctgac attggtaata cagtcaaatt gcagtactct    14580
gcgggtgtat acagaatagc agaatgggca gacattacga atgcacacgg tgtggtgggc    14640
ccaggtattg ttagcggttt gaagcaggcg gcagaagaag taacaaagga acctagaggc    14700
cttttgatgt tagcagaatt gtcatgcaag ggctccctat ctactggaga atatactaag    14760
ggtactgttg acattgcgaa gagcgacaaa gattttgtta tcggctttat tgctcaaaga    14820
gacatgggtg aagagatga aggttacgat tggttgatta tgcacaccgg tgtgggttta    14880
gatgacaagg gagacgcatt gggtcaacag tatagaaccg tggatgatgt ggtctctaca    14940
ggatctgaca ttattattgt tggaagagga ctatttgcaa agggaaggga tgctaaggta    15000
gagggtgaac gttacagaaa agcaggctgg gaagcatatt tgagaagatg cggccagcaa    15060
aactaaaaaa ctgtattata agtaaatgca tgtatactaa actcacaaat tagagcttca    15120
atttaattat atcagttatt accctgcggt gtgaaatacc gcacag                   15166

<210> SEQ ID NO 3
<211> LENGTH: 6453
<212> TYPE: DNA
<213> ORGANISM: Artificial Sequence
<220> FEATURE:
<223> OTHER INFORMATION: Plasmid sequence containing HIV-1, E-coli, and
      yeast sequences.

<400> SEQUENCE: 3
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacgggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
```

```
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctcg tctctctggt tagaccagat    840
ctgagcctgg gagctctctg gctaactagg gaacccactg cttaagcctc aataaagctt    900
gccttgagtg ctcaaagtag tgtgtgcccg tctgttgtgt gactctggta actagagatc    960
cctcagaccc ttttagtcag tgtggaaaat ctctagcagt ggcgcccgaa cagggacttg   1020
aaagcgaaag taaagccaga ggagatctct cgacgcagga ctcggcttgc tgaagcgcgc   1080
acggcaagag gcgagggggcg cgactggtg agtacgccaa aattttgac tagcggaggc   1140 tagaaggaga gagatgggtg cgagagcgtc ggtattaagc gggggagaat tagataaatg   1200
ggaaaaaatt cggttaaggc caggggggaaa gaaacaatat aaactaaaac atatagtatg   1260
ggcaagcagg gagctagaac gattcgcagt taatcctggc cttttagaga catcagaagg   1320
ctgtagacaa atactgggac agctacaacc atcccttcag acaggatcag aagaacttag   1380
atcattatat aatacaatag cagtcctcta ttgtgtgcat caaaggatag atgtaaaaga   1440
caccaaggaa gccttagata agatagagga agagcaaaac aaaagtaaga aaaaggcaca   1500
gcaagcagca gctgacacag gaaacaacag ccaggtcagc caaaattacc ctatagtgca   1560
gaacctccag gggcaaatgg tacatcaggc catatcacct agaactttaa atgcatgggt   1620
aaaagtagta gaagagaagg cttcagccc agaagtaata cccatgtttt cagcattatc   1680
agaaggagcc accccacaag atttaaatac catgctaaac acagtggggg gacatcaagc   1740
agccatgcaa atgttaaaag agaccatcaa tgaggaagct gcagaatggg atagattgca   1800
tccagtgcat gcagggccta ttgcaccagg ccagatgaga gaaccaaggg gaagtgacat   1860
agcaggaact actagtaccc ttcaggaaca aataggatgg atgacacata atccacctat   1920
cccagtagga gaaatctata aaagatggat aatcctggga ttaaataaaa tagtaagaat   1980
gtatagccct accagcattg tggcggccgc tcgagtctag agggcccgtt taaacccgct   2040
gatcagcctc gactgtgcct tctagttgcc agccatctgt tgtttgcccc tcccccgtgc   2100
cttccttgac cctggaaggt gccactccca ctgtcctttc ctaataaaat gaggaaattg   2160
catcgcattg tctgagtagg tgtcattcta ttctgggggg tggggtgggg caggacagca   2220
agggggagga ttgggaagac aatagcaggc atgctgggga tgcggtgggc tctatggctt   2280
ctgaggcgga agaaccagc tggggctcta ggggggtatcc ccacgcgccc tgtagcggcg   2340
cattaagcgc ggcgggtgtg gtggttacgc gcagcgtgac cgctacactt gccagcgccc   2400
tagcgcccgc tcctttcgct ttcttccctt cctttctcgc cacgttcgcc ggctttcccc   2460
gtcaagctct aaatcggggg ctcccttag ggttccgatt tagtgcttta cggcacctcg   2520
accccaaaaa acttgattag ggtgatggtt cacgtagtgg gccatcgccc tgatagacgg   2580
tttttcgccc tttgacgttg gagtccacgt tctttaatag tggactcttg ttccaaactg   2640
gaacaacact caaccctatc tcggtctatt cttttgattt ataagggatt ttgccgattt   2700
cggcctattg gttaaaaaat gagctgattt aacaaaaatt taacgcgaat taattctgtg   2760
gaatgtgtgt cagttagggt gtggaaagtc cccaggctcc ccagcaggca gaagtatgca   2820
aagcatgcat ctcaattagt cagcaaccag gtgtggaaag tccccaggct ccccagcagg   2880
cagaagtatg caaagcatgc atctcaatta gtcagcaacc atagtcccgc ccctaactcc   2940
```

```
gcccatcccg cccctaactc cgcccagttc cgcccattct ccgccccatg gctgactaat    3000 ttttttatt  tatgcagagg ccgaggccgc ctctgcctct gagctattcc agaagtagtg    3060
aggaggcttt tttggaggcc taggcttttg caaaaagctc ccgggagctt gtatatccat    3120
tttcggatct gatcaagaga caggatgagg atcgtttcgc atgattgaac aagatggatt    3180
gcacgcaggt tctccggccg cttgggtgga gaggctattc ggctatgact gggcacaaca    3240
gacaatcggc tgctctgatg ccgccgtgtt ccggctgtca gcgcagggc gcccggttct     3300 ttttgtcaag accgacctgt ccggtgccct gaatgaactg caggacgagg cagcgcggct    3360
atcgtggctg gccacgacgg gcgttccttg cgcagctgtg ctcgacgttg tcactgaagc    3420
gggaagggac tggctgctat tgggcgaagt gccggggcag atctcctgt catctcacct     3480 tgctcctgcc gagaaagtat ccatcatggc tgatgcaatg cggcggctgc atacgcttga    3540
tccggctacc tgcccattcg accaccaagc gaaacatcgc atcgagcgag cacgtactcg    3600
gatggaagcc ggtcttgtcg atcaggatga tctggacgaa gagcatcagg gctcgcgcc    3660 agccgaactg ttcgccaggc tcaaggcgcg catgcccgac ggcgaggatc tcgtcgtgac    3720
ccatggcgat gcctgcttgc cgaatatcat ggtggaaaat ggccgctttt ctggattcat    3780
cgactgtggc cggctgggtg tggcggaccg ctatcaggac atagcgttgg ctacccgtga    3840
tattgctgaa gagcttggcg gcgaatgggc tgaccgcttc ctcgtgcttt acggtatcgc    3900
cgctcccgat tcgcagcgca tcgccttcta tcgccttctt gacgagttct tctgagcggg    3960
actctggggt tcgaaatgac cgaccaagcg acgcccaacc tgccatcacg agatttcgat    4020
tccaccgccg ccttctatga aaggttgggc ttcggaatcg ttttccggga cgccggctgg    4080
atgatcctcc agcgcgggga tctcatgctg gagttcttcg cccacccaa cttgtttatt    4140 gcagcttata atggttacaa ataaagcaat agcatcacaa atttcacaaa taagcatt    4200 ttttcactgc attctagttg tggtttgtcc aaactcatca atgtatctta tcatgtctgt    4260
ataccgtcga cctctagcta gagcttggcg taatcatggt catagctgtt tcctgtgtga    4320
aattgttatc cgctcacaat tccacacaac atacgagccg aagcataaa gtgtaaagcc    4380 tggggtgcct aatgagtgag ctaactcaca ttaattgcgt tgcgctcact gcccgctttc    4440
cagtcgggaa acctgtcgtg ccagctgcat taatgaatcg gccaacgcgc ggggagaggc    4500
ggtttgcgta ttgggcgctc ttccgcttcc tcgctcactg actcgctgcg ctcggtcgtt    4560
cggctgcggc gagcggtatc agctcactca aaggcggtaa tacggttatc cacagaatca    4620
ggggataacg caggaaagaa catgtgagca aaaggccagc aaaaggccag gaaccgtaaa    4680
aaggccgcgt tgctggcgtt tttccatagg ctccgccccc ctgacgagca tcacaaaaat    4740
cgacgctcaa gtcagaggtg gcgaaacccg acaggactat aaagatacca ggcgtttccc    4800
cctggaagct ccctcgtgcg ctctcctgtt ccgaccctgc cgcttaccgg atacctgtcc    4860
gcctttctcc cttcgggaag cgtggcgctt tctcatagct cacgctgtag gtatctcagt    4920
tcggtgtagg tcgttcgctc caagctgggc tgtgtgcacg aaccccccgt tcagcccgac    4980
cgctgcgcct tatccggtaa ctatcgtctt gagtccaacc cggtaagaca cgacttatcg    5040
ccactggcag cagccactgg taacaggatt agcagagcga ggtatgtagg cggtgctaca    5100
gagttcttga agtggtggcc taactacggc tacactagaa gaacagtatt tggtatctgc    5160
gctctgctga agccagttac cttcggaaaa agagttggta gctcttgatc cggcaaacaa    5220
accaccgctg gtagcggttt ttttgtttgc aagcagcaga ttacgcgcag aaaaaaagga    5280
tctcaagaag atcctttgat cttttctacg gggtctgacg ctcagtggaa cgaaaactca    5340
```

-continued

```
cgttaaggga ttttggtcat gagattatca aaaggatct tcacctagat ccttttaaat      5400
taaaaatgaa gttttaaatc aatctaaagt atatatgagt aaacttggtc tgacagttac      5460
caatgcttaa tcagtgaggc acctatctca gcgatctgtc tatttcgttc atccatagtt      5520
gcctgactcc ccgtcgtgta gataactacg atacgggagg gcttaccatc tggccccagt      5580
gctgcaatga taccgcgaga cccacgctca ccggctccag atttatcagc aataaaccag      5640
ccagccggaa gggccgagcg cagaagtggt cctgcaactt tatccgcctc catccagtct      5700
attaattgtt gccgggaagc tagagtaagt agttcgccag ttaatagttt gcgcaacgtt      5760
gttgccattg ctacaggcat cgtggtgtca cgctcgtcgt ttggtatggc ttcattcagc      5820
tccggttccc aacgatcaag gcgagttaca tgatccccca tgttgtgcaa aaaagcggtt      5880
agctccttcg gtcctccgat cgttgtcaga agtaagttgg ccgcagtgtt atcactcatg      5940
gttatggcag cactgcataa ttctcttact gtcatgccat ccgtaagatg cttttctgtg      6000
actggtgagt actcaaccaa gtcattctga gaatagtgta tgcggcgacc gagttgctct      6060
tgcccggcgt caatacggga taataccgcg ccacatagca gaactttaaa agtgctcatc      6120
attggaaaac gttcttcggg gcgaaaactc tcaaggatct taccgctgtt gagatccagt      6180
tcgatgtaac ccactcgtgc acccaactga tcttcagcat cttttacttt caccagcgtt      6240
tctgggtgag caaaaacagg aaggcaaaat gccgcaaaaa agggaataag ggcgacacgg      6300
aaatgttgaa tactcatact cttcctttt caatattatt gaagcattta tcagggttat      6360
tgtctcatga gcggatacat atttgaatgt atttagaaaa ataaacaaat aggggttccg      6420
cgcacatttc cccgaaaagt gccacctgac gtc                                  6453
```

<210> SEQ ID NO 4
<211> LENGTH: 6322
<212> TYPE: DNA
<213> ORGANISM: Artificial Sequence
<220> FEATURE:
<223> OTHER INFORMATION: Plasmid sequence containing HIV-1, E-coli, and yeast sequences.

<400> SEQUENCE: 4

```
cgcgttggaa gggctaattt ggtcccaaaa aagacaagag atccttgatc tgtggatcta       60
ccacacacaa ggctacttcc ctgattggca gaactacaca ccagggccag ggatcagata      120
tccactgacc tttggatggt gcttcaagtt agtaccagtt gaaccagagc aagtagaaga      180
ggccaaataa ggagagaaga acagcttgtt acaccctatg agccagcatg ggatggagga      240
cccggaggga gaagtattag tgtggaagtt tgacagcctc ctagcatttc gtcacatggc      300
ccgagagctg catccggagt actacaaaga ctgctgacat cgagctttct acaagggact      360
ttccgctggg gactttccag ggaggtgtgg cctgggcggg actggggagt ggcgagccct      420
cagatgctac atataagcag ctgctttttg cctgtactgg gtctctctgg ttagaccaga      480
tctgagcctg ggagctctct ggctaactag ggaacccact gcttaagcct caataaagct      540
tgccttgagt gctcaaagta gtgtgtgccc gtctgttgtg tgactctggt aactagagat      600
ccctcagacc cttttagtca gtgtggaaaa tctctagcag tggcgcccga acaggactt      660 gaaagcgaaa gtaaagccag aggagatctc tcgacgcagg actcggcttg ctgaagcgcg      720
cacggcaaga ggcgaggggc ggcgactggt gagtacgcca aaattttga ctagcggagg      780 ctagaaggag agagatgggt gcgagagcgt cggtattaag cggggagaa ttagataaat      840 gggaaaaaat tcggttaagg ccaggggaa agaaacaata taaactaaaa catatagtat      900
gggcaagcag ggagctagaa cgattcgcag ttaatcctgg ccttttagag acatcagaag      960
```

```
gctgtagaca aatactggga cagctacaac catcccttca gacaggatca gaagaactta    1020
gatcattata taatacaata gcagtcctct attgtgtgca tcaaaggata gatgtaaaag    1080
acaccaagga agccttagat aagatagagg aagagcaaaa caaaagtaag aaaaaggcac    1140
agcaagcagc agctgacaca ggaaacaaca gccaggtcag ccaaaattac cctatagtgc    1200
agaacctcca ggggcaaatg gtacatcagg ccatatcacc tagaacttta aatgcatggg    1260
taaaagtagt agaagagaag gctttcagcc cagaagtaat acccatgttt tcagcattat    1320
cagaaggagc cacccacaa gatttaaata ccatgctaaa cacagtgggg ggacatcaag    1380
cagccatgca aatgttaaaa gagaccatca atgaggaagc tgcagaatgg gatagattgc    1440
atccagtgca tgcagggcct attgcaccag gccagatgag agaaccaagg ggaagtgaca    1500
tagcaggaac tactagtacc cttcaggaac aaataggatg gatgacacat aatccaccta    1560
tcccagtagg agaaatctat aaaagatgga taatcctggg attaaataaa atagtaagaa    1620
tgtatagccc taccagcatt gtggcggccg ctcgagtcta gagggcccgt ttaaacccgc    1680
tgatcagcct cgactgtgcc ttctagttgc cagccatctg ttgtttgccc ctcccccgtg    1740
ccttccttga ccctggaagg tgccactccc actgtccttt cctaataaaa tgaggaaatt    1800
gcatcgcatt gtctgagtag gtgtcattct attctggggg gtggggtggg caggacagc    1860 aaggggagg attgggaaga caatagcagg catgctgggg atgcggtggg ctctatggct    1920
tctgaggcgg aaagaaccag ctggggctct agggggtatc cccacgcgcc ctgtagcggc    1980
gcattaagcg cggcgggtgt ggtggttacg cgcagcgtga ccgctacact tgccagcgcc    2040
ctagcgcccg ctcctttcgc tttcttccct tcctttctcg ccacgttcgc cggctttccc    2100
cgtcaagctc taaatcgggg gctcccttta gggttccgat ttagtgcttt acggcacctc    2160
gaccccaaaa aacttgatta gggtgatggt tcacgtagtg gccatcgcc tgatagacg    2220 gtttttcgcc ctttgacgtt ggagtccacg ttctttaata gtggactctt gttccaaact    2280
ggaacaacac tcaaccctat ctcggtctat tcttttgatt tataagggat tttgccgatt    2340
tcggcctatt ggttaaaaaa tgagctgatt taacaaaaat ttaacgcgaa ttaattctgt    2400
ggaatgtgtg tcagttaggg tgtggaaagt ccccaggctc cccagcaggc agaagtatgc    2460
aaagcatgca tctcaattag tcagcaacca ggtgtggaaa gtccccaggc tcccagcag    2520 gcagaagtat gcaaagcatg catctcaatt agtcagcaac catagtcccg cccctaactc    2580
cgcccatccc gcccctaact ccgcccagtt ccgcccattc tccgcccat ggctgactaa    2640 tttttttat ttatgcagag gccgaggccg cctctgcctc tgagctattc cagaagtagt    2700
gaggaggctt ttttggaggc ctaggctttt gcaaaaagct cccgggagct tgtatatcca    2760
ttttcggatc tgatcaagag acaggatgag gatcgtttcg catgattgaa caagatggat    2820
tgcacgcagg ttctccggcc gcttgggtgg agaggctatt cggctatgac tgggcacaac    2880
agacaatcgg ctgctctgat gccgccgtgt tccggctgtc agcgcagggg cgcccggttc    2940
tttttgtcaa gaccgacctg tccggtgccc tgaatgaact gcaggacgag gcagcgcggc    3000
tatcgtggct ggccacgacg ggcgttcctt gcgcagctgt gctcgacgtt gtcactgaag    3060
cgggaaggga ctggctgcta ttgggcgaag tgccggggca ggatctcctg tcatctcacc    3120
ttgctcctgc cgagaaagta tccatcatgg ctgatgcaat gcggcggctg catacgcttg    3180
atccggctac ctgcccattc gaccaccaag cgaaacatcg catcgagcga gcacgtactc    3240
ggatggaagc cggtcttgtc gatcaggatg atctggacga agagcatcag gggctcgcgc    3300
cagccgaact gttcgccagg ctcaaggcgc gcatgcccga cggcgaggat ctcgtcgtga    3360
```

```
cccatggcga tgcctgcttg ccgaatatca tggtggaaaa tggccgcttt tctggattca   3420
tcgactgtgg ccggctgggt gtggcggacc gctatcagga catagcgttg gctacccgtg   3480
atattgctga agagcttggc ggcgaatggg ctgaccgctt cctcgtgctt tacggtatcg   3540
ccgctcccga ttcgcagcgc atcgccttct atcgccttct tgacgagttc ttctgagcgg   3600
gactctgggg ttcgaaatga ccgaccaagc gacgcccaac ctgccatcac gagatttcga   3660
ttccaccgcc gccttctatg aaaggttggg cttcggaatc gttttccggg acgccggctg   3720
gatgatcctc cagcgcgggg atctcatgct ggagttcttc gcccacccca acttgtttat   3780
tgcagcttat aatggttaca aataaagcaa tagcatcaca aatttcacaa ataaagcatt   3840
tttttcactg cattctagtt gtggtttgtc caaactcatc aatgtatctt atcatgtctg   3900
tataccgtcg acctctagct agagcttggc gtaatcatgg tcatagctgt ttcctgtgtg   3960
aaattgttat ccgctcacaa ttccacacaa catacgagcc ggaagcataa agtgtaaagc   4020
ctggggtgcc taatgagtga gctaactcac attaattgcg ttgcgctcac tgcccgcttt   4080
ccagtcggga aacctgtcgt gccagctgca ttaatgaatc ggccaacgcg cggggagagg   4140
cggtttgcgt attgggcgct cttccgcttc ctcgctcact gactcgctgc gctcggtcgt   4200
tcggctgcgg cgagcggtat cagctcactc aaaggcggta atacggttat ccacagaatc   4260
aggggataac gcaggaaaga acatgtgagc aaaaggccag caaaaggcca ggaaccgtaa   4320
aaaggccgcg ttgctggcgt ttttccatag gctccgcccc cctgacgagc atcacaaaaa   4380
tcgacgctca agtcagaggt ggcgaaaccc gacaggacta taaagatacc aggcgtttcc   4440
ccctggaagc tccctcgtgc gctctcctgt tccgaccctg ccgcttaccg gatacctgtc   4500
cgcctttctc ccttcgggaa gcgtggcgct ttctcatagc tcacgctgta ggtatctcag   4560
ttcggtgtag gtcgttcgct ccaagctggg ctgtgtgcac gaaccccccg ttcagcccga   4620
ccgctgcgcc ttatccggta actatcgtct gagtccaac ccgtaagac acgacttatc   4680 gccactggca gcagccactg gtaacaggat tagcagagcg aggtatgtag gcggtgctac   4740
agagttcttg aagtggtggc ctaactacgg ctacactaga agaacagtat ttggtatctg   4800
cgctctgctg aagccagtta ccttcggaaa aagagttggt agctcttgat ccggcaaaca   4860
aaccaccgct ggtagcggtt ttttgtttg caagcagcag attacgcgca gaaaaaaagg   4920
atctcaagaa gatcctttga tcttttctac ggggtctgac gctcagtgga acgaaaactc   4980
acgttaaggg attttggtca tgagattatc aaaaaggatc ttcacctaga tccttttaaa   5040
ttaaaaatga agttttaaat caatctaaag tatatatgag taaacttggt ctgacagtta   5100
ccaatgctta atcagtgagg cacctatctc agcgatctgt ctatttcgtt catccatagt   5160
tgcctgactc cccgtcgtgt agataactac gatacgggag ggcttaccat ctggccccag   5220
tgctgcaatg ataccgcgag acccacgctc accggctcca gatttatcag caataaacca   5280
gccagccgga agggccgagc gcagaagtgg tcctgcaact ttatccgcct ccatccagtc   5340
tattaattgt tgccgggaag ctagagtaag tagttcgcca gttaatagtt tgcgcaacgt   5400
tgttgccatt gctacaggca tcgtggtgtc acgctcgtcg tttggtatgg cttcattcag   5460
ctccggttcc caacgatcaa ggcgagttac atgatccccc atgttgtgca aaaaagcggt   5520
tagctccttc ggtcctccga tcgttgtcag aagtaagttg gccgcagtgt tatcactcat   5580
ggttatggca gcactgcata attctcttac tgtcatgcca tccgtaagat gcttttctgt   5640
gactggtgag tactcaacca agtcattctg agaatagtgt atgcggcgac cgagttgctc   5700
ttgcccggcg tcaatacggg ataataccgc gccacatagc agaactttaa aagtgctcat   5760
```

```
cattggaaaa cgttcttcgg ggcgaaaact ctcaaggatc ttaccgctgt tgagatccag   5820
ttcgatgtaa cccactcgtg cacccaactg atcttcagca tcttttactt tcaccagcgt   5880
ttctgggtga gcaaaaacag gaaggcaaaa tgccgcaaaa aagggaataa gggcgacacg   5940
gaaatgttga atactcatac tcttcctttt tcaatattat tgaagcattt atcagggtta   6000
ttgtctcatg agcggataca tatttgaatg tatttagaaa aataaacaaa taggggttcc   6060
gcgcacattt ccccgaaaag tgccacctga cgtcgacgga tcgggagatc tcccgatccc   6120
ctatggtgca ctctcagtac aatctgctct gatgccgcat agttaagcca gtatctgctc   6180
cctgcttgtg tgttggaggt cgctgagtag tgcgcgagca aaatttaagc tacaacaagg   6240
caaggcttga ccgacaattg catgaagaat ctgcttaggg ttaggcgttt tgcgctgctt   6300
cgcgatgtac gggccagata ta                                            6322
```

<210> SEQ ID NO 5
<211> LENGTH: 17977
<212> TYPE: DNA
<213> ORGANISM: Artificial Sequence
<220> FEATURE:
<223> OTHER INFORMATION: Plasmid sequence containing HIV-1, E-coli, and
      yeast sequences.

<400> SEQUENCE: 5

```
gatccttagc acttatctgg gacgatctgc ggagcctgtg cctcttcagc taccaccgct     60
tgagagactt actcttgatt gtaacgagga ttgtggaact tctgggacgc agggggtggg    120
aagccctcaa atattggtgg aatctcctac agtattggag tcaggaacta agaatagtg    180 ctgttaactt gctcaatgcc acagcctag cagtagctga ggggacagat agggttatag     240
aagtattaca agcagcttat agagctattc gccacatacc tagaagaata agacagggct    300
tggaaaggat tttgctataa accgggcgcc accatggctt ccaaggtgta cgaccccgag    360
caacgcaaac gcatgatcac tgggcctcag tggtgggctc gctgcaagca aatgaacgtg    420
ctggactcct tcatcaacta ctatgattcc gagaagcacg ccgagaacgc cgtgattttt    480
ctgcatggta acgctgcctc cagctacctg tggaggcacg tcgtgcctca catcgagccc    540
gtggctagat gcatcatccc tgatctgatc ggaatgggta agtccggcaa gagcgggaat    600
ggctcatatc gcctcctgga tcactacaag tacctcaccg cttggttcga gctgctgaac    660
cttccaaaga aaatcatctt tgtgggccac gactgggggg cttgtctggc ctttcactac    720
tcctacgagc accaagacaa gatcaaggcc atcgtccatg ctgagagtgt cgtggacgtg    780
atcgagtcct gggacgagtg gcctgacatc gaggaggata tcgccctgat caagagcgaa    840
gagggcgaga aaatggtgct tgagaataac ttcttcgtcg agaccatgct cccaagcaag    900
atcatgcgga aactggagcc tgaggagttc gctgcctacc tggagccatt caaggagaag    960
ggcgaggtta gacggcctac cctctcctgg cctcgcgaga tccctctcgt taagggaggc   1020
aagcccgacg tcgtccagat tgtccgcaac tacaacgcct accttcgggc cagcgacgat   1080
ctgcctaaga tgttcatcga gtccgaccct gggttctttt ccaacgctat tgtcgaggga   1140
gctaagaagt tccctaacac cgagttcgtg aaggtgaagg gcctccactt cagccaggag   1200
gacgctccag atgaaatggg taagtacatc aagagcttcg tggagcgcgt gctgaagaac   1260
gagcagtaaa gcggccgcat gggtggcaag tggtcaaaaa gtagtgtgat tggatggcct   1320
gctgtaaggg aaagaatgag acgagctgag ccagcagcag atggggtggg agcagtatct   1380
cgagacctag aaaaacatgg agcaatcaca agtagcaata cagcagctaa caatgctgct   1440
```

```
tgtgcctggc tagaagcaca agaggaggaa gaggtgggtt ttccagtcac acctcaggta   1500
cctttaagac caatgactta caaggcagct gtagatctta gccactttt aaaagaaaag    1560 gggggactgg aagggctaat tcactcccaa agaagacaag atatccttga tctgtggatc   1620
taccacacac aaggctactt ccctgattgg cagaactaca caccagggcc aggggtcaga   1680
tatccactga cctttggatg gtgctacaag ctagtaccag ttgagccaga taaggtagaa   1740
gaggccaata aggagagaa caccagcttg ttacaccctg tgagcctgca tggaatggat     1800
gaccctgaga gagaagtgtt agagtggagg tttgacagcc gcctagcatt tcatcacgtg   1860
gcccgagagc tgcatccgga gtacttcaag aactgctgac atcgagcttg ctacaaggga   1920
ctttccgctg gggactttcc agggaggcgt ggcctgggcg ggactgggga gtggcgagcc   1980
ctcagatgct gcatataagc agctgctttt tgcctgtact gggtctctct ggttagacca   2040
gatctgagcc tgggagctct ctggctaact agggaaccca ctgcttaagc ctcaataaag   2100
cttgccttga gtgcttcaag tagtgtgtgc ccgtctgttg tgtgactctg gtaactagag   2160
atccctcaga ccctttagt cagtgtggaa aatctctagc actcgagtct agaccctcga    2220
ggagaacttc tagtatatcc acatacctaa tattattgcc ttattaaaaa tggaatccca   2280
acaattacat caaaatccac attctcttca aaatcaattg tcctgtactt ccttgttcat   2340
gtgtgttcaa aaacgttata tttataggat aattatactc tatttctcaa caagtaattg   2400
gttgtttggc cgagcggtct aaggcgcctg attcaagaaa tatcttgacc gcagttaact   2460
gtgggaatac tcaggtatcg taagatgcaa gagttcgaat ctcttagcaa ccattatttt   2520
tttcctcaac ataacgagaa cacacagggg cgctatcgca cagaatcaaa ttcgatgact   2580
ggaaattttt tgttaatttc agaggtcgcc tgacgcatat accttttca actgaaaaat     2640 tgggagaaaa aggaaaggtg agaggccgga accggctttt catatagaat agagaagcgt   2700
tcatgactaa atgcttgcat cacaatactt gaagttgaca atattattta aggacctatt   2760
gttttttcca ataggtggtt agcaatcgtc ttactttcta actttctta ccttttacat     2820 ttcagcaata tatatata tttcaaggat ataccattct aatgtctgcc cctatgtctg     2880
cccctaagaa gatcgtcgtt ttgccaggtg accacgttgg tcaagaaatc acagccgaag   2940
ccattaaggt tcttaaagct atttctgatg ttcgttccaa tgtcaagttc gatttcgaaa   3000
atcatttaat tggtggtgct gctatcgatg ctacaggtgt cccacttcca gatgaggcgc   3060
tggaagcctc caagaaggtt gatgccgttt tgttaggtgc tgtgggtggt cctaaatggg   3120
gtaccggtag tgttagacct gaacaaggtt tactaaaaat ccgtaaagaa cttcaattgt   3180
acgccaactt aagaccatgt aactttgcat ccgactctct tttagactta tctccaatca   3240
agccacaatt tgctaaaggt actgacttcg ttgttgtcag agaattagtg ggaggtattt   3300
actttggtaa gagaaaggaa gacgatggtg atggtgtcgc ttgggatagt gaacaataca   3360
ccgttccaga agtgcaaaga atcacaagaa tggccgcttt catggcccta caacatgagc   3420
caccattgcc tatttggtcc ttggataaag ctaatgtttt ggcctcttca agattatgga   3480
gaaaaactgt ggaggaaacc atcaagaacg aattccctac attgaaggtt caacatcaat   3540
tgattgattc tgccgccatg atcctagtta agaacccaac ccacctaaat ggtattataa   3600
tcaccagcaa catgtttggt gatatcatct ccgatgaagc ctccgttatc ccaggttcct   3660 tgggttttgtt gccatctgcg tccttggcct cttttgccaga caagaacacc gcatttggtt   3720
tgtacgaacc atgccacggt tctgctccag atttgccaaa gaataaggtt gaccctatcg   3780
ccactatctt gtctgctgca atgatgttga aattgtcatt gaacttgcct gaagaaggta   3840
```

```
aggccattga agatgcagtt aaaaaggttt tggatgcagg tatcagaact ggtgatttag    3900
gtggttccaa cagtaccacc gaagtcggtg atgctgtcgc cgaagaagtt aagaaaatcc    3960
ttgcttaaaa agattctctt tttttatgat atttgtacat aaactttata aatgaaattc    4020
ataatagaaa cgacacgaaa ttacaaaatg gaatatgttc atagggtaga cgaaactata    4080
tacgcaatct acatacattt atcaagaagg agaaaaagga ggatagtaaa ggaatacagg    4140
taagcaaatt gatactaatg gctcaacgtg ataaggaaaa agaattgcac tttaacatta    4200
atattgacaa ggaggagggc accacacaaa aagttaggtg taacagaaaa tcatgaaact    4260
acgattccta atttgatatt ggaggatttt ctctaaaaaa aaaaaaatac aacaaataaa    4320
aaacactcaa tgacctgacc atttgatgga gtttaagtca ataccttctt gaaccatttc    4380
ccataatggt gaaagttccc tcaagaattt tactctgtca gaaacggcct tacgacgtag    4440
tcgatatggt gcactctcag tacaatctgc tctgatgccg catagttaag ccagccccga    4500
cacccgccaa cacccgctga cgcgcccctga cgggcttgtc tgctcccggc atccgcttac    4560
agacaagctg tgaccgtctc cgggagctgc atgtgtcaga ggttttcacc gtcatcaccg    4620
aaacgcgcga gacgaaaggg cctcgtgata cgcctatttt tataggttaa tgtcatgata    4680
ataatggttt cttaggacgg atcgcttgcc tgtaacttac acgcgcctcg tatctttttaa    4740 tgatggaata atttgggaat ttactctgtg tttatttatt tttatgtttt gtatttggat    4800
tttagaaagt aaataaagaa ggtagaagag ttacggaatg aagaaaaaaa aataaacaaa    4860
ggtttaaaaa atttcaacaa aaagcgtact ttacatatat atttattaga caagaaaagc    4920
agattaaata gatatacatt cgattaacga taagtaaaat gtaaaatcac aggattttcg    4980
tgtgtggtct tctacacaga caagatgaaa caattcggca ttaatacctg agagcaggaa    5040
gagcaagata aaaggtagta tttgttggcg atccccctag agtcttttac atcttcggaa    5100
aacaaaaact atttttttctt taatttctttt ttttacttttc tatttttaat ttatatattt    5160
atattaaaaa atttaaatta taattatttt tatagcacgt gatgaaaagg acccaggtgg    5220
cacttttcgg ggaaatgtgc gcggaacccc tatttgttta tttttctaaa tacattcaaa    5280
tatgtatccg ctctagaggg cccgtttaaa cccgctgatc agcctcgact gtgccttcta    5340
gttgccagcc atctgttgtt tgcccctccc ccgtgccttc cttgaccctg gaaggtgcca    5400
ctcccactgt cctttcctaa taaaatgagg aaattgcatc gcattgtctg agtaggtgtc    5460
attctattct ggggggtggg gtggggcagg acagcaaggg ggaggattgg gaagacaata    5520
gcaggcatgc tggggatgcg gtgggctcta tggcttctga gcggaaaga accagctggg    5580 gctctagggg gtatccccac gcgccctgta gcggcgcatt aagcgcggcg ggtgtggtgg    5640
ttacgcgcag cgtgaccgct acacttgcca gcgccctagc gcccgctcct ttcgctttct    5700
tcccttcctt tctcgccacg ttcgccggct ttccccgtca gctctaaat cggggcatcc    5760 ctttagggtt ccgatttagt gctttacggc acctcgaccc caaaaaactt gattagggtg    5820
atggttcacg tagtgggcca tcgccctgat agacggtttt tcgcccttttg acgttggagt    5880 ccacgttctt taatagtgga ctcttgttcc aaactggaac aacactcaac cctatctcgg    5940
tctattcttt tgatttataa gggattttgg ggatttcggc ctattggtta aaaaatgagc    6000
tgatttaaca aaaatttaac gcgaattaat tctgtggaat gtgtgtcagt tagggtgtgg    6060
aaagtcccca ggctcccag gcaggcagaa gtatgcaaag catgcatctc aattagtcag    6120
caaccaggtg tggaaagtcc ccaggctccc cagcaggcag aagtatgcaa agcatgcatc    6180
tcaattagtc agcaaccata gtcccgcccc taactccgcc catcccgccc ctaactccgc    6240
```

```
ccagttccgc ccattctccg ccccatggct gactaatttt ttttatttat gcagaggccg   6300
aggccgcctc tgcctctgag ctattccaga agtagtgagg aggctttttt ggaggcctag   6360
gcttttgcaa aaagctcccg ggagcttgta tatccatttt cggatctgat cagcacgtgt   6420
tgacaattaa tcatcggcat agtatatcgg catagtataa tacgacaagg tgaggaacta   6480
aaccatggcc aagttgacca gtgccgttcc ggtgctcacc gcgcgcgacg tcgccggagc   6540
ggtcgagttc tggaccgacc ggctcgggtt ctcccgggac ttcgtggagg acgacttcgc   6600
cggtgtggtc cgggacgacg tgaccctgtt catcagcgcg gtccaggacc aggtggtgcc   6660
ggacaacacc ctggcctggg tgtgggtgcg cggcctggac gagctgtacg ccgagtggtc   6720
ggaggtcgtg tccacgaact tccgggacgc ctccgggccg gccatgaccg agatcggcga   6780
gcagccgtgg gggcgggagt tcgccctgcg cgacccggcc ggcaactgcg tgcacttcgt   6840
ggccgaggag caggactgac acgtgctacg agatttcgat tccaccgccg ccttctatga   6900
aaggttgggc ttcggaatcg ttttccggga cgccggctgg atgatcctcc agcgcgggga   6960
tctcatgctg gagttcttcg cccaccccaa cttgtttatt gcagcttata atggttacaa   7020
ataaagcaat agcatcacaa atttcacaaa taaagcattt ttttcactgc attctagttg   7080
tggtttgtcc aaactcatca atgtatctta tcatgtctgt ataccgtcga cctctagcta   7140
gagcttggcg taatcatggt catagctgtt tcctgtgtga aattgttatc cgctcacaat   7200
tccacacaac atacgagccg gaagcataaa gtgtaaagcc tggggtgcct aatgagtgag   7260
ctaactcaca ttaattgcgt tgcgctcact gcccgctttc cagtcgggaa acctgtcgtg   7320
ccagctgcat taatgaatcg gccaacgcgc ggggagaggc ggtttgcgta ttgggcgctc   7380
ttccgcttcc tcgctcactg actcgctgcg ctcggtcgtt cggctgcggc gagcggtatc   7440
agctcactca aaggcggtaa tacggttatc cacagaatca ggggataacg caggaaagaa   7500
catgtgagca aaaggccagc aaaaggccag gaaccgtaaa aaggccgcgt tgctggcgtt   7560
tttccatagg ctccgccccc ctgacgagca tcacaaaaat cgacgctcaa gtcagaggtg   7620
gcgaaacccg acaggactat aaagatacca ggcgtttccc cctggaagct ccctcgtgcg   7680
ctctcctgtt ccgaccctgc cgcttaccgg atacctgtcc gcctttctcc cttcgggaag   7740
cgtggcgctt tctcaatgct cacgctgtag gtatctcagt tcggtgtagg tcgttcgctc   7800
caagctgggc tgtgtgcacg aaccccccgt tcagcccgac cgctgcgcct tatccggtaa   7860
ctatcgtctt gagtccaacc cggtaagaca cgacttatcg ccactggcag cagccactgg   7920
taacaggatt agcagagcga ggtatgtagg cggtgctaca gagttcttga agtggtggcc   7980
taactacggc tacactagaa ggacagtatt tggtatctgc gctctgctga agccagttac   8040
cttcggaaaa agagttggta gctcttgatc cggcaaacaa accaccgctg gtagcggtgg   8100
tttttttgtt tgcaagcagc agattacgcg cagaaaaaaa ggatctcaag aagatccttt   8160
gatcttttct acgggtctg acgctcagtg aacgaaaac tcacgttaag ggattttggt   8220
catgagatta tcaaaaagga tcttcaccta gatccttta aattaaaaat gaagttttaa   8280
atcaatctaa agtatatatg agtaaacttg gtctgacagt taccaatgct taatcagtga   8340
ggcacctatc tcagcgatct gtctatttcg ttcatccata gttgcctgac tccccgtcgt   8400
gtagataact acgatacggg agggcttacc atctggcccc agtgctgcaa tgataccgcg   8460
agacccacgc tcaccggctc cagatttatc agcaataaac cagccagccg aagggccga   8520 gcgcagaagt ggtcctgcaa ctttatccgc ctccatccag tctattaatt gttgccggga   8580
agctagagta agtagttcgc cagttaatag tttgcgcaac gttgttgcca ttgctacagg   8640
```

```
catcgtggtg tcacgctcgt cgtttggtat ggcttcattc agctccggtt cccaacgatc    8700
aaggcgagtt acatgatccc ccatgttgtg caaaaaagcg gttagctcct tcggtcctcc    8760
gatcgttgtc agaagtaagt tggccgcagt gttatcactc atggttatgg cagcactgca    8820
taattctctt actgtcatgc catccgtaag atgcttttct gtgactggtg agtactcaac    8880
caagtcattc tgagaatagt gtatgcggcg accgagttgc tcttgcccgg cgtcaatacg    8940
ggataatacc gcgccacata gcagaacttt aaaagtgctc atcattggaa aacgttcttc    9000
ggggcgaaaa ctctcaagga tcttaccgct gttgagatcc agttcgatgt aacccactcg    9060
tgcacccaac tgatcttcag catcttttac tttcaccagc gtttctgggt gagcaaaaac    9120
aggaaggcaa aatgccgcaa aaaagggaat aagggcgaca cggaaatgtt gaatactcat    9180
actcttcctt tttcaatatt attgaagcat ttatcagggt tattgtctca tgagcggata    9240
catatttgaa tgtatttaga aaaataaaca aataggggtt ccgcgcacat ttccccgaaa    9300
agtgccacct gacgtcgacg gatcgggaga tctcccgatc ccctatggtc gactctcagt    9360
acaatctgct ctgatgccgc atagttaagc cagtatctgc tccctgcttg tgtgttggag    9420
gtcgctgagt agtgcgcgag caaaatttaa gctacaacaa ggcaaggctt gaccgacaat    9480
tgcatgaaga atctgcttag ggttaggcgt tttgcgctgc ttcgcgatgt acgggccaga    9540
tatacgcgtt gacattgatt attgactagt tattaatagt aatcaattac ggggtcatta    9600
gttcatagcc catatatgga gttccgcgtt acataactta cggtaaatgg cccgcctggc    9660
tgaccgccca acgaccccg cccattgacg tcaataatga cgtatgttcc catagtaacg    9720
ccaataggga ctttccattg acgtcaatgg gtggactatt tacggtaaac tgcccacttg    9780
gcagtacatc aagtgtatca tatgccaagt acgccccta ttgacgtcaa tgacggtaaa    9840
tggcccgcct ggcattatgc ccagtacatg accttatggg actttcctac ttggcagtac    9900
atctacgtat tagtcatcgc tattaccatg gtgatgcggt tttggcagta catcaatggg    9960
cgtggatagc ggtttgactc acggggattt ccaagtctcc accccattga cgtcaatggg   10020
agtttgtttt ggcaccaaaa tcaacgggac tttccaaaat gtcgtaacaa ctccgcccca   10080
ttgacgcaaa tgggcggtag gcgtgtacgg tgggaggtct atataagcag agctctctgg   10140
ctaacagtgg cgcccgaaca gggacttgaa agcgaaagta agccagagg agatctctcg    10200 acgcaggact cggcttgctg aagcgcgcac ggcaagaggc gaggggcggc gactggtgag   10260
tacgccaaaa attttgacta gcggaggcta gaaggagaga gatgggtgcg agagcgtcgg   10320
tattaagcgg ggagaatta gataaatggg aaaaaattcg gttaaggcca gggggaaaga   10380
aacaatataa actaaaacat atagtatggg caagcaggga gctagaacga ttcgcagtta   10440
atcctggcct tttagagaca tcagaaggct gtagacaaat actgggacag ctacaaccat   10500
cccttcagac aggatcagaa gaacttagat cattatataa tacaatagca gtcctctatt   10560
gtgtgcatca aaggatagat gtaaaagaca ccaaggaagc cttagataag atagaggaag   10620
agcaaaacaa aagtaagaaa aaggcacagc aagcagcagc tgacacagga aacaacagcc   10680
aggtcagcca aaattaccct atagtgcaga acctccaggg gcaaatggta catcaggcca   10740
tatcacctag aactttaaat gcatgggtaa aagtagtaga agagaaggct ttcagcccag   10800
aagtaatacc catgttttca gcattatcag aaggagccac cccacaagat ttaaatacca   10860
tgctaaacac agtgggggga catcaagcag ccatgcaaat gttaaaagag accatcaatg   10920
aggaagctgc agaatgggat agattgcatc cagtgcatgc agggcctatt gcaccaggcc   10980
agatgagaga accaagggga agtgacatag caggaactac tagtacccct tcaggaacaaa   11040
```

```
taggatggat gacacataat ccacctatcc cagtaggaga atctataaa agatggataa   11100 tcctgggatt aaataaaata gtaagaatgt atagccctac cagcattctg gacataagac   11160
aaggaccaaa ggaacccttt agagactatg tagaccgatt ctataaaact ctaagagccg   11220
agcaagcttc acaagaggta aaaaattgga tgacagaaac cttgttggtc caaaatgcga   11280
acccagattg taagactatt ttaaaagcat tgggaccagg agcgacacta gaagaaatga   11340
tgacagcatg tcagggagtg gggggacccg gccataaagc aagagttttg gctgaagcaa   11400
tgagccaagt aacaaatcca gctaccataa tgatacagaa aggcaatttt aggaaccaaa   11460
gaaagactgt taagtgtttc aattgtggca agaagggca catagccaaa aattgcaggg   11520
cccctaggaa aaagggctgt tggaaatgtg gaaaggaagg acaccaaatg aaagattgta   11580
ctgagagaca ggctaatttt ttagggaaga tctggccttc ccacaaggga aggccaggga   11640
attttcttca gagcagacca gagccaacag ccccaccaga agagagcttc aggtttgggg   11700
aagagacaac aactccctct cagaagcagg agccgataga caaggaactg tatcctttag   11760
cttccctcag atcactcttt ggcagcgacc cctcgtcaca ataaagatag gggggcaatt   11820
aaaggaagct ctattagata caggagcaga tgatacagta ttagaagaaa tgaatttgcc   11880
aggaagatgg aaaccaaaaa tgatagggg aattggaggt tttatcaaag taggacagta   11940
tgatcagata ctcatagaaa tctgcggaca taaagctata ggtacagtat tagtaggacc   12000
tacacctgtc aacataattg gaagaaatct gttgactcag attggctgca ctttaaattt   12060
tcccattagt cctattgaga ctgtaccagt aaaattaaag ccaggaatgg atggcccaaa   12120
agttaaacaa tggccattga cagaagaaaa aataaaagca ttagtagaaa tttgtacaga   12180
aatggaaaag gaaggaaaaa tttcaaaaat tgggcctgaa aatccataca atactccagt   12240
atttgccata agaaaaaag acagtactaa atggagaaaa ttagtagatt tcagagaact   12300
taataagaga actcaagatt tctgggaagt tcaattagga ataccacatc ctgcagggtt   12360
aaaacagaaa aaatcagtaa cagtactgga tgtgggcgat gcatattttt cagttccctt   12420
agataaagac ttcaggaagt atactgcatt taccatacct agtataaaca atgagacacc   12480
agggattaga tatcagtaca atgtgcttcc acagggatgg aaaggatcac cagcaatatt   12540
ccagtgtagc atgacaaaaa tcttagagcc ttttagaaaa caaaatccag acatagtcat   12600
ctatcaatac atggatgatt tgtatgtagg atctgactta gaaatagggc agcatagaac   12660
aaaaatagag gaactgagac aacatctgtt gaggtgggga tttaccacac cagacaaaaa   12720
acatcagaaa gaacctccat tcctttggat gggttatgaa ctccatcctg ataaatggac   12780
agtacagcct atagtgctgc cagaaaagga cagctggact gtcaatgaca tacagaaatt   12840
agtgggaaaa ttgaattggg caagtcagat ttatgcaggg attaaagtaa ggcaattatg   12900
taaacttctt aggggaacca agcactaac agaagtagta ccactaacag aagaagcaga   12960
gctagaactg gcagaaaaca gggagattct aaaagaaccg gtacatggag tgtattatga   13020
cccatcaaaa gacttaatag cagaaataca gaagcagggg caaggccaat ggacatatca   13080
aatttatcaa gagccattta aaaatctgaa aacaggaaaa tatgcaagaa tgaagggtgc   13140
ccacactaat gatgtgaaac aattaacaga gcagtacaa aaaatagcca cagaaagcat   13200
agtaatatgg ggaaagactc ctaaatttaa attacccata caaaaggaaa catgggaagc   13260
atggtggaca gagtattggc aagccacctg gattcctgag tgggagtttg tcaatacccc   13320
tcccttagtg aagttatggt accagttaga gaaagaaccc ataataggag cagaaacttt   13380
ctatgtagat ggggcagcca atagggaaac taaattagga aaagcaggat atgtaactga   13440
```

```
cagaggaaga caaaaagttg tcccctaac ggacacaaca atcagaaga ctgagttaca    13500 agcaattcat ctagctttgc aggattcggg attagaagta aacatagtga cagactcaca    13560
atatgcattg ggaatcattc aagcacaacc agataagagt gaatcagagt tagtcagtca    13620
aataatagag cagttaataa aaaggaaaa agtctacctg gcatgggtac cagcacacaa    13680
aggaattgga ggaaatgaac aagtagatgg gttggtcagt gctggaatca ggaaagtact    13740
atttttagat ggaatagata aggcccaaga agaacatgag aaatatcaca gtaattggag    13800
agcaatggct agtgatttta acctaccacc tgtagtagca aaagaaatag tagccagctg    13860
tgataaatgt cagctaaaag gggaagccat gcatggacaa gtagactgta gcccaggaat    13920
atggcagcta gattgtacac atttagaagg aaaagttatc ttggtagcag ttcatgtagc    13980
cagtggatat atagaagcag aagtaattcc agcagagaca gggcaagaaa cagcatactt    14040
cctcttaaaa ttagcaggaa gatggccagt aaaaacagta catacagaca atggcagcaa    14100
tttcaccagt actacagtta aggccgcctg ttggtgggcg gggatcaagc aggaatttgg    14160
cattccctac aatccccaaa gtcaaggagt aatagaatct atgaataaag aattaaagaa    14220
aattatagga caggtaagag atcaggctga acatcttaag acagcagtac aaatggcagt    14280
attcatccac aattttaaaa gaaaagggg gattgggggg tacagtgcag gggaagaat    14340 agtagacata atagcaacag acatacaaac taaagaatta caaaaacaaa ttacaaaaat    14400
tcaaaatttt cgggtttatt acagggacag cagagatcca gtttggaaag gaccagcaaa    14460
gctcctctgg aaaggtgaag gggcagtagt aatacaagat aatagtgaca taaaagtagt    14520
gccaagaaga aaagcaaaga tcatcaggga ttatggaaaa cagatggcag gtgatgattg    14580
tgtggcaagt agacaggatg aggattaaca catggaaaag attagtaaaa caccatatgt    14640
atatttcaag gaaagctaag gactggtttt atagacatca ctatgaaagt actaatccaa    14700
aaataagttc agaagtacac atcccactag gggatgctaa attagtaata acaacatatt    14760
ggggtctgca tacaggagaa agagactggc atttgggtca gggagtctcc atagaatgga    14820
ggaaaaagag atatagcaca caagtagacc ctgacctagc agaccaacta attcatctgc    14880
actattttga ttgttttca gaatctgcta taagaaatac catattagga cgtatagtta    14940
gtcctaggtg tgaatatcaa gcaggacata acaaggtagg atctctacag tacttggcac    15000
tagcagcatt aataaaacca aaacagataa agccaccttt gcctagtgtt aggaaactga    15060
cagaggacag atggaacaag ccccagaaga ccaagggcca cagagggagc catacaatga    15120
atggacacta gagcttttag aggaacttaa gagtgaagct gttagacatt ttcctaggat    15180
atggctccat aacttaggac aacatatcta tgaaacttac ggggatactt gggcaggagt    15240
ggaagccata ataagaattc tgcaacaact gctgtttatc catttcagaa ttgggtgtcg    15300
acatagcaga ataggcgtta ctcgacagag gagagcaaga aatggagcca gtagatccta    15360
gactagagcc ctggaagcat ccaggaagtc agcctaaaac tgcttgtacc aattgctatt    15420
gtaaaaagtg ttgctttcat tgccaagttt gtttcatgac aaaagcctta ggcatctcct    15480
atggcaggaa gaagcggaga cagcgacgaa gagctcatca gaacagtcag actcatcaag    15540
cttctctatc aaagcagtaa gtagtacatg taatgcaacc tataatagta gcaatagtag    15600
cattagtagt agcaataata atagcaatag ttgtgtggtc catagtaatc atagaatata    15660
ggaaaatatt aagacaaaga aaaatagaca ggttaattga tagactaata gaaagagcag    15720
aagacagtgg caatgagagt gaaggagaag tatcagcact tgtggagatg ggggtggaaa    15780
tggggcacca tgctccttgg gatattgatg atctgtagtg ctacagaaaa attgtgggtc    15840
```

```
acagtctatt atggggtacc tgtgtggaag gaagcaacca ccactctatt tgtgcatca   15900
gatgctaaag catatgatac agaggtacat aatgtttggg ccacacatgc ctgtgtaccc   15960
acagacccca acccacaaga agtagtattg gtaaatgtga cagaaaattt taacatgtgg   16020
aaaaatgaca tggtagaaca gatgcatgag gatataatca gtttatggga tcaaagccta   16080
aagccatgtg taaaattaac cccactctgt gttagtttaa agtgcactga tttgaagaat   16140
gatactaata ccaatagtag tagcgggaga atgataatgg agaaggaga gataaaaaac   16200
tgctctttca atatcagcac aagcataaga gataaggtgc agaaagaata tgcattcttt   16260
tataaacttg atatagtacc aatagataat accagctata ggttgataag ttgtaacacc   16320
tcagtcatta cacaggcctg tccaaaggta tcctttgagc caattcccat acattattgt   16380
gccccggctg gttttgcgat tctaaaatgt aataataaga cgttcaatgg aacaggacca   16440
tgtacaaatg tcagcacagt acaatgtaca catggaatca ggccagtagt atcaactcaa   16500
ctgctgttaa atggcagtct agcagaagaa gatgtagtaa ttagatctgc caatttcaca   16560
gacaatgcta aaaccataat agtacagctg aacacatctg tagaaattaa ttgtacaaga   16620
cccaacaaca atacaagaaa aagtatccgt atccagaggg gaccagggag agcatttgtt   16680
acaataggaa aaataggaaa tatgagacaa gcacattgta acattagtag agcaaaatgg   16740
aatgccactt taaaacagat agctagcaaa ttaagagaac aatttggaaa taataaaaca   16800
ataatcttta agcaatcctc aggaggggac ccagaaattg taacgcacag ttttaattgt   16860
ggaggggaat ttttctactg taattcaaca caactgttta atagtacttg gtttaatagt   16920
acttggagta ctgaagggtc aaataacact gaaggaagtg acacaatcac actcccatgc   16980
agaataaaac aatttataaa catgtggcag gaagtaggaa aagcaatgta tgcccctccc   17040
atcagtggac aaattagatg ttcatcaaat attactgggc tgctattaac aagagatggt   17100
ggtaataaca acaatgggtc cgagatcttc agacctggag gaggcgatat gagggacaat   17160
tggagaagtg aattatataa atataaagta gtaaaaattg aaccattagg agtagcaccc   17220
accaaggcaa agagaagagt ggtgcagaga gaaaaaagag cagtgggaat aggagctttg   17280
ttccttgggt tcttgggagc agcaggaagc actatgggct gcacgtcaat gacgctgacg   17340
gtacaggcca gacaattatt gtctgatata gtgcagcagc agaacaattt gctgagggct   17400
attgaggcgc aacagcatct gttgcaactc acagtctggg gcatcaaaca gctccaggca   17460
agaatcctgg ctgtggaaag atacctaaag gatcaacagc tcctggggat ttggggttgc   17520
tctggaaaac tcatttgcac cactgctgtg ccttggaatg ctagttggag taataaatct   17580
ctggaacaga tttggaataa catgacctgg atggagtggg acagagaaat taacaattac   17640
acaagcttaa tacactcctt aattgaagaa tcgcaaaacc agcaagaaaa gaatgaacaa   17700
gaattattgg aattagataa atgggcaagt ttgtggaatt ggtttaacat aacaaattgg   17760
ctgtggtata taaaattatt cataatgata gtaggaggct tggtaggttt aagaatagtt   17820
tttgctgtac tttctatagt gaatagagtt aggcagggat attcaccatt atcgtttcag   17880
acccacctcc caatcccgag gggacccgac aggcccgaag gaatagaaga agaaggtgga   17940
gagagagaca gagacagatc cattcgatta gtgaacg                           17977
```

<210> SEQ ID NO 6
<211> LENGTH: 18670
<212> TYPE: DNA
<213> ORGANISM: Artificial Sequence
<220> FEATURE:
<223> OTHER INFORMATION: Plasmid sequence containing HIV-1, E-coli, and
      yeast sequences.

<400> SEQUENCE: 6

```
gatccttagc acttatctgg gacgatctgc ggagcctgtg cctcttcagc taccaccgct      60
tgagagactt actcttgatt gtaacgagga ttgtggaact tctgggacgc agggggtggg     120
aagccctcaa atattggtgg aatctcctac agtattggag tcaggaacta agaatagtg     180
ctgttaactt gctcaatgcc acagccatag cagtagctga ggggacagat agggttatag     240
aagtattaca agcagcttat agagctattc gccacatacc tagaagaata agacagggct     300
tggaaaggat tttgctataa accgggcgcc accatggtga acgcgaaaa gaacgtgatc     360
tacggcccag aaccactgca tccactggaa gacctcaccg ctggtgagat gctcttccga     420
gcactgcgta acatagtca cctccctcaa gcactcgtgg acgtcgtggg agacgagagc     480
ctctcctaca aagaatttt cgaagctact gtgctgttgg cccaaagcct ccataattgt     540
gggtacaaaa tgaacgatgt ggtgagcatt tgtgctgaga ataacactcg cttctttatt     600
cctgtaatcg ctgcttggta catcggcatg attgtcgccc ctgtgaatga atcttacatc     660
ccagatgagc tgtgtaaggt tatgggtatt agcaaacctc aaatcgtctt tactaccaaa     720
aacatcttga ataaggtctt ggaagtccag tctcgtacta acttcatcaa acgcatcatt     780
attctggata ccgtcgaaaa catccacggc tgtgagagcc tccctaactt catctctcgt     840
tacagcgatg gtaatatcgc taatttcaag cccttgcatt ttgatccagt cgagcaagtg     900
gccgctattt tgtgctcctc cggcaccact ggtttgccta aggtgtcat gcagactcac     960
cagaatatct gtgtgcgttt gatccacgct ctcgaccctc gtgtgggtac tcaattgatc    1020
cctggcgtga ctgtgctggt gtatctgcct ttctttcacg cctttggttt ctctattacc    1080
ctgggctatt tcatggtcgg cttgcgtgtc atcatgtttc gtcgcttcga ccaagaagcc    1140
ttcttgaagg ctattcaaga ctacgaggtg cgttccgtga tcaacgtccc ttcagtcatt    1200
ttgttcctga gcaaatctcc tttggttgac aagtatgatc tgagcagctt gcgtgagctg    1260
tgctgtggcg ctgctccttt ggccaaagaa gtggccgagg tcgctgctaa gcgtctgaac    1320
ctccctggta tccgctgcgg ttttggtttg actgagagca cttctgctaa catccatagc    1380
ttgcgagacg agtttaagtc tggtagcctg ggtcgcgtga ctcctcttat ggctgcaaag    1440
atcgccgacc gtgagaccgg caaagcactg ggcccaaatc aagtcggtga attgtgtatt    1500
aagggcccta tggtctctaa aggctacgtg aacaatgtgg aggccactaa agaagccatt    1560
gatgatgatg gctggctcca tagcggcgac ttcggttact atgatgagga cgaacacttc    1620
tatgtggtcg atcgctacaa agaattgatt aagtacaaag gctctcaagt cgcaccagcc    1680
gaactggaag aaattttgct gaagaacccT tgtatccgcg acgtggccgt cgtgggtatc    1740
ccagacttgg aagctggcga gttgcctagc gcctttgtgg tgaaacaacc cggcaaggag    1800
atcactgcta aggaggtcta cgactatttg gccgagcgcg tgtctcacac caaatatctg    1860
cgtggcggcg tccgcttcgt cgattctatt ccacgcaacg ttaccggtaa gatcactcgt    1920
aaagagttgc tgaagcaact cctcgaaaaa gctggcggct agagcggccg catgggtggc    1980
aagtggtcaa aaagtagtgt gattggatgg cctgctgtaa gggaaagaat gagacgagct    2040
gagccagcag cagatggggt gggagcagta tctcgagacc tagaaaaaca tggagcaatc    2100
acaagtagca atacagcagc taacaatgct gcttgtgcct ggctagaagc acaagaggag    2160
gaagaggtgg gttttccagt cacacctcag gtacctttaa gaccaatgac ttacaaggca    2220
gctgtagatc ttagccactt tttaaaagaa aaggggggac tggaagggct aattcactcc    2280
caaagaagac aagatatcct tgatctgtgg atctaccaca cacaaggcta cttccctgat    2340
```

```
tggcagaact acacaccagg gccaggggtc agatatccac tgacctttgg atggtgctac    2400
aagctagtac cagttgagcc agataaggta gaagaggcca ataaaggaga gaacaccagc    2460
ttgttacacc ctgtgagcct gcatggaatg atgaccctg agagagaagt gttagagtgg     2520
aggtttgaca gccgcctagc atttcatcac gtggcccgag agctgcatcc ggagtacttc    2580
aagaactgct gacatcgagc ttgctacaag ggactttccg ctggggactt tccaggagg     2640 cgtggcctgg gcgggactgg ggagtggcga gccctcagat gctgcatata agcagctgct    2700
ttttgcctgt actgggtctc tctggttaga ccagatctga gcctgggagc tctctggcta    2760
actagggaac ccactgctta agcctcaata agcttgcct tgagtgcttc aagtagtgtg     2820
tgcccgtctg ttgtgtgact ctggtaacta gagatccctc agaccctttt agtcagtgtg    2880
gaaaatctct agcactcgag tctagaccct cgaggagaac ttctagtata tccacatacc    2940
taatattatt gccttattaa aaatggaatc ccaacaatta catcaaaatc cacattctct    3000
tcaaaatcaa ttgtcctgta cttccttgtt catgtgtgtt caaaaacgtt atatttatag    3060
gataattata ctctatttct caacaagtaa ttggttgttt ggccgagcgg tctaaggcgc    3120
ctgattcaag aaatatcttg accgcagtta actgtgggaa tactcaggta tcgtaagatg    3180
caagagttcg aatctcttag caaccattat ttttttcctc aacataacga gaacacacag    3240
gggcgctatc gcacagaatc aaattcgatg actggaaatt ttttgttaat tcagaggtc     3300 gcctgacgca tatacctttt tcaactgaaa aattgggaga aaaggaaag gtgagaggcc     3360 ggaaccggct tttcatatag aatagagaag cgttcatgac taaatgcttg catcacaata    3420
cttgaagttg acaatattat ttaaggacct attgtttttt ccaataggtg gttagcaatc    3480
gtcttacttt ctaactttc ttaccttta catttcagca atatatatat atatttcaag      3540
gatataccat tctaatgtct gccctatgt ctgcccctaa aagatcgtc gttttgccag      3600 gtgaccacgt tggtcaagaa atcacagccg aagccattaa ggttcttaaa gctatttctg    3660
atgttcgttc caatgtcaag ttcgatttcg aaaatcattt aattggtggt gctgctatcg    3720
atgctacagg tgtcccactt ccagatgagg cgctggaagc ctccaagaag gttgatgccg    3780
ttttgttagg tgctgtgggt ggtcctaaat ggggtaccgg tagtgttaga cctgaacaag    3840
gtttactaaa aatccgtaaa gaacttcaat tgtacgccaa cttaagacca tgtaactttg    3900
catccgactc tcttttagac ttatctccaa tcaagccaca atttgctaaa ggtactgact    3960
tcgttgttgt cagagaatta gtgggaggta tttactttgg taagaaaag gaagacgatg     4020 gtgatggtgt cgcttgggat agtgaacaat acaccgttcc agaagtgcaa agaatcacaa    4080
gaatggccgc tttcatggcc ctacaacatg agccaccatt gcctatttgg tccttggata    4140
aagctaatgt tttggcctct tcaagattat ggagaaaaac tgtggaggaa accatcaaga    4200
acgaattccc tacattgaag gttcaacatc aattgattga ttctgccgcc atgatcctag    4260
ttaagaaccc aaccccaccta atggtatta taatcaccag caacatgttt ggtgatatca    4320
tctccgatga agcctccgtt atcccaggtt ccttgggttt gttgccatct gcgtccttgg    4380
cctctttgcc agacaagaac accgcatttg gtttgtacga accatgccac ggttctgctc    4440
cagatttgcc aaagaataag gttgacccta tcgccactat cttgtctgct gcaatgatgt    4500
tgaaattgtc attgaacttg cctgaagaag gtaaggccat tgaagatgca gttaaaaagg    4560
ttttggatgc aggtatcaga actggtgatt taggtggttc caacagtacc accgaagtcg    4620
gtgatgctgt cgccgaagaa gttaagaaaa tccttgctta aaaagattct cttttttat    4680 gatatttgta cataaacttt ataaatgaaa ttcataatag aaacgacacg aaattacaaa    4740
```

```
atggaatatg ttcatagggt agacgaaact atatacgcaa tctacataca tttatcaaga    4800
aggagaaaaa ggaggatagt aaaggaatac aggtaagcaa attgatacta atggctcaac    4860
gtgataagga aaaagaattg cactttaaca ttaatattga caaggaggag ggcaccacac    4920
aaaaagttag gtgtaacaga aaatcatgaa actacgattc ctaatttgat attggaggat    4980
tttctctaaa aaaaaaaaaa tacaacaaat aaaaaacact caatgacctg accatttgat    5040
ggagtttaag tcaataccct cttgaaccat ttcccataat ggtgaaagtt ccctcaagaa    5100
ttttactctg tcagaaacgg ccttacgacg tagtcgatat ggtgcactct cagtacaatc    5160
tgctctgatg ccgcatagtt aagccagccc cgacacccgc caacacccgc tgacgcgccc    5220
tgacgggctt gtctgctccc ggcatccgct tacagacaag ctgtgaccgt ctccgggagc    5280
tgcatgtgtc agaggttttc accgtcatca ccgaaacgcg cgagacgaaa gggcctcgtg    5340
atacgcctat ttttataggt taatgtcatg ataataatgg tttcttagga cggatcgctt    5400
gcctgtaact tacacgcgcc tcgtatcttt taatgatgga ataatttggg aatttactct    5460
gtgtttattt attttttatgt tttgtatttg gattttagaa agtaaataaa gaaggtagaa    5520
gagttacgga atgaagaaaa aaaaataaac aaaggtttaa aaaatttcaa caaaaagcgt    5580
actttacata tatatttatt agacaagaaa agcagattaa atagatatac attcgattaa    5640
cgataagtaa aatgtaaaat cacaggattt tcgtgtgtgg tcttctacac agacaagatg    5700
aaacaattcg gcattaatac ctgagagcag gaagagcaag ataaaaggta gtatttgttg    5760
gcgatccccc tagagtcttt tacatcttcg gaaaacaaaa actattttttt ctttaatttc    5820 ttttttttact ttctattttt aatttatata tttatattaa aaaatttaaa ttataattat    5880
ttttatagca cgtgatgaaa aggacccagg tggcactttt cggggaaatg tgcgcggaac    5940
ccctatttgt ttattttttct aaatacattc aaatatgtat ccgctctaga gggcccgttt    6000
aaacccgctg atcagcctcg actgtgcctt ctagttgcca gccatctgtt gtttgcccct    6060
cccccgtgcc ttccttgacc ctggaaggtg ccactcccac tgtcctttcc taataaaatg    6120
aggaaattgc atcgcattgt ctgagtaggt gtcattctat tctgggggggt ggggtggggc    6180 aggacagcaa gggggaggat tgggaagaca atagcaggca tgctggggat gcggtgggct    6240
ctatggcttc tgaggcggaa agaaccagct ggggctctag ggggtatccc cacgcgccct    6300
gtagcggcgc attaagcgcg gcgggtgtgg tggttacgcg cagcgtgacc gctacacttg    6360
ccagcgccct agcgcccgct cctttcgctt tcttcccttc ctttctcgcc acgttcgccg    6420
gctttccccg tcaagctcta aatcggggca tccctttagg gttccgattt agtgctttac    6480
ggcacctcga ccccaaaaaa cttgattagg gtgatggttc acgtagtggg ccatcgccct    6540
gatagacggt ttttcgccct ttgacgttgg agtccacgtt ctttaatagt ggactcttgt    6600
tccaaactgg aacaacactc aaccctatct cggtctattc ttttgattta agggattt    6660 tggggatttc ggcctattgg ttaaaaaatg agctgattta acaaaaattt aacgcgaatt    6720
aattctgtgg aatgtgtgtc agttagggtg tggaaagtcc ccaggctccc caggcaggca    6780
gaagtatgca aagcatgcat ctcaattagt cagcaaccag gtgtggaaag tccccaggct    6840
ccccagcagg cagaagtatg caaagcatgc atctcaatta gtcagcaacc atagtcccgc    6900
ccctaactcc gcccatcccg cccctaactc cgcccagttc cgcccattct ccgccccatg    6960
gctgactaat tttttttatt tatgcagagg ccgaggccgc ctctgcctct gagctattcc    7020
agaagtagtg aggaggcttt tttggaggcc taggcttttg caaaaagctc ccgggagctt    7080
gtatatccat tttcggatct gatcagcacg tgttgacaat taatcatcgg catagtatat    7140
```

```
cggcatagta taatacgaca aggtgaggaa ctaaaccatg gccaagttga ccagtgccgt   7200
tccggtgctc accgcgcgcg acgtcgccgg agcggtcgag ttctggaccg accggctcgg   7260
gttctcccgg gacttcgtgg aggacgactt cgccggtgtg gtccgggacg acgtgaccct   7320
gttcatcagc gcggtccagg accaggtggt gccggacaac accctggcct gggtgtgggt   7380
gcgcggcctg gacgagctgt acgccgagtg gtcggaggtc gtgtccacga acttccggga   7440
cgcctccggg ccggccatga ccgagatcgg cgagcagccg tggggcggg agttcgccct    7500 gcgcgacccg gccggcaact gcgtgcactt cgtggccgag gagcaggact gacacgtgct   7560
acgagatttc gattccaccg ccgccttcta tgaaaggttg ggcttcggaa tcgttttccg   7620
ggacgccggc tggatgatcc tccagcgcgg ggatctcatg ctggagttct tcgcccaccc   7680
caacttgttt attgcagctt ataatggtta caaataaagc aatagcatca caaatttcac   7740
aaataaagca ttttttttcac tgcattctag ttgtggtttg tccaaactca tcaatgtatc   7800
ttatcatgtc tgtataccgt cgacctctag ctagagcttg gcgtaatcat ggtcatagct   7860
gtttcctgtg tgaaattgtt atccgctcac aattccacac aacatacgag ccggaagcat   7920
aaagtgtaaa gcctggggtg cctaatgagt gagctaactc acattaattg cgttgcgctc   7980
actgcccgct ttccagtcgg gaaacctgtc gtgccagctg cattaatgaa tcggccaacg   8040
cgcggggaga ggcggtttgc gtattgggcg ctcttccgct tcctcgctca ctgactcgct   8100
gcgctcggtc gttcggctgc ggcgagcggt atcagctcac tcaaaggcgg taatacggtt   8160
atccacagaa tcaggggata acgcaggaaa gaacatgtga gcaaaaggcc agcaaaaggc   8220
caggaaccgt aaaaaggccg cgttgctggc gttttccat aggctccgcc cccctgacga    8280
gcatcacaaa aatcgacgct caagtcagag gtggcgaaac ccgacaggac tataaagata   8340
ccaggcgttt ccccctggaa gctccctcgt gcgctctcct gttccgaccc tgccgcttac   8400
cggatacctg tccgcctttc tcccttcggg aagcgtggcg ctttctcaat gctcacgctg   8460
taggtatctc agttcggtgt aggtcgttcg ctccaagctg ggctgtgtgc acgaaccccc   8520
cgttcagccc gaccgctgcg ccttatccgg taactatcgt cttgagtcca acccggtaag   8580
acacgactta tcgccactgg cagcagccac tggtaacagg attagcagag cgaggtatgt   8640
aggcggtgct acagagttct tgaagtggtg gcctaactac ggctacacta aggacagt     8700 atttggtatc tgcgctctgc tgaagccagt taccttcgga aaaagagttg gtagctcttg   8760
atccggcaaa caaaccaccg ctggtagcgg tggtttttt gtttgcaagc agcagattac    8820
gcgcagaaaa aaaggatctc aagaagatcc tttgatcttt tctacggggt ctgacgctca   8880
gtggaacgaa aactcacgtt aagggatttt ggtcatgaga ttatcaaaaa ggatcttcac   8940
ctagatcctt ttaaattaaa aatgaagttt taaatcaatc taaagtatat atgagtaaac   9000
ttggtctgac agttaccaat gcttaatcag tgaggcacct atctcagcga tctgtctatt   9060
tcgttcatcc atagttgcct gactccccgt cgtgtagata actacgatac gggagggctt   9120
accatctggc cccagtgctg caatgatacc gcgagaccca cgctcaccgg ctccagattt   9180
atcagcaata aaccagccag ccggaagggc cgagcgcaga agtggtcctg caactttatc   9240
cgcctccatc cagtctatta attgttgccg ggaagctaga gtaagtagtt cgccagttaa   9300 tagtttcgc aacgttgttg ccattgctac aggcatcgtg gtgtcacgct cgtcgtttgg     9360
tatggcttca ttcagctccg gttcccaacg atcaaggcga gttacatgat cccccatgtt   9420
gtgcaaaaaa gcggttagct ccttcggtcc tccgatcgtt gtcagaagta agttggccgc   9480
agtgttatca ctcatggtta tggcagcact gcataattct cttactgtca tgccatccgt   9540
```

```
aagatgcttt tctgtgactg gtgagtactc aaccaagtca ttctgagaat agtgtatgcg    9600
gcgaccgagt tgctcttgcc cggcgtcaat acgggataat accgcgccac atagcagaac    9660
tttaaaagtg ctcatcattg gaaaacgttc ttcggggcga aaactctcaa ggatcttacc    9720
gctgttgaga tccagttcga tgtaacccac tcgtgcaccc aactgatctt cagcatcttt    9780
tactttcacc agcgtttctg ggtgagcaaa acaggaagg caaaatgccg caaaaaaggg    9840
aataagggcg acacggaaat gttgaatact catactcttc cttttcaat attattgaag     9900
catttatcag ggttattgtc tcatgagcgg atacatattt gaatgtattt agaaaaataa    9960
acaaataggg gttccgcgca catttccccg aaaagtgcca cctgacgtcg acggatcggg   10020
agatctcccg atcccctatg gtcgactctc agtacaatct gctctgatgc cgcatagtta   10080
agccagtatc tgctccctgc ttgtgtgttg gaggtcgctg agtagtgcgc gagcaaaatt   10140
taagctacaa caaggcaagg cttgaccgac aattgcatga agaatctgct tagggttagg   10200
cgttttgcgc tgcttcgcga tgtacgggcc agatatacgc gttgacattg attattgact   10260
agttattaat agtaatcaat tacggggtca ttagttcata gcccatatat ggagttccgc   10320
gttacataac ttacggtaaa tggcccgcct ggctgaccgc ccaacgaccc ccgcccattg   10380
acgtcaataa tgacgtatgt tcccatagta acgccaatag ggactttcca ttgacgtcaa   10440
tgggtggact atttacggta aactgcccac ttggcagtac atcaagtgta tcatatgcca   10500
agtacgcccc ctattgacgt caatgacggt aaatggcccg cctggcatta tgcccagtac   10560
atgaccttat gggactttcc tacttggcag tacatctacg tattagtcat cgctattacc   10620
atggtgatgc ggttttggca gtacatcaat gggcgtggat agcggtttga ctcacgggga   10680
tttccaagtc tccaccccat tgacgtcaat gggagtttgt tttggcacca aaatcaacgg   10740
gactttccaa aatgtcgtaa caactccgcc ccattgacgc aaatgggcgg taggcgtgta   10800
cggtgggagg tctatataag cagagctctc tggctaacag tggcgcccga acagggactt   10860
gaaagcgaaa gtaaagccag aggagatctc tcgacgcagg actcggcttg ctgaagcgcg   10920
cacggcaaga ggcgaggggc ggcgactggt gagtacgcca aaaattttga ctagcggagg   10980
ctagaaggag agagatgggt gcgagagcgt cggtattaag cggggagaa ttagataaat    11040
gggaaaaaat tcggttaagg ccaggggaa agaaacaata taaactaaaa catatagtat    11100
gggcaagcag ggagctagaa cgattcgcag ttaatcctgg ccttttagag acatcagaag   11160
gctgtagaca aatactggga cagctacaac catcccttca gacaggatca gaagaactta   11220
gatcattata taatacaata gcagtcctct attgtgtgca tcaaaggata gatgtaaaag   11280
acaccaagga agccttagat aagatagagg aagagcaaaa caaaagtaag aaaaaggcac   11340
agcaagcagc agctgacaca ggaaacaaca gccaggtcag ccaaaattac cctatagtgc   11400
agaacctcca ggggcaaatg gtacatcagg ccatatcacc tagaacttta aatgcatggg   11460
taaaagtagt agaagagaag gctttcagcc cagaagtaat acccatgttt tcagcattat   11520
cagaaggagc cacccacaa gatttaaata ccatgctaaa cacagtgggg ggacatcaag    11580
cagccatgca aatgttaaaa gagaccatca atgaggaagc tgcagaatgg gatagattgc   11640
atccagtgca tgcagggcct attgcaccag gccagatgag agaaccaagg ggaagtgaca   11700
tagcaggaac tactagtacc cttcaggaac aaataggatg gatgacacat aatccaccta   11760
tcccagtagg agaaatctat aaaagatgga taatcctggg attaaataaa atagtaagaa   11820
tgtatagccc taccagcatt ctggacataa gacaaggacc aaaggaaccc tttagagact   11880
atgtagaccg attctataaa actctaagag ccgagcaagc ttcacaagag gtaaaaaatt   11940
```

```
ggatgacaga aaccttgttg gtccaaaatg cgaacccaga ttgtaagact attttaaaag   12000
cattgggacc aggagcgaca ctagaagaaa tgatgacagc atgtcaggga gtggggggac   12060
ccggccataa agcaagagtt ttggctgaag caatgagcca agtaacaaat ccagctacca   12120
taatgataca gaaaggcaat tttaggaacc aaagaaagac tgttaagtgt ttcaattgtg   12180
gcaaagaagg gcacatagcc aaaaattgca gggcccctag gaaaaagggc tgttggaaat   12240
gtggaaagga aggacaccaa atgaaagatt gtactgagag acaggctaat ttttaggga    12300 agatctggcc ttcccacaag ggaaggccag ggaattttct tcagagcaga ccagagccaa   12360
cagccccacc agaagagagc ttcaggtttg gggaagagac aacaactccc tctcagaagc   12420
aggagccgat agacaaggaa ctgtatcctt tagcttccct cagatcactc tttggcagcg   12480 accccctcgtc acaataaaga tagggggggca attaaaggaa gctctattag atacaggagc   12540
agatgataca gtattagaag aaatgaattt gccaggaaga tggaaaccaa aaatgatagg   12600
gggaattgga ggttttatca aagtaggaca gtatgatcag atactcatag aaatctgcgg   12660
acataaagct ataggtacag tattagtagg acctacacct gtcaacataa ttggaagaaa   12720
tctgttgact cagattggct gcactttaaa ttttcccatt agtcctattg agactgtacc   12780
agtaaaatta aagccaggaa tggatggccc aaaagttaaa caatggccat tgacagaaga   12840
aaaaataaaa gcattagtag aaatttgtac agaaatggaa aaggaaggaa aaatttcaaa   12900
aattgggcct gaaaatccat acaatactcc agtatttgcc ataagaaaaa agacagtac    12960 taaatggaga aaattagtag atttcagaga acttaataag agaactcaag atttctggga   13020
agttcaatta ggaataccac atcctgcagg gttaaaacag aaaaaatcag taacagtact   13080
ggatgtgggc gatgcatatt tttcagttcc cttagataaa gacttcagga agtatactgc   13140
atttaccata cctagtataa acaatgagac accagggatt agatatcagt acaatgtgct   13200
tccacaggga tggaaaggat caccagcaat attccagtgt agcatgacaa aaatcttaga   13260
gccttttaga aaacaaaatc cagacatagt catctatcaa tacatggatg atttgtatgt   13320
aggatctgac ttagaaatag ggcagcatag aacaaaaata gaggaactga gacaacatct   13380
gttgaggtgg ggatttacca caccagacaa aaaacatcag aaagaacctc cattcctttg   13440
gatgggttat gaactccatc ctgataaatg gacagtacag cctatagtgc tgccagaaaa   13500
ggacagctgg actgtcaatg acatacagaa attagtggga aaattgaatt gggcaagtca   13560
gatttatgca gggattaaag taaggcaatt atgtaaactt cttaggggaa ccaaagcact   13620
aacagaagta gtaccactaa cagaagaagc agagctagaa ctggcagaaa acagggagat   13680
tctaaaagaa ccggtacatg gagtgtatta tgacccatca aaagacttaa tagcagaaat   13740
acagaagcag gggcaaggcc aatggacata tcaaatttat caagagccat ttaaaaatct   13800
gaaaacagga aaatatgcaa gaatgaaggg tgcccacact aatgatgtga acaattaac    13860 agaggcagta caaaaaatag ccacagaaag catagtaata tggggaaaga ctcctaaatt   13920
taaattaccc atacaaaagg aaacatggga agcatggtgg acagagtatt ggcaagccac   13980
ctggattcct gagtgggagt ttgtcaatac ccctccctta gtgaagttat ggtaccagtt   14040
agagaaagaa cccataatag gagcagaaac tttctatgta gatggggcag ccaatagggg   14100
aactaaatta ggaaaagcag gatatgtaac tgacagagga agacaaaaag ttgtcccct    14160 aacggacaca acaaatcaga agactgagtt acaagcaatt catctagctt tgcaggattc   14220
gggattagaa gtaaacatag tgacagactc acaatatgca ttgggaatca ttcaagcaca   14280
accagataag agtgaatcag agttagtcag tcaaataata gagcagttaa taaaaaagga   14340
```

```
aaaagtctac ctggcatggg taccagcaca caaaggaatt ggaggaaatg aacaagtaga    14400
tgggttggtc agtgctggaa tcaggaaagt actattttta gatggaatag ataaggccca    14460
agaagaacat gagaaatatc acagtaattg gagagcaatg gctagtgatt ttaacctacc    14520
acctgtagta gcaaaagaaa tagtagccag ctgtgataaa tgtcagctaa aaggggaagc    14580
catgcatgga caagtagact gtagcccagg aatatggcag ctagattgta cacatttaga    14640
aggaaaagtt atcttggtag cagttcatgt agccagtgga tatatagaag cagaagtaat    14700
tccagcagag acagggcaag aaacagcata cttcctctta aaattagcag gaagatggcc    14760
agtaaaaaca gtacatacag acaatggcag caatttcacc agtactacag ttaaggccgc    14820
ctgttggtgg gcggggatca agcaggaatt tggcattccc tacaatcccc aaagtcaagg    14880
agtaatagaa tctatgaata aagaattaaa gaaaattata ggacaggtaa gagatcaggc    14940
tgaacatctt aagacagcag tacaaatggc agtattcatc cacaatttta aaagaaaagg    15000
ggggattggg gggtacagtg caggggaaag aatagtagac ataatagcaa cagacataca    15060
aactaaagaa ttacaaaaac aaattacaaa aattcaaaat tttcgggttt attacaggga    15120
cagcagagat ccagtttgga aaggaccagc aaagctcctc tggaaaggtg aaggggcagt    15180
agtaatacaa gataatagtg acataaaagt agtgccaaga agaaaagcaa agatcatcag    15240
ggattatgga aaacagatgg caggtgatga ttgtgtggca agtagacagg atgaggatta    15300
acacatggaa aagattagta aaacaccata tgtatatttc aaggaaagct aaggactggt    15360
tttatagaca tcactatgaa agtactaatc caaaaataag ttcagaagta cacatcccac    15420
taggggatgc taaattagta ataacaacat attggggtct gcatacagga gaaagagact    15480
ggcatttggg tcagggagtc tccatagaat ggaggaaaaa gagatatagc acacaagtag    15540
accctgacct agcagaccaa ctaattcatc tgcactattt tgattgtttt tcagaatctg    15600
ctataagaaa taccatatta ggacgtatag ttagtcctag gtgtgaatat caagcaggac    15660
ataacaaggt aggatctcta cagtacttgg cactagcagc attaataaaa ccaaaacaga    15720
taaagccacc tttgcctagt gttaggaaac tgacagagga cagatggaac aagccccaga    15780
agaccaaggg ccacagaggg agccatacaa tgaatggaca ctagagcttt tagaggaact    15840
taagagtgaa gctgttagac attttcctag gatatggctc cataacttag gacaacatat    15900
ctatgaaact tacggggata cttgggcagg agtggaagcc ataataagaa ttctgcaaca    15960
actgctgttt atccatttca gaattgggtg tcgacatagc agaataggcg ttactcgaca    16020
gaggagagca agaaatggag ccagtagatc ctagactaga gccctggaag catccaggaa    16080
gtcagcctaa aactgcttgt accaattgct attgtaaaaa gtgttgcttt cattgccaag    16140
tttgtttcat gacaaaagcc ttaggcatct cctatggcag gaagaagcgg agacagcgac    16200
gaagagctca tcagaacagt cagactcatc aagcttctct atcaaagcag taagtagtac    16260
atgtaatgca acctataata gtagcaatag tagcattagt agtagcaata ataatagcaa    16320
tagttgtgtg gtccatagta atcatagaat ataggaaaat attaagacaa agaaaaatag    16380
acaggttaat tgatagacta atagaaagag cagaagacag tggcaatgag agtgaaggag    16440
aagtatcagc acttgtggag atgggggtgg aaatggggca ccatgctcct tgggatattg    16500
atgatctgta gtgctacaga aaaattgtgg gtcacagtct attatggggt acctgtgtgg    16560
aaggaagcaa ccaccactct attttgtgca tcagatgcta agcatatga tacagaggta    16620 cataatgttt gggccacaca tgcctgtgta cccacagacc caacccaca agaagtagta    16680 ttggtaaatg tgacagaaaa ttttaacatg tggaaaaatg acatggtaga acagatgcat    16740
```

```
gaggatataa tcagtttatg ggatcaaagc ctaaagccat gtgtaaaatt aaccccactc    16800
tgtgttagtt taaagtgcac tgatttgaag aatgatacta ataccaatag tagtagcggg    16860
agaatgataa tggagaaagg agagataaaa aactgctctt tcaatatcag cacaagcata    16920
agagataagg tgcagaaaga atatgcattc ttttataaac ttgatatagt accaatagat    16980
aataccagct ataggttgat aagttgtaac acctcagtca ttacacaggc ctgtccaaag    17040
gtatcctttg agccaattcc catacattat tgtgccccgg ctggttttgc gattctaaaa    17100
tgtaataata agacgttcaa tggaacagga ccatgtacaa atgtcagcac agtacaatgt    17160
acacatggaa tcaggccagt agtatcaact caactgctgt taaatggcag tctagcagaa    17220
gaagatgtag taattagatc tgccaatttc acagacaatg ctaaaaccat aatagtacag    17280
ctgaacacat ctgtagaaat taattgtaca agacccaaca acaatacaag aaaaagtatc    17340
cgtatccaga ggggaccagg agagcatttt gttacaatag gaaaaatagg aaatatgaga    17400
caagcacatt gtaacattag tagagcaaaa tggaatgcca ctttaaaaca gatagctagc    17460
aaattaagag aacaatttgg aaataataaa acaataatct ttaagcaatc ctcaggaggg    17520
gacccagaaa ttgtaacgca cagttttaat tgtggagggg aattttttcta ctgtaattca    17580 acacaactgt ttaatagtac ttggtttaat agtacttgga gtactgaagg gtcaaataac    17640
actgaaggaa gtgacacaat cacactccca tgcagaataa aacaatttat aaacatgtgg    17700
caggaagtag gaaaagcaat gtatgcccct cccatcagtg gacaaattag atgttcatca    17760
aatattactg ggctgctatt aacaagagat ggtggtaata caacaatggg gtccgagatc    17820
ttcagacctg gaggaggcga tatgagggac aattggagaa gtgaattata taaatataaa    17880
gtagtaaaaa ttgaaccatt aggagtagca cccaccaagg caaagagaag agtggtgcag    17940
agagaaaaaa gagcagtggg aataggagct ttgttccttg ggttcttggg agcagcagga    18000
agcactatgg gctgcacgtc aatgacgctg acggtacagg ccagacaatt attgtctgat    18060
atagtgcagc agcagaacaa tttgctgagg gctattgagg cgcaacagca tctgttgcaa    18120
ctcacagtct ggggcatcaa acagctccag gcaagaatcc tggctgtgga agatacccta    18180
aaggatcaac agctcctggg gatttggggt tgctctggaa aactcatttg caccactgct    18240
gtgccttgga atgctagttg gagtaataaa tctctggaac agatttggaa taacatgacc    18300
tggatggagt gggacagaga aattaacaat tacacaagct taatacactc cttaattgaa    18360
gaatcgcaaa accagcaaga aaagaatgaa caagaattat tggaattaga taaatgggca    18420
agtttgtgga attggtttaa cataacaaat tggctgtggt atataaaatt attcataatg    18480
atagtaggag gcttggtagg tttaagaata gttttttgctg tactttctat agtgaataga    18540
gttaggcagg gatattcacc attatcgttt cagacccacc tcccaatccc gagggggaccc    18600 gacaggcccg aaggaataga agaagaaggt ggagagagag acagagacag atccattcga    18660
ttagtgaacg                                                          18670
```

<210> SEQ ID NO 7
<211> LENGTH: 18670
<212> TYPE: DNA
<213> ORGANISM: Artificial Sequence
<220> FEATURE:
<223> OTHER INFORMATION: Plasmid sequence containing HIV-1, E-coli, and
      yeast sequences.

<400> SEQUENCE: 7

```
gatccttagc acttatctgg gacgatctgc ggagcctgtg cctcttcagc taccaccgct        60
```

-continued

```
tgagagactt actcttgatt gtaacgagga ttgtggaact tctgggacgc agggggtggg     120
aagccctcaa atattggtgg aatctcctac agtattggag tcaggaacta agaatagtg     180 ctgttaactt gctcaatgcc acagccatag cagtagctga ggggacagat agggttatag     240
aagtattaca agcagcttat agagctattc gccacatacc tagaagaata agacagggct     300
tggaaaggat tttgctataa accgggcgcc accatggtaa agcgtgagaa aaatgtcatc     360 tatgccctg agcctctcca tcctttggag gatttgactg ccggcgaaat gctgtttcgt     420
gctctccgca agcactctca tttgcctcaa gccttggtcg atgtggtcgg cgatgaatct     480
ttgagctaca aggagttttt tgaggcaacc gtcttgctgg ctcagtccct ccacaattgt     540
ggctacaaga tgaacgacgt cgttagtatc tgtgctgaaa acaatacccg tttcttcatt     600
ccagtcatcg ccgcatggta tatcggtatg atcgtggctc cagtcaacga gagctacatt     660
cccgacgaac tgtgtaaagt catgggtatc tctaagccac agattgtctt caccactaag     720
aatattctga caaagtcct ggaagtccaa agccgcacca actttattaa gcgtatcatc     780
atcttggaca ctgtggagaa tattcacggt tgcgaatctt tgcctaattt catctctcgc     840
tattcagacg gcaacatcgc aaactttaaa ccactccact cgaccctgt ggaacaagtt     900 gcagccattc tgtgtagcag cggtactact ggactcccaa agggagtcat gcagacccat     960
caaaacattt gcgtgcgtct gatccatgct ctcgatccac gctacggcac tcagctgatt    1020
cctggtgtca ccgtcttggt ctacttgcct ttcttccatg ctttcggctt tcatattact    1080 ttggttact ttatggtcgg tctccgcgtg attatgttcc gccgttttga tcaggaggct    1140
ttcttgaaag ccatccaaga ttatgaagtc cgcagtgtca tcaacgtgcc tagcgtgatc    1200 ctgttttttgt ctaagagccc actcgtggac aagtacgact tgtcttcact gcgtgaattg    1260
tgttgcggtg ccgctccact ggctaaggag gtcgctgaag tggccgccaa acgcttgaat    1320
cttccaggga ttcgttgtgg cttcggcctc accgaatcta ccagtgcgat tatccagact    1380
ctcggggatg agtttaagag cggctctttg gccgtgtca ctccactcat ggctgctaag    1440
atcgctgatc gcgaaactgg taaggctttg ggcccgaacc aagtgggcga gctgtgtatc    1500
aaaggcccta tggtgagcaa gggttatgtc aataacgttg aagctaccaa ggaggccatc    1560
gacgacgacg gctggttgca ttctggtgat tttggatatt acgacgaaga tgagcatttt    1620
tacgtcgtgg atcgttacaa ggagctgatc aaatacaagg gtagccaggt tgctccagct    1680
gagttggagg agattctgtt gaaaaatcca tgcattcgcg atgtcgctgt ggtcggcatt    1740
cctgatctgg aggccggcga actgccttct gctttcgttg tcaagcagcc tggtacagaa    1800
attaccgcca agaagtgta tgattacctg gctgaacgtg tgagccatac taagtacttg    1860
cgtggcggcg tgcgttttgt tgactccatc cctcgtaacg taacaggcaa aattacccgc    1920
aaggagctgt tgaaacaatt gttggtgaag gccggcggtt agagcggccg catgggtggc    1980
aagtggtcaa aaagtagtgt gattggatgg cctgctgtaa gggaaagaat gagacgagct    2040
gagccagcag cagatggggt gggagcagta tctcgagacc tagaaaaaca tggagcaatc    2100
acaagtagca atacagcagc taacaatgct gcttgtgcct ggctagaagc acaagaggag    2160
gaagaggtgg gttttccagt cacacctcag gtacctttaa gaccaatgac ttacaaggca    2220
gctgtagatc ttagccactt ttttaaaagaa aaggggggac tggaagggct aattcactcc    2280
caaagaagac aagatatcct tgatctgtgg atctaccaca cacaaggcta cttccctgat    2340
tggcagaact acacaccagg gccagggggtc agatatccac tgacctttgg atggtgctac    2400
aagctagtac cagttgagcc agataaggta gaagaggcca ataaaggaga gaacaccagc    2460
```

```
ttgttacacc ctgtgagcct gcatggaatg gatgaccctg agagagaagt gttagagtgg   2520
aggtttgaca gccgcctagc atttcatcac gtggcccgag agctgcatcc ggagtacttc   2580
aagaactgct gacatcgagc ttgctacaag ggactttccg ctggggactt tccagggagg   2640
cgtggcctgg gcgggactgg ggagtggcga gccctcagat gctgcatata agcagctgct   2700
ttttgcctgt actgggtctc tctggttaga ccagatctga gcctgggagc tctctggcta   2760
actagggaac ccactgctta agcctcaata aagcttgcct tgagtgcttc aagtagtgtg   2820
tgcccgtctg ttgtgtgact ctggtaacta gagatccctc agaccctttt agtcagtgtg   2880
gaaaatctct agcactcgag tctagaccct cgaggagaac ttctagtata tccacatacc   2940
taatattatt gccttattaa aaatggaatc ccaacaatta catcaaaatc cacattctct   3000
tcaaaatcaa ttgtcctgta cttccttgtt catgtgtgtt caaaaacgtt atatttatag   3060
gataattata ctctatttct caacaagtaa ttggttgttt ggccgagcgg tctaaggcgc   3120
ctgattcaag aaatatcttg accgcagtta actgtgggaa tactcaggta tcgtaagatg   3180
caagagttcg aatctcttag caaccattat tttttttcctc aacataacga gaacacacag   3240
gggcgctatc gcacagaatc aaattcgatg actggaaatt ttttgttaat ttcagaggtc   3300
gcctgacgca tataccttt tcaactgaaa aattgggaga aaaggaaag gtgagaggcc   3360 ggaaccggct tttcatatag aatagagaag cgttcatgac taaatgcttg catcacaata   3420
cttgaagttg acaatattat ttaaggacct attgttttt ccaataggtg gttagcaatc   3480
gtcttacttt ctaactttc ttacctttta catttcagca atatatatat atatttcaag   3540
gatataccat tctaatgtct gccctatgt ctgccctaa aagatcgtc gttttgccag   3600 gtgaccacgt tggtcaagaa atcacagccg aagccattaa ggttcttaaa gctatttctg   3660
atgttcgttc caatgtcaag ttcgatttcg aaaatcattt aattggtggt gctgctatcg   3720
atgctacagg tgtcccactt ccagatgagg cgctggaagc ctccaagaag gttgatgccg   3780
ttttgttagg tgctgtgggt ggtcctaaat ggggtaccgg tagtgttaga cctgaacaag   3840
gtttactaaa aatccgtaaa gaacttcaat tgtacgccaa cttaagacca tgtaactttg   3900
catccgactc tcttttagac ttatctccaa tcaagccaca atttgctaaa ggtactgact   3960
tcgttgttgt cagagaatta gtgggaggta tttactttgg taagagaaag gaagacgatg   4020
gtgatggtgt cgcttgggat agtgaacaat acaccgttcc agaagtgcaa agaatcacaa   4080
gaatggccgc tttcatggcc ctacaacatg agccaccatt gcctatttgg tccttggata   4140
aagctaatgt tttggcctct tcaagattat ggagaaaaac tgtggaggaa accatcaaga   4200
acgaattccc tacattgaag gttcaacatc aattgattga ttctgccgcc atgatcctag   4260
ttaagaaccc aaccccaccta aatggtatta taatcaccag caacatgttt ggtgatatca   4320
tctccgatga agcctccgtt atcccaggtt ccttgggttt gttgccatct gcgtccttgg   4380
cctctttgcc agacaagaac accgcatttg gtttgtacga accatgccac ggttctgctc   4440
cagatttgcc aaagaataag gttgacccta tcgccactat cttgtctgct gcaatgatgt   4500
tgaaattgtc attgaacttg cctgaagaag gtaaggccat tgaagatgca gttaaaaagg   4560
ttttggatgc aggtatcaga actggtgatt taggtggttc caacagtacc accgaagtcg   4620
gtgatgctgt cgccgaagaa gttaagaaaa tccttgctta aaaagattct ctttttttat   4680
gatatttgta cataaacttt ataaatgaaa ttcataatag aaacgacacg aaattacaaa   4740
atggaatatg ttcatagggt agacgaaact atatacgcaa tctacataca tttatcaaga   4800
aggagaaaaa ggaggatagt aaaggaatac aggtaagcaa attgatacta atggctcaac   4860
```

```
gtgataagga aaaagaattg cactttaaca ttaatattga caaggaggag ggcaccacac    4920
aaaaagttag gtgtaacaga aaatcatgaa actacgattc ctaatttgat attggaggat    4980
tttctctaaa aaaaaaaaaa tacaacaaat aaaaaacact caatgacctg accatttgat    5040
ggagtttaag tcaatacctt cttgaaccat ttcccataat ggtgaaagtt ccctcaagaa    5100
ttttactctg tcagaaacgg ccttacgacg tagtcgatat ggtgcactct cagtacaatc    5160
tgctctgatg ccgcatagtt aagccagccc cgacacccgc caacacccgc tgacgcgccc    5220
tgacgggctt gtctgctccc ggcatccgct tacagacaag ctgtgaccgt ctccgggagc    5280
tgcatgtgtc agaggttttc accgtcatca ccgaaacgcg cgagacgaaa gggcctcgtg    5340
atacgcctat ttttataggt taatgtcatg ataataatgg tttcttagga cggatcgctt    5400
gcctgtaact tacacgcgcc tcgtatcttt taatgatgga ataatttggg aatttactct    5460
gtgtttattt attttttatgt tttgtatttg gattttagaa agtaaataaa gaaggtagaa    5520
gagttacgga atgaagaaaa aaaaataaac aaaggtttaa aaaatttcaa caaaaagcgt    5580
actttacata tatatttatt agacaagaaa agcagattaa atagatatac attcgattaa    5640
cgataagtaa aatgtaaaat cacaggattt tcgtgtgtgg tcttctacac agacaagatg    5700
aaacaattcg gcattaatac ctgagagcag gaagagcaag ataaaaggta gtatttgttg    5760
gcgatccccc tagagtcttt tacatcttcg gaaaacaaaa actatttttt ctttaatttc    5820 ttttttttact ttctattttt aatttatata tttatattaa aaaatttaaa ttataattat    5880
ttttatagca cgtgatgaaa aggacccagg tggcacttttt cggggaaatg tgcgcggaac    5940
ccctatttgt ttatttttct aaatacattc aaatatgtat ccgctctaga gggcccgttt    6000
aaacccgctg atcagcctcg actgtgcctt ctagttgcca gccatctgtt gtttgcccct    6060
cccccgtgcc ttccttgacc ctggaaggtg ccactcccac tgtcctttcc taataaaatg    6120
aggaaattgc atcgcattgt ctgagtaggt gtcattctat tctggggggt ggggtggggc    6180
aggacagcaa gggggaggat tgggaagaca atagcaggca tgctgggat gcggtgggct    6240 ctatggcttc tgaggcggaa agaaccagct ggggctctag ggggtatccc cacgcgccct    6300
gtagcggcgc attaagcgcg gcgggtgtgg tggttacgcg cagcgtgacc gctacacttg    6360
ccagcgccct agcgcccgct cctttcgctt tcttcccttc ctttctcgcc acgttcgccg    6420
gctttccccg tcaagctcta aatcggggca tccctttagg gttccgattt agtgctttac    6480
ggcacctcga ccccaaaaaa cttgattagg gtgatggttc acgtagtggg ccatcgccct    6540
gatagacggt ttttcgccct ttgacgttgg agtccacgtt ctttaatagt ggactcttgt    6600
tccaaactgg aacaacactc aaccctatct cggtctattc ttttgattta agggattt    6660 tggggatttc ggcctattgg ttaaaaaatg agctgattta acaaaattt aacgcgaatt    6720 aattctgtgg aatgtgtgtc agttagggtg tggaaagtcc ccaggctccc caggcaggca    6780
gaagtatgca aagcatgcat ctcaattagt cagcaaccag gtgtggaaag tccccaggct    6840
ccccagcagg cagaagtatg caaagcatgc atctcaatta gtcagcaacc atagtcccgc    6900
ccctaactcc gcccatcccg cccctaactc cgcccagttc cgcccattct ccgccccatg    6960
gctgactaat ttttttttatt tatgcagagg ccgaggccgc ctctgcctct gagctattcc    7020
agaagtagtg aggaggcttt tttggaggcc taggcttttg caaaaagctc ccgggagctt    7080
gtatatccat tttcggatct gatcagcacg tgttgacaat taatcatcgg catagtatat    7140
cggcatagta taatacgaca aggtgaggaa ctaaaccatg gccaagttga ccagtgccgt    7200
tccggtgctc accgcgcgcg acgtcgccgg agcggtcgag ttctggaccg accggctcgg    7260
```

```
gttctcccgg gacttcgtgg aggacgactt cgccggtgtg gtccgggacg acgtgaccct   7320
gttcatcagc gcggtccagg accaggtggt gccggacaac accctggcct gggtgtgggt   7380
gcgcggcctg gacgagctgt acgccgagtg gtcggaggtc gtgtccacga acttccggga   7440
cgcctccggg ccggccatga ccgagatcgg cgagcagccg tggggggcggg agttcgccct   7500 gcgcgacccg gccggcaact gcgtgcactt cgtggccgag gagcaggact gacacgtgct   7560
acgagatttc gattccaccg ccgccttcta tgaaaggttg ggcttcggaa tcgttttccg   7620
ggacgccggc tggatgatcc tccagcgcgg ggatctcatg ctggagttct cgcccaccc    7680 caacttgttt attgcagctt ataatggtta caaataaagc aatagcatca caaatttcac   7740
aaataaagca ttttttttcac tgcattctag ttgtggtttg tccaaactca tcaatgtatc   7800
ttatcatgtc tgtataccgt cgacctctag ctagagcttg gcgtaatcat ggtcatagct   7860
gtttcctgtg tgaaattgtt atccgctcac aattccacac aacatacgag ccggaagcat   7920
aaagtgtaaa gcctggggtg cctaatgagt gagctaactc acattaattg cgttgcgctc   7980
actgcccgct ttccagtcgg gaaacctgtc gtgccagctg cattaatgaa tcggccaacg   8040
cgcggggaga ggcggtttgc gtattgggcg ctcttccgct tcctcgctca ctgactcgct   8100
gcgctcggtc gttcggctgc ggcgagcggt atcagctcac tcaaaggcgg taatacggtt   8160
atccacagaa tcaggggata acgcaggaaa gaacatgtga gcaaaaggcc agcaaaaggc   8220
caggaaccgt aaaaaggccg cgttgctggc gtttttccat aggctccgcc ccctgacga    8280 gcatcacaaa aatcgacgct caagtcagag gtggcgaaac ccgacaggac tataaagata   8340
ccaggcgttt ccccctggaa gctccctcgt gcgctctcct gttccgaccc tgccgcttac   8400
cggatacctg tccgcctttc tcccttcggg aagcgtggcg ctttctcaat gctcacgctg   8460
taggtatctc agttcggtgt aggtcgttcg ctccaagctg ggctgtgtgc acgaacccc    8520 cgttcagccc gaccgctgcg ccttatccgg taactatcgt cttgagtcca acccggtaag   8580
acacgactta tcgccactgg cagcagccac tggtaacagg attagcagag cgaggtatgt   8640
aggcggtgct acagagttct tgaagtggtg gcctaactac ggctacacta aaggacagt    8700 atttggtatc tgcgctctgc tgaagccagt taccttcgga aaaagagttg gtagctcttg   8760
atccggcaaa caaaccaccg ctggtagcgg tggttttttt gtttgcaagc agcagattac   8820
gcgcagaaaa aaggatctca agaagatcc tttgatctt tctacggggt ctgacgctca    8880
gtggaacgaa aactcacgtt aagggatttt ggtcatgaga ttatcaaaaa ggatcttcac   8940
ctagatcctt taaattaaa atgaagtttt aaatcaatc taaagtatat atgagtaaac     9000
ttggtctgac agttaccaat gcttaatcag tgaggcacct atctcagcga tctgtctatt   9060
tcgttcatcc atagttgcct gactccccgt cgtgtagata actacgatac gggagggctt   9120
accatctggc cccagtgctg caatgatacc gcgagaccca cgctcaccgg ctccagattt   9180
atcagcaata accagccag ccggaagggc cgagcgcaga agtggtcctg caactttatc    9240
cgcctccatc cagtctatta attgttgccg ggaagctaga gtaagtagtt cgccagttaa   9300
tagtttcgcc aacgttgttg ccattgctac aggcatcgtg gtgtcacgct cgtcgtttgg   9360
tatggcttca ttcagctccg gttcccaacg atcaaggcga gttacatgat cccccatgtt   9420
gtgcaaaaaa gcggttagct ccttcggtcc tccgatcgtt gtcagaagta agttggccgc   9480
agtgttatca ctcatggtta tggcagcact gcataattct cttactgtca tgccatccgt   9540
aagatgcttt tctgtgactg gtgagtactc aaccaagtca ttctgagaat agtgtatgcg   9600
gcgaccgagt tgctcttgcc cggcgtcaat acgggataat accgcgccac atagcagaac   9660
```

```
tttaaaagtg ctcatcattg gaaaacgttc ttcggggcga aaactctcaa ggatcttacc    9720
gctgttgaga tccagttcga tgtaacccac tcgtgcaccc aactgatctt cagcatcttt    9780
tactttcacc agcgtttctg ggtgagcaaa acaggaagg caaaatgccg caaaaaggg     9840 aataagggcg acacggaaat gttgaatact catactcttc cttttcaat attattgaag    9900 catttatcag ggttattgtc tcatgagcgg atacatattt gaatgtattt agaaaaataa   9960
acaaataggg gttccgcgca catttccccg aaaagtgcca cctgacgtcg acggatcggg   10020
agatctcccg atccctatg gtcgactctc agtacaatct gctctgatgc cgcatagtta    10080
agccagtatc tgctccctgc ttgtgtgttg gaggtcgctg agtagtgcgc gagcaaaatt   10140
taagctacaa caaggcaagg cttgaccgac aattgcatga agaatctgct tagggttagg   10200
cgttttgcgc tgcttcgcga tgtacggggcc agatatacgc gttgacattg attattgact  10260
agttattaat agtaatcaat tacggggtca ttagttcata gcccatatat ggagttccgc   10320
gttacataac ttacggtaaa tggcccgcct ggctgaccgc ccaacgaccc ccgcccattg   10380
acgtcaataa tgacgtatgt tcccatagta acgccaatag ggactttcca ttgacgtcaa   10440
tgggtggact atttacggta aactgcccac ttggcagtac atcaagtgta tcatatgcca   10500
agtacgcccc ctattgacgt caatgacggt aaatggcccg cctggcatta tgcccagtac   10560
atgaccttat gggactttcc tacttggcag tacatctacg tattagtcat cgctattacc   10620
atggtgatgc ggttttggca gtacatcaat gggcgtggat agcggtttga ctcacgggga   10680
tttccaagtc tccaccccat tgacgtcaat gggagtttgt tttggcacca aaatcaacgg   10740
gactttccaa aatgtcgtaa caactccgcc ccattgacgc aaatgggcgg taggcgtgta   10800
cggtgggagg tctatataag cagagctctc tggctaacag tggcgcccga acagggactt   10860
gaaagcgaaa gtaaagccag aggagatctc tcgacgcagg actcggcttg ctgaagcgcg   10920
cacggcaaga ggcgagggggc ggcgactggt gagtacgcca aaaattttga ctagcggagg   10980
ctagaaggag agagatgggt gcgagagcgt cggtattaag cggggagaa ttagataaat    11040 gggaaaaaat tcggttaagg ccagggggaa agaaacaata taaactaaaa catatagtat   11100
gggcaagcag ggagctagaa cgattcgcag ttaatcctgg cctttagag acatcagaag     11160 gctgtagaca aatactggga cagctacaac catcccttca gacaggatca gaagaactta   11220
gatcattata taatacaata gcagtcctct attgtgtgca tcaaaggata gatgtaaaag   11280
acaccaagga agccttagat aagatagagg aagagcaaaa caaaagtaag aaaaaggcac   11340
agcaagcagc agctgacaca ggaaacaaca gccaggtcag ccaaaattac cctatagtgc   11400
agaacctcca ggggcaaatg gtacatcagg ccatatcacc tagaacttta aatgcatggg   11460
taaaagtagt agaagagaag gctttcagcc agaagtaat acccatgttt tcagcattat    11520
cagaaggagc caccccacaa gatttaaata ccatgctaaa cacagtgggg ggacatcaag   11580
cagccatgca aatgttaaaa gagaccatca atgaggaagc tgcagaatgg gatagattgc   11640
atccagtgca tgcagggcct attgcaccag gccagatgag agaaccaagg ggaagtgaca   11700
tagcaggaac tactagtacc cttcaggaac aaataggatg gatgacacat aatccaccta   11760
tcccagtagg agaaatctat aaaagatgga taatcctggg attaaataaa atagtaagaa   11820
tgtatagccc taccagcatt ctggacataa gacaaggacc aaaggaaccc tttagagact   11880
atgtagaccg attctataaa actctaagag ccgagcaagc ttcacaagag gtaaaaaatt   11940
ggatgacaga aaccttgttg gtccaaaatg cgaacccaga ttgtaagact atttttaaaag  12000 cattgggacc aggagcgaca ctagaagaaa tgatgacagc atgtcaggga gtggggggac   12060
```

```
ccggccataa agcaagagtt ttggctgaag caatgagcca agtaacaaat ccagctacca    12120
taatgataca gaaaggcaat tttaggaacc aaagaaagac tgttaagtgt ttcaattgtg    12180
gcaaagaagg gcacatagcc aaaaattgca gggcccctag gaaaaagggc tgttggaaat    12240
gtggaaagga aggacaccaa atgaaagatt gtactgagag acaggctaat tttttaggga    12300
agatctggcc ttcccacaag ggaaggccag ggaattttct tcagagcaga ccagagccaa    12360
cagccccacc agaagagagc ttcaggtttg gggaagagac aacaactccc tctcagaagc    12420
aggagccgat agacaaggaa ctgtatcctt tagcttccct cagatcactc tttggcagcg    12480
acccctcgtc acaataaaga tagggggggca attaaaggaa gctctattag atacaggagc    12540
agatgataca gtattagaag aaatgaattt gccaggaaga tggaaaccaa aaatgatagg    12600
gggaattgga ggttttatca aagtaggaca gtatgatcag atactcatag aaatctgcgg    12660
acataaagct ataggtacag tattagtagg acctacacct gtcaacataa ttggaagaaa    12720
tctgttgact cagattggct gcactttaaa ttttcccatt agtcctattg agactgtacc    12780
agtaaaatta aagccaggaa tggatggccc aaaagttaaa caatggccat tgacagaaga    12840
aaaaataaaa gcattagtag aaatttgtac agaaatggaa aaggaaggaa aaatttcaaa    12900
aattgggcct gaaaatccat acaatactcc agtatttgcc ataaagaaaa aagacagtac    12960
taaatggaga aaattagtag atttcagaga acttaataag agaactcaag atttctggga    13020
agttcaatta ggaataccac atcctgcagg gttaaaacag aaaaaatcag taacagtact    13080
ggatgtgggc gatgcatatt tttcagttcc cttagataaa gacttcagga agtatactgc    13140
atttaccata cctagtataa acaatgagac accagggatt agatatcagt acaatgtgct    13200
tccacaggga tggaaaggat caccagcaat attccagtgt agcatgacaa aaatcttaga    13260
gccttttaga aaacaaaatc cagacatagt catctatcaa tacatggatg atttgtatgt    13320
aggatctgac ttagaaatag ggcagcatag aacaaaaata gaggaactga gacaacatct    13380
gttgaggtgg ggatttacca caccagacaa aaaacatcag aaagaacctc cattcctttg    13440
gatgggttat gaactccatc ctgataaatg gacagtacag cctatagtgc tgccagaaaa    13500
ggacagctgg actgtcaatg acatacagaa attagtggga aaattgaatt gggcaagtca    13560
gatttatgca gggattaaag taaggcaatt atgtaaactt cttaggggaa ccaaagcact    13620
aacagaagta gtaccactaa cagaagaagc agagctagaa ctggcagaaa cagggagatt    13680
tctaaaagaa ccggtacatg gagtgtatta tgacccatca aaagacttaa tagcagaaat    13740
acagaagcag gggcaaggcc aatggacata tcaaatttat caagagccat ttaaaaatct    13800
gaaaacagga aaatatgcaa gaatgaaggg tgcccacact aatgatgtga aacaattaac    13860
agaggcagta caaaaaatag ccacagaaag catagtaata tggggaaaga ctcctaaatt    13920
taaattaccc atacaaaagg aaacatggga agcatggtgg acagagtatt ggcaagccac    13980
ctggattcct gagtgggagt ttgtcaatac ccctccctta gtgaagttat ggtaccagtt    14040
agagaaagaa cccataatag gagcagaaac tttctatgta gatggggcag ccaataggga    14100
aactaaatta ggaaaagcag gatatgtaac tgacagagga agacaaaaag ttgtccccct    14160
aacggacaca acaaatcaga agactgagtt acaagcaatt catctagctt tgcaggattc    14220
gggattagaa gtaaacatag tgacagactc acaatatgca ttgggaatca ttcaagcaca    14280
accagataag agtgaatcag agttagtcag tcaaataata gagcagttaa taaaaaagga    14340
aaaagtctac ctggcatggg taccagcaca caaaggaatt ggaggaaatg aacaagtaga    14400
tgggttggtc agtgctggaa tcaggaaagt actattttta gatggaatag ataaggccca    14460
```

```
agaagaacat gagaaatatc acagtaattg gagagcaatg gctagtgatt ttaacctacc   14520
acctgtagta gcaaaagaaa tagtagccag ctgtgataaa tgtcagctaa aaggggaagc   14580
catgcatgga caagtagact gtagcccagg aatatggcag ctagattgta cacatttaga   14640
aggaaaagtt atcttggtag cagttcatgt agccagtgga tatatagaag cagaagtaat   14700
tccagcagag acagggcaag aaacagcata cttcctctta aaattagcag gaagatggcc   14760
agtaaaaaca gtacatacag acaatggcag caatttcacc agtactacag ttaaggccgc   14820
ctgttggtgg gcggggatca agcaggaatt tggcattccc tacaatcccc aaagtcaagg   14880
agtaatagaa tctatgaata aagaattaaa gaaaattata ggacaggtaa gagatcaggc   14940
tgaacatctt aagacagcag tacaaatggc agtattcatc cacaatttta aagaaaagg    15000
ggggattggg gggtacagtg caggggaaag aatagtagac ataatagcaa cagacataca   15060
aactaaagaa ttacaaaaac aaattacaaa aattcaaaat tttcgggttt attacaggga   15120
cagcagagat ccagtttgga aaggaccagc aaagctcctc tggaaaggtg aaggggcagt   15180
agtaatacaa gataatagtg acataaaagt agtgccaaga agaaaagcaa agatcatcag   15240
ggattatgga aaacagatgg caggtgatga ttgtgtggca agtagacagg atgaggatta   15300
acacatggaa aagattagta aaacaccata tgtatatttc aaggaaagct aaggactggt   15360
tttatagaca tcactatgaa agtactaatc caaaaataag ttcagaagta cacatcccac   15420
taggggatgc taaattagta ataacaacat attggggtct gcatacagga gaaagagact   15480
ggcatttggg tcagggagtc tccatagaat ggaggaaaaa gagatatagc acacaagtag   15540
accctgacct agcagaccaa ctaattcatc tgcactattt tgattgtttt tcagaatctg   15600
ctataagaaa taccatatta ggacgtatag ttagtcctag gtgtgaatat caagcaggac   15660
ataacaaggt aggatctcta cagtacttgg cactagcagc attaataaaa ccaaaacaga   15720
taaagccacc tttgcctagt gttaggaaac tgacagagga cagatggaac aagccccaga   15780
agaccaaggg ccacagaggg agccatacaa tgaatggaca ctagagcttt tagaggaact   15840
taagagtgaa gctgttagac attttcctag gatatggctc cataacttag gacaacatat   15900
ctatgaaact tacggggata cttgggcagg agtggaagcc ataataagaa ttctgcaaca   15960
actgctgttt atccatttca gaattgggtg tcgacatagc agaataggcg ttactcgaca   16020
gaggagagca agaaatggag ccagtagatc ctagactaga gccctggaag catccaggaa   16080
gtcagcctaa aactgcttgt accaattgct attgtaaaaa gtgttgcttt cattgccaag   16140
tttgtttcat gacaaaagcc ttaggcatct cctatggcag gaagaagcgg agacagcgac   16200
gaagagctca tcagaacagt cagactcatc aagcttctct atcaaagcag taagtagtac   16260
atgtaatgca acctataata gtagcaatag tagcattagt agtagcaata ataatagcaa   16320
tagttgtgtg gtccatagta atcatagaat ataggaaaat attaagacaa agaaaaatag   16380
acaggttaat tgatagacta atagaaagag cagaagacag tggcaatgag agtgaaggag   16440
aagtatcagc acttgtggag atgggggtgg aaatggggca ccatgctcct tgggatattg   16500
atgatctgta gtgctacaga aaaattgtgg gtcacagtct attatggggt acctgtgtgg   16560
aaggaagcaa ccaccactct attttgtgca tcagatgcta aagcatatga tacagaggta   16620
cataatgttt gggccacaca tgcctgtgta cccacagacc caacccacac agaagtagta   16680
ttggtaaatg tgacagaaaa ttttaacatg tggaaaaatg acatggtaga acagatgcat   16740
gaggatataa tcagttttatg ggatcaaagc ctaaagccat gtgtaaaatt aaccccactc   16800
tgtgttagtt taaagtgcac tgatttgaag aatgatacta ataccaatag tagtagcggg   16860
```

```
agaatgataa tggagaaagg agagataaaa aactgctctt tcaatatcag cacaagcata    16920
agagataagg tgcagaaaga atatgcattc ttttataaac ttgatatagt accaatagat    16980
aataccagct ataggttgat aagttgtaac acctcagtca ttacacaggc ctgtccaaag    17040
gtatcctttg agccaattcc catacattat tgtgccccgg ctggttttgc gattctaaaa    17100
tgtaataata agacgttcaa tggaacagga ccatgtacaa atgtcagcac agtacaatgt    17160
acacatggaa tcaggccagt agtatcaact caactgctgt taaatggcag tctagcagaa    17220
gaagatgtag taattagatc tgccaatttc acagacaatg ctaaaaccat aatagtacag    17280
ctgaacacat ctgtagaaat taattgtaca agacccaaca acaatacaag aaaaagtatc    17340
cgtatccaga ggggaccagg gagagcattt gttacaatag gaaaaatagg aaatatgaga    17400
caagcacatt gtaacattag tagagcaaaa tggaatgcca ctttaaaaca gatagctagc    17460
aaattaagag aacaatttgg aaataataaa acaataatct ttaagcaatc ctcaggaggg    17520
gacccagaaa ttgtaacgca cagttttaat tgtggagggg aattttttcta ctgtaattca    17580 acacaactgt ttaatagtac ttggtttaat agtacttgga gtactgaagg gtcaaataac    17640
actgaaggaa gtgacacaat cacactccca tgcagaataa aacaatttat aaacatgtgg    17700
caggaagtag gaaaagcaat gtatgcccct cccatcagtg gacaaattag atgttcatca    17760
aatattactg ggctgctatt aacaagagat ggtggtaata acaacaatgg gtccgagatc    17820
ttcagacctg gaggaggcga tatgagggac aattggagaa gtgaattata taaatataaa    17880
gtagtaaaaa ttgaaccatt aggagtagca cccaccaagg caaagagaag agtggtgcag    17940
agagaaaaaa gagcagtggg aataggagct ttgttccttg ggttcttggg agcagcagga    18000
agcactatgg gctgcacgtc aatgacgctg acggtacagg ccagacaatt attgtctgat    18060
atagtgcagc agcagaacaa tttgctgagg gctattgagg cgcaacagca tctgttgcaa    18120
ctcacagtct ggggcatcaa acagctccag gcaagaatcc tggctgtgga agataccta     18180 aaggatcaac agctcctggg gatttgggt tgctctggaa aactcatttg caccactgct     18240
gtgccttgga atgctagttg gagtaataaa tctctggaac agatttggaa taacatgacc     18300
tggatggagt gggacagaga aattaacaat tacacaagct taatacactc cttaattgaa     18360
gaatcgcaaa accagcaaga aaagaatgaa caagaattat tggaattaga taaatgggca     18420
agtttgtgga attggtttaa cataacaaat tggctgtggt atataaaatt attcataatg     18480
atagtaggag gcttggtagg tttaagaata gttttttgctg tactttctat agtgaataga    18540
gttaggcagg atattcacc attatcgttt cagacccacc tcccaatccc gaggggaccc     18600
gacaggcccg aaggaataga agaagaaggt ggagagagag acagagacag atccattcga    18660
ttagtgaacg                                                           18670
```

```
<210> SEQ ID NO 8
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (32)..(39)
<223> OTHER INFORMATION: R=A+G
<220> FEATURE:
<221> NAME/KEY: misc_feature
<222> LOCATION: (36)..(36)
<223> OTHER INFORMATION: D=A+T+G
<220> FEATURE:
<221> NAME/KEY: misc_feature
<222> LOCATION: (48)..(48)
```

```
<223> OTHER INFORMATION: Y=C+T

<400> SEQUENCE: 8
tatgttgtta ttactaattt agcatcccct artggdatrt gtacttcyga                50

<210> SEQ ID NO 9
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (33)..(46)
<223> OTHER INFORMATION: Y=C+T
<220> FEATURE:
<221> NAME/KEY: misc_feature
<222> LOCATION: (39)..(39)
<223> OTHER INFORMATION: R=A+G

<400> SEQUENCE: 9
actaatttag catccctag tgggatgtgt acytctgarc ttaytyttgg                 50

<210> SEQ ID NO 10
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (31)..(36)
<223> OTHER INFORMATION: W=A+T
<220> FEATURE:
<221> NAME/KEY: misc_feature
<222> LOCATION: (32)..(32)
<223> OTHER INFORMATION: N=A+G+C+T
<220> FEATURE:
<221> NAME/KEY: misc_feature
<222> LOCATION: (38)..(47)
<223> OTHER INFORMATION: R=A+G
<220> FEATURE:
<221> NAME/KEY: misc_feature
<222> LOCATION: (45)..(45)
<223> OTHER INFORMATION: Y=C+T
<220> FEATURE:
<221> NAME/KEY: misc_feature
<222> LOCATION: (50)..(50)
<223> OTHER INFORMATION: V=A+C+G

<400> SEQUENCE: 10
gtacttctga acttattttt ggattagtac wntcawartg atgtytrtav                50

<210> SEQ ID NO 11
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (36)..(50)
<223> OTHER INFORMATION: Y=C+T
<220> FEATURE:
<221> NAME/KEY: misc_feature
<222> LOCATION: (44)..(44)
<223> OTHER INFORMATION: N=A+G+C+T
<220> FEATURE:
<221> NAME/KEY: misc_feature
<222> LOCATION: (49)..(49)
<223> OTHER INFORMATION: R=A+G

<400> SEQUENCE: 11
```

```
tttcatagtg atgtctataa aaccagtcct tagctytcyy tganayatry            50
```

<210> SEQ ID NO 12
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (32)..(50)
<223> OTHER INFORMATION: R=A+G
<220> FEATURE:
<221> NAME/KEY: misc_feature
<222> LOCATION: (35)..(35)
<223> OTHER INFORMATION: H=A+T+C
<220> FEATURE:
<221> NAME/KEY: misc_feature
<222> LOCATION: (38)..(47)
<223> OTHER INFORMATION: Y=C+T
<220> FEATURE:
<221> NAME/KEY: misc_feature
<222> LOCATION: (39)..(39)
<223> OTHER INFORMATION: D=A+T+G
<220> FEATURE:
<221> NAME/KEY: misc_feature
<222> LOCATION: (40)..(40)
<223> OTHER INFORMATION: V=A+C+G
<220> FEATURE:
<221> NAME/KEY: misc_feature
<222> LOCATION: (41)..(41)
<223> OTHER INFORMATION: N=A+G+C+T

<400> SEQUENCE: 12

```
gaattggagg aaatgaacaa gtagatgggt trgthagydv nggratyagr            50
```

<210> SEQ ID NO 13
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (32)..(47)
<223> OTHER INFORMATION: R=A+G
<220> FEATURE:
<221> NAME/KEY: misc_feature
<222> LOCATION: (50)..(50)
<223> OTHER INFORMATION: Y=C+T

<400> SEQUENCE: 13

```
tggcatgggt accagcacac aaaggaattg grggraatga rcargtrgay            50
```

<210> SEQ ID NO 14
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (38)..(38)
<223> OTHER INFORMATION: N=A+C+G+T
<220> FEATURE:
<221> NAME/KEY: misc_feature
<222> LOCATION: (41)..(50)
<223> OTHER INFORMATION: R=A+G
<220> FEATURE:
<221> NAME/KEY: misc_feature
<222> LOCATION: (47)..(47)
<223> OTHER INFORMATION: Y=C+T

<400> SEQUENCE: 14
agttaataaa aaaggaaaaa gtctacctgg catgggtncc rgcacayaar    50

<210> SEQ ID NO 15
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (31)..(31)
<223> OTHER INFORMATION: N=A+C+G+T
<220> FEATURE:
<221> NAME/KEY: misc_feature
<222> LOCATION: (36)..(40)
<223> OTHER INFORMATION: Y=C+T
<220> FEATURE:
<221> NAME/KEY: misc_feature
<222> LOCATION: (38)..(38)
<223> OTHER INFORMATION: R=A+G
<220> FEATURE:
<221> NAME/KEY: misc_feature
<222> LOCATION: (42)..(42)
<223> OTHER INFORMATION: V=A+C+G

<400> SEQUENCE: 15
caagcacaac cagataagag tgaatcagag ntagtyaryy avataataga    50

<210> SEQ ID NO 16
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (31)..(46)
<223> OTHER INFORMATION: Y=C+T
<220> FEATURE:
<221> NAME/KEY: misc_feature
<222> LOCATION: (40)..(40)
<223> OTHER INFORMATION: B=T+C+G
<220> FEATURE:
<221> NAME/KEY: misc_feature
<222> LOCATION: (48)..(49)
<223> OTHER INFORMATION: R=A+G

<400> SEQUENCE: 16
actgtgatat ttctcatgtt cttcttgggc yttatctatb ccatcyarra    50

<210> SEQ ID NO 17
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (36)..(39)
<223> OTHER INFORMATION: N=A+C+G+T
<220> FEATURE:
<221> NAME/KEY: misc_feature
<222> LOCATION: (42)..(48)
<223> OTHER INFORMATION: Y=C+T
<220> FEATURE:
<221> NAME/KEY: misc_feature
<222> LOCATION: (45)..(45)
<223> OTHER INFORMATION: R=A+G

<400> SEQUENCE: 17
gccattgctc tccaattact gtgatatttc tcatgntcnt cytgrgcytt    50

<210> SEQ ID NO 18

```
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (32)..(43)
<223> OTHER INFORMATION: Y=C+T
<220> FEATURE:
<221> NAME/KEY: misc_feature
<222> LOCATION: (42)..(48)
<223> OTHER INFORMATION: R=A+G

<400> SEQUENCE: 18
acaggtggta ggttaaaatc actagccatt gytytccaat trytrtgrta         50

<210> SEQ ID NO 19
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (36)..(36)
<223> OTHER INFORMATION: N=A+C=G+T
<220> FEATURE:
<221> NAME/KEY: misc_feature
<222> LOCATION: (41)..(41)
<223> OTHER INFORMATION: B=T+C+G
<220> FEATURE:
<221> NAME/KEY: misc_feature
<222> LOCATION: (50)..(50)
<223> OTHER INFORMATION: Y=C+T

<400> SEQUENCE: 19
actatttctt ttgctactac aggtggtagg ttaaantcac bagccattgy         50

<210> SEQ ID NO 20
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (33)..(48)
<223> OTHER INFORMATION: R=A+G
<220> FEATURE:
<221> NAME/KEY: misc_feature
<222> LOCATION: (36)..(36)
<223> OTHER INFORMATION: V=A+C+G
<220> FEATURE:
<221> NAME/KEY: misc_feature
<222> LOCATION: (39)..(39)
<223> OTHER INFORMATION: Y=C+T

<400> SEQUENCE: 20
aggaaaaagg gctgttggaa atgtggaaag garggvcayc aratgaarga         50

<210> SEQ ID NO 21
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (31)..(49)
<223> OTHER INFORMATION: R=A+G
<220> FEATURE:
<221> NAME/KEY: misc_feature
<222> LOCATION: (34)..(34)
```

```
<223> OTHER INFORMATION: Y=C+T
<220> FEATURE:
<221> NAME/KEY: misc_feature
<222> LOCATION: (50)..(50)
<223> OTHER INFORMATION: M=A+C

<400> SEQUENCE: 21
agccaaaaat tgcagggccc ctaggaaaaa rggytgttgg aaatgtggrm         50

<210> SEQ ID NO 22
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (33)..(50)
<223> OTHER INFORMATION: R=A+G
<220> FEATURE:
<221> NAME/KEY: misc_feature
<222> LOCATION: (42)..(46)
<223> OTHER INFORMATION: Y=C+T

<400> SEQUENCE: 22
gggcacatag ccaaaaattg cagggcccct agraaaaarg gytgtyggar         50

<210> SEQ ID NO 23
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (36)..(46)
<223> OTHER INFORMATION: R=A+G
<220> FEATURE:
<221> NAME/KEY: misc_feature
<222> LOCATION: (43)..(49)
<223> OTHER INFORMATION: Y=C+T

<400> SEQUENCE: 23
gtgtttcaat tgtggcaaag aagggcacat agcharaaat tgyarrgcyc         50

<210> SEQ ID NO 24
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (31)..(42)
<223> OTHER INFORMATION: R=A+G
<220> FEATURE:
<221> NAME/KEY: misc_feature
<222> LOCATION: (33)..(39)
<223> OTHER INFORMATION: N=A+C+G+T

<400> SEQUENCE: 24
ggagtggggg gacccggcca taaagcaaga rtnttrgcng argcaatgag         50

<210> SEQ ID NO 25
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (33)..(45)
```

```
<223> OTHER INFORMATION: R=A+G
<220> FEATURE:
<221> NAME/KEY: misc_feature
<222> LOCATION: (42)..(48)
<223> OTHER INFORMATION: N=A+C+G+T

<400> SEQUENCE: 25
gcatgtcagg gagtgggggg acccggccat aargcaagrg tnttrgcnga            50

<210> SEQ ID NO 26
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (33)..(33)
<223> OTHER INFORMATION: R=A+G
<220> FEATURE:
<221> NAME/KEY: misc_feature
<222> LOCATION: (48)..(48)
<223> OTHER INFORMATION: Y=C+T

<400> SEQUENCE: 26
aaagcattgg gaccaggagc gacactagaa garatgatga cagcatgyca            50

<210> SEQ ID NO 27
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (33)..(50)
<223> OTHER INFORMATION: Y=C+T
<220> FEATURE:
<221> NAME/KEY: misc_feature
<222> LOCATION: (36)..(48)
<223> OTHER INFORMATION: R=A+G

<400> SEQUENCE: 27
ggagcgacac tagaagaaat gatgacagca tgycarggag trggrggrcy            50

<210> SEQ ID NO 28
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (33)..(33)
<223> OTHER INFORMATION: M=A+C
<220> FEATURE:
<221> NAME/KEY: misc_feature
<222> LOCATION: (37)..(37)
<223> OTHER INFORMATION: N=A+C+G+T
<220> FEATURE:
<221> NAME/KEY: misc_feature
<222> LOCATION: (43)..(43)
<223> OTHER INFORMATION: W=A+T

<400> SEQUENCE: 28
ggcccaaaca ttatgtacct ctgtatcata tgmtttngca tcwgatgcac            50

<210> SEQ ID NO 29
<211> LENGTH: 50
<212> TYPE: DNA
<213> ORGANISM: Artificial Sequence
<220> FEATURE:
```

```
<223> OTHER INFORMATION: Oligonucleotide - HIV-1
<220> FEATURE:
<221> NAME/KEY: misc_feature
<222> LOCATION: (39)..(45)
<223> OTHER INFORMATION: R=A+G

<400> SEQUENCE: 29
tgtacctctg tatcatatgc tttagcatct gatgcacara atarrgtggt           50

<210> SEQ ID NO 30
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (34)..(34)
<223> OTHER INFORMATION: N=A+C+G+T
<220> FEATURE:
<221> NAME/KEY: misc_feature
<222> LOCATION: (37)..(43)
<223> OTHER INFORMATION: Y=C+T
<220> FEATURE:
<221> NAME/KEY: misc_feature
<222> LOCATION: (46)..(46)
<223> OTHER INFORMATION: R=A+G

<400> SEQUENCE: 30
agcatctgat gcacaaaata gagtggtggt tgcntcyytc cayacrggta           50

<210> SEQ ID NO 31
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (35)..(43)
<223> OTHER INFORMATION: Y=C+T
<220> FEATURE:
<221> NAME/KEY: misc_feature
<222> LOCATION: (50)..(50)
<223> OTHER INFORMATION: R=A+G

<400> SEQUENCE: 31
atgcacaaaa tagagtggtg gttgcttcct tccayayagg taycccatar           50

<210> SEQ ID NO 32
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (36)..(36)
<223> OTHER INFORMATION: R=A+G
<220> FEATURE:
<221> NAME/KEY: misc_feature
<222> LOCATION: (38)..(38)
<223> OTHER INFORMATION: H=A+T+C
<220> FEATURE:
<221> NAME/KEY: misc_feature
<222> LOCATION: (45)..(45)
<223> OTHER INFORMATION: Y=C+T

<400> SEQUENCE: 32
aaaatagaca ggttaattga tagactaata gaaagrghag aagayagtgg           50

<210> SEQ ID NO 33
```

```
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (32)..(49)
<223> OTHER INFORMATION: R=A+G
<220> FEATURE:
<221> NAME/KEY: misc_feature
<222> LOCATION: (39)..(39)
<223> OTHER INFORMATION: H=A+T+C

<400> SEQUENCE: 33
atagaatata ggaaaatatt aagacaaaga araataraha ggttarttra         50

<210> SEQ ID NO 34
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (33)..(38)
<223> OTHER INFORMATION: R=A+G
<220> FEATURE:
<221> NAME/KEY: misc_feature
<222> LOCATION: (35)..(35)
<223> OTHER INFORMATION: D=A+T+G
<220> FEATURE:
<221> NAME/KEY: misc_feature
<222> LOCATION: (42)..(42)
<223> OTHER INFORMATION: W=A+T
<220> FEATURE:
<221> NAME/KEY: misc_feature
<222> LOCATION: (43)..(49)
<223> OTHER INFORMATION: Y=C+T
<220> FEATURE:
<221> NAME/KEY: misc_feature
<222> LOCATION: (50)..(50)
<223> OTHER INFORMATION: N=A+C+G+T

<400> SEQUENCE: 34
tagcattagt agtagcaata ataatagcaa tartdgtrtg gwyyatagyn         50

<210> SEQ ID NO 35
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (33)..(38)
<223> OTHER INFORMATION: R=A+G
<220> FEATURE:
<221> NAME/KEY: misc_feature
<222> LOCATION: (37)..(49)
<223> OTHER INFORMATION: Y=C+T
<220> FEATURE:
<221> NAME/KEY: misc_feature
<222> LOCATION: (39)..(39)
<223> OTHER INFORMATION: N=A+C+G+T
<220> FEATURE:
<221> NAME/KEY: misc_feature
<222> LOCATION: (44)..(45)
<223> OTHER INFORMATION: H=A+T+C
<220> FEATURE:
<221> NAME/KEY: misc_feature
<222> LOCATION: (50)..(50)
<223> OTHER INFORMATION: M=A+C

<400> SEQUENCE: 35
```

-continued

```
aacctataat agtagcaata gtagcattag tartagyrnt aathhtagym                      50
```

<210> SEQ ID NO 36
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (31)..(32)
<223> OTHER INFORMATION: N=A+C+G+T
<220> FEATURE:
<221> NAME/KEY: misc_feature
<222> LOCATION: (35)..(38)
<223> OTHER INFORMATION: Y=C+T
<220> FEATURE:
<221> NAME/KEY: misc_feature
<222> LOCATION: (39)..(39)
<223> OTHER INFORMATION: M=A+C
<220> FEATURE:
<221> NAME/KEY: misc_feature
<222> LOCATION: (41)..(48)
<223> OTHER INFORMATION: R=A+G
<220> FEATURE:
<221> NAME/KEY: misc_feature
<222> LOCATION: (47)..(47)
<223> OTHER INFORMATION: H=A+T+C

<400> SEQUENCE: 36

```
tgctgtttat ccatttcaga attgggtgtc nncayagymg ratagghrtt                     50
```

<210> SEQ ID NO 37
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (31)..(50)
<223> OTHER INFORMATION: R=A+G
<220> FEATURE:
<221> NAME/KEY: misc_feature
<222> LOCATION: (34)..(49)
<223> OTHER INFORMATION: Y=C+T
<220> FEATURE:
<221> NAME/KEY: misc_feature
<222> LOCATION: (42)..(42)
<223> OTHER INFORMATION: W=A+T

<400> SEQUENCE: 37

```
agccataata agaattctgc aacaactgct rttyryycat twyagratyr                     50
```

<210> SEQ ID NO 38
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (34)..(48)
<223> OTHER INFORMATION: Y=C+T
<220> FEATURE:
<221> NAME/KEY: misc_feature
<222> LOCATION: (35)..(35)
<223> OTHER INFORMATION: N=A+C+G+T
<220> FEATURE:
<221> NAME/KEY: misc_feature
<222> LOCATION: (36)..(36)
<223> OTHER INFORMATION: K=T+G
<220> FEATURE:
<221> NAME/KEY: misc_feature
<222> LOCATION: (41)..(47)

```
<223> OTHER INFORMATION: R=A+G
<220> FEATURE:
<221> NAME/KEY: misc_feature
<222> LOCATION: (44)..(50)
<223> OTHER INFORMATION: D=A+T+G
<220> FEATURE:
<221> NAME/KEY: misc_feature
<222> LOCATION: (45)..(45)
<223> OTHER INFORMATION: H=A+T+C

<400> SEQUENCE: 38
atacttgggc aggagtggaa gccataataa gaaynktgca rcadhtrytd                  50

<210> SEQ ID NO 39
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (32)..(44)
<223> OTHER INFORMATION: Y=C+T
<220> FEATURE:
<221> NAME/KEY: misc_feature
<222> LOCATION: (33)..(49)
<223> OTHER INFORMATION: K=T+G

<400> SEQUENCE: 39
gttcactaat cgaatggatc tgtctctgtc tykctckcca yctycttckt                  50

<210> SEQ ID NO 40
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (33)..(48)
<223> OTHER INFORMATION: Y=C+T
<220> FEATURE:
<221> NAME/KEY: misc_feature
<222> LOCATION: (37)..(41)
<223> OTHER INFORMATION: K=T+G

<400> SEQUENCE: 40
atccgttcac taatcgaatg gatctgtctc tgyctykctc kccayctyct                  50

<210> SEQ ID NO 41
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (37)..(37)
<223> OTHER INFORMATION: B=T+C+G
<220> FEATURE:
<221> NAME/KEY: misc_feature
<222> LOCATION: (38)..(46)
<223> OTHER INFORMATION: Y=C+T
<220> FEATURE:
<221> NAME/KEY: misc_feature
<222> LOCATION: (47)..(47)
<223> OTHER INFORMATION: K=T+G

<400> SEQUENCE: 41
agtgctaagg atccgttcac taatcgaatg gatctgbyty tgyctykctc                  50

<210> SEQ ID NO 42
```

```
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (34)..(34)
<223> OTHER INFORMATION: Y=C+T
<220> FEATURE:
<221> NAME/KEY: misc_feature
<222> LOCATION: (38)..(38)
<223> OTHER INFORMATION: K=T+G
<220> FEATURE:
<221> NAME/KEY: misc_feature
<222> LOCATION: (39)..(39)
<223> OTHER INFORMATION: B=T+C+G
<220> FEATURE:
<221> NAME/KEY: misc_feature
<222> LOCATION: (42)..(42)
<223> OTHER INFORMATION: R=A+G
<220> FEATURE:
<221> NAME/KEY: misc_feature
<222> LOCATION: (46)..(46)
<223> OTHER INFORMATION: W=A+T

<400> SEQUENCE: 42
tctctcaagc ggtggtagct gaagaggcac aggytcckba grtcgwccca          50

<210> SEQ ID NO 43
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (32)..(49)
<223> OTHER INFORMATION: R=A+G
<220> FEATURE:
<221> NAME/KEY: misc_feature
<222> LOCATION: (40)..(40)
<223> OTHER INFORMATION: Y=C+T
<220> FEATURE:
<221> NAME/KEY: misc_feature
<222> LOCATION: (45)..(45)
<223> OTHER INFORMATION: H=A+T+C

<400> SEQUENCE: 43
ctagcagcat taataaaacc aaaacagata arrccrccty trcchagtrt          50

<210> SEQ ID NO 44
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (32)..(48)
<223> OTHER INFORMATION: R=A+G
<220> FEATURE:
<221> NAME/KEY: misc_feature
<222> LOCATION: (33)..(46)
<223> OTHER INFORMATION: Y=C+T
<220> FEATURE:
<221> NAME/KEY: misc_feature
<222> LOCATION: (34)..(34)
<223> OTHER INFORMATION: M=A+C

<400> SEQUENCE: 44
agtcctaggt gtgaatatca agcaggacat arymaggtag grtcyytrca          50

<210> SEQ ID NO 45
```

```
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (32)..(41)
<223> OTHER INFORMATION: R=A+G
<220> FEATURE:
<221> NAME/KEY: misc_feature
<222> LOCATION: (34)..(34)
<223> OTHER INFORMATION: H=A+T+C
<220> FEATURE:
<221> NAME/KEY: misc_feature
<222> LOCATION: (39)..(39)
<223> OTHER INFORMATION: M=A+C
<220> FEATURE:
<221> NAME/KEY: misc_feature
<222> LOCATION: (49)..(49)
<223> OTHER INFORMATION: Y=C+T

<400> SEQUENCE: 45
catattagga cgtatagtta gtcctaggtg trahtatcma rcaggacaya            50

<210> SEQ ID NO 46
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (31)..(31)
<223> OTHER INFORMATION: H=A+T+C
<220> FEATURE:
<221> NAME/KEY: misc_feature
<222> LOCATION: (39)..(44)
<223> OTHER INFORMATION: R=A+G
<220> FEATURE:
<221> NAME/KEY: misc_feature
<222> LOCATION: (40)..(50)
<223> OTHER INFORMATION: Y=C+T

<400> SEQUENCE: 46
ggcgaatagc tctataagct gcttgtaata httctatary yctrtctgty            50

<210> SEQ ID NO 47
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (32)..(48)
<223> OTHER INFORMATION: Y=C+T
<220> FEATURE:
<221> NAME/KEY: misc_feature
<222> LOCATION: (33)..(33)
<223> OTHER INFORMATION: R=A+G
<220> FEATURE:
<221> NAME/KEY: misc_feature
<222> LOCATION: (40)..(40)
<223> OTHER INFORMATION: N=A+C+G+T

<400> SEQUENCE: 47
actgctatgg ctgtggcatt gagcaagtta ayrgcactan tyttyagytc            50

<210> SEQ ID NO 48
<211> LENGTH: 50
<212> TYPE: DNA
<213> ORGANISM: Artificial Sequence
<220> FEATURE:
```

<223> OTHER INFORMATION: Oligonucleotide - HIV-1
<220> FEATURE:
<221> NAME/KEY: misc_feature
<222> LOCATION: (45)..(45)
<223> OTHER INFORMATION: H=A+T+C
<220> FEATURE:
<221> NAME/KEY: misc_feature
<222> LOCATION: (46)..(46)
<223> OTHER INFORMATION: V=A+C+G
<220> FEATURE:
<221> NAME/KEY: misc_feature
<222> LOCATION: (47)..(48)
<223> OTHER INFORMATION: Y=C+T

<400> SEQUENCE: 48
caatatttga gggcttccca cccctgcgt cccagaagtt ccachvyyct          50

<210> SEQ ID NO 49
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (32)..(44)
<223> OTHER INFORMATION: Y=C+T
<220> FEATURE:
<221> NAME/KEY: misc_feature
<222> LOCATION: (35)..(35)
<223> OTHER INFORMATION: V=A+C+G
<220> FEATURE:
<221> NAME/KEY: misc_feature
<222> LOCATION: (39)..(39)
<223> OTHER INFORMATION: R=A+G
<220> FEATURE:
<221> NAME/KEY: misc_feature
<222> LOCATION: (50)..(50)
<223> OTHER INFORMATION: W=A+T

<400> SEQUENCE: 49
ataaagctat aggtacagta ttagtaggac cyacvcctrt yaayataatw          50

<210> SEQ ID NO 50
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (33)..(42)
<223> OTHER INFORMATION: R=A+G
<220> FEATURE:
<221> NAME/KEY: misc_feature
<222> LOCATION: (45)..(45)
<223> OTHER INFORMATION: Y=C+T
<220> FEATURE:
<221> NAME/KEY: misc_feature
<222> LOCATION: (48)..(48)
<223> OTHER INFORMATION: V=A+C+G

<400> SEQUENCE: 50
gaaatctgcg gacataaagc tataggtaca gtrttrrtrg grccyacvcc          50

<210> SEQ ID NO 51
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (36)..(46)

```
<223> OTHER INFORMATION: Y=C+T
<220> FEATURE:
<221> NAME/KEY: misc_feature
<222> LOCATION: (42)..(42)
<223> OTHER INFORMATION: R=A+G

<400> SEQUENCE: 51
actaatgctt tatttttc ttctgtcaat ggccaytgtt trayyyttgg                 50

<210> SEQ ID NO 52
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (35)..(35)
<223> OTHER INFORMATION: N=A+C+G+T
<220> FEATURE:
<221> NAME/KEY: misc_feature
<222> LOCATION: (44)..(44)
<223> OTHER INFORMATION: H=A+T+C
<220> FEATURE:
<221> NAME/KEY: misc_feature
<222> LOCATION: (50)..(50)
<223> OTHER INFORMATION: Y=C+T

<400> SEQUENCE: 52
tttcttctgt caatggccat gtttaactt ttggnccatc cathcctggy               50

<210> SEQ ID NO 53
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (35)..(35)
<223> OTHER INFORMATION: V=A+C+G
<220> FEATURE:
<221> NAME/KEY: misc_feature
<222> LOCATION: (36)..(44)
<223> OTHER INFORMATION: H=A+T+C
<220> FEATURE:
<221> NAME/KEY: misc_feature
<222> LOCATION: (40)..(40)
<223> OTHER INFORMATION: W=A+T
<220> FEATURE:
<221> NAME/KEY: misc_feature
<222> LOCATION: (41)..(41)
<223> OTHER INFORMATION: R=A+G
<220> FEATURE:
<221> NAME/KEY: misc_feature
<222> LOCATION: (45)..(45)
<223> OTHER INFORMATION: D=A+T+G
<220> FEATURE:
<221> NAME/KEY: misc_feature
<222> LOCATION: (46)..(46)
<223> OTHER INFORMATION: N=A+C+G+T

<400> SEQUENCE: 53
ctaaggcttt tgtcatgaaa caaacttggc aatgvhagcw rcahdnttta              50

<210> SEQ ID NO 54
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (31)..(49)
```

```
<223> OTHER INFORMATION: R=A+G
<220> FEATURE:
<221> NAME/KEY: misc_feature
<222> LOCATION: (36)..(36)
<223> OTHER INFORMATION: S=C+G
<220> FEATURE:
<221> NAME/KEY: misc_feature
<222> LOCATION: (40)..(40)
<223> OTHER INFORMATION: B=T+C+G
<220> FEATURE:
<221> NAME/KEY: misc_feature
<222> LOCATION: (41)..(46)
<223> OTHER INFORMATION: Y=C+T

<400> SEQUENCE: 54
aaagcaacac tttttacaat agcaattggt rcaagsagtb ytaggytgrc          50

<210> SEQ ID NO 55
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (32)..(49)
<223> OTHER INFORMATION: R=A+G
<220> FEATURE:
<221> NAME/KEY: misc_feature
<222> LOCATION: (35)..(35)
<223> OTHER INFORMATION: V=A+C+G
<220> FEATURE:
<221> NAME/KEY: misc_feature
<222> LOCATION: (44)..(44)
<223> OTHER INFORMATION: M=A+C
<220> FEATURE:
<221> NAME/KEY: misc_feature
<222> LOCATION: (45)..(50)
<223> OTHER INFORMATION: K=T+G

<400> SEQUENCE: 55
tggtacaagc agtttttaggc tgacttcctg grtgvttcca gggmkctark          50

<210> SEQ ID NO 56
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (45)..(45)
<223> OTHER INFORMATION: R=A+G
<220> FEATURE:
<221> NAME/KEY: misc_feature
<222> LOCATION: (48)..(48)
<223> OTHER INFORMATION: Y=C+T

<400> SEQUENCE: 56
gtaaagccag aggagatctc tcgacgcagg actcggcttg ctgaragygc          50

<210> SEQ ID NO 57
<211> LENGTH: 50
<212> TYPE: DNA
<213> ORGANISM: Artificial Sequence
<220> FEATURE:
<223> OTHER INFORMATION: Oligonucleotide - HIV-1
<220> FEATURE:
<221> NAME/KEY: misc_feature
<222> LOCATION: (37)..(37)
<223> OTHER INFORMATION: V=A+C+G
<220> FEATURE:
<221> NAME/KEY: misc_feature
<222> LOCATION: (39)..(39)
```

<223> OTHER INFORMATION: R=A+G

<400> SEQUENCE: 57
aagcgaaagt aaagccagag gagatctctc gacgcavgrc tcggcttgct        50

<210> SEQ ID NO 58
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 58
tactaattta gcatccccta        20

<210> SEQ ID NO 59
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 59
acttctgaac ttattttttgg        20

<210> SEQ ID NO 60
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 60
catagtgatg tctataaaac        20

<210> SEQ ID NO 61
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 61
gaattggagg aaatgaacaa        20

<210> SEQ ID NO 62
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 62
ggcatgggta ccagcacaca        20

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 63
gttaataaaa aaggaaaaag        20

<210> SEQ ID NO 64

```
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 64
gcacaaccag ataagagtga                                               20

<210> SEQ ID NO 65
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 65
ttactgtgat atttctcatg                                               20

<210> SEQ ID NO 66
<211> LENGTH: 19
<212> TYPE: DNA
<213> ORGANISM: Artificial Sequence
<220> FEATURE:
<223> OTHER INFORMATION: Oligonucleotide - HIV-1

<400> SEQUENCE: 66
ctacaggtgg taggttaaa                                                19

<210> SEQ ID NO 67
<211> LENGTH: 19
<212> TYPE: DNA
<213> ORGANISM: Artificial Sequence
<220> FEATURE:
<223> OTHER INFORMATION: Oligonucleotide - HIV-1

<400> SEQUENCE: 67 tgggggacc cggccataa                                                 19

<210> SEQ ID NO 68
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 68
ccaggagcga cactagaaga                                               20

<210> SEQ ID NO 69
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 69
gacaggttaa ttgatagact                                               20

<210> SEQ ID NO 70
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 70
```

-continued

```
gaatatagga aaatattaag                                           20

<210> SEQ ID NO 71
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 71
gcattagtag tagcaataat                                           20

<210> SEQ ID NO 72
<211> LENGTH: 20
<212> TYPE: DNA
<213> ORGANISM: Artificial Sequence
<220> FEATURE:
<223> OTHER INFORMATION: Oligonucleotide - HIV-1

<400> SEQUENCE: 72
cctataatag tagcaatagt                                           20

<210> SEQ ID NO 73
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 73
ctgtttatcc atttcagaat tg                                        22

<210> SEQ ID NO 74
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 74
gccataataa gaattctgca ac                                        22

<210> SEQ ID NO 75
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 75
cttgggcagg agtggaagcc at                                        22

<210> SEQ ID NO 76
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 76
gttcactaat cgaatggatc tg                                        22

<210> SEQ ID NO 77
<211> LENGTH: 22
<212> TYPE: DNA
<213> ORGANISM: Artificial Sequence
<220> FEATURE:
```

<223> OTHER INFORMATION: Oligonucleotide - HIV-1

<400> SEQUENCE: 77
ccgttcacta atcgaatgga tc                                              22

<210> SEQ ID NO 78
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 78
gctaaggatc cgttcactaa tc                                              22

<210> SEQ ID NO 79
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 79
gcggtggtag ctgaagaggc ac                                              22

<210> SEQ ID NO 80
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 80
gcagcattaa taaaaccaaa ac                                              22

<210> SEQ ID NO 81
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 81
gtcctaggtg tgaatatcaa gc                                              22

<210> SEQ ID NO 82
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 82
tattaggacg tatagttagt cc                                              22

<210> SEQ ID NO 83
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 83
ggcgaatagc tctataagct gc                                              22

<210> SEQ ID NO 84

```
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 84
ctgctatggc tgtggcattg ag                                              22

<210> SEQ ID NO 85
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 85
gagggcttcc caccccctgc gt                                              22

<210> SEQ ID NO 86
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 86
gctataggta cagtattagt ag                                              22

<210> SEQ ID NO 87
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 87
ctgcggacat aaagctatag gt                                              22

<210> SEQ ID NO 88
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 88 tttttcttc tgtcaatggc ca                                               22

<210> SEQ ID NO 89
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 89
ctgtcaatgg ccattgttta ac                                              22

<210> SEQ ID NO 90
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 90
```

```
ggcttttgtc atgaaacaaa ct                                              22
```

<210> SEQ ID NO 91
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 91

```
gcaacactttt ttacaatagc aa                                             22
```

<210> SEQ ID NO 92
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 92

```
caagcagttt taggctgact tc                                              22
```

<210> SEQ ID NO 93
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 93

```
gccagaggag atctctcgac gc                                              22
```

<210> SEQ ID NO 94
<211> LENGTH: 22
<212> TYPE: DNA
<213> ORGANISM: Artificial Sequence
<220> FEATURE:
<223> OTHER INFORMATION: Oligonucleotide - HIV-1

<400> SEQUENCE: 94

```
gcgaaagtaa agccagagga ga                                              22
```